(12) United States Patent
Kortylewski et al.

(10) Patent No.: US 10,758,624 B2
(45) Date of Patent: Sep. 1, 2020

(54) COMPOUNDS AND COMPOSITIONS INCLUDING PHOSPHOROTHIOATED OLIGODEOXYNUCLEOTIDE, AND METHODS OF USE THEREOF

(71) Applicant: City of Hope, Duarte, CA (US)

(72) Inventors: Marcin Tomasz Kortylewski, Monrovia, CA (US); Piotr Marek Swiderski, San Dimas, CA (US); Dayson Friaca Moreira, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 221 days.

(21) Appl. No.: 15/740,914

(22) PCT Filed: Jun. 30, 2016

(86) PCT No.: PCT/US2016/040361
§ 371 (c)(1),
(2) Date: Dec. 29, 2017

(87) PCT Pub. No.: WO2017/004357
PCT Pub. Date: Jan. 5, 2017

(65) Prior Publication Data
US 2018/0185497 A1    Jul. 5, 2018

Related U.S. Application Data

(60) Provisional application No. 62/264,026, filed on Dec. 7, 2015, provisional application No. 62/187,878, filed on Jul. 2, 2015.

(51) Int. Cl.
| | |
|---|---|
| A61K 31/713 | (2006.01) |
| C12N 15/113 | (2010.01) |
| A61K 47/54 | (2017.01) |
| A61K 45/06 | (2006.01) |
| A61P 37/00 | (2006.01) |
| A61P 35/02 | (2006.01) |
| A61P 35/00 | (2006.01) |
| A61K 48/00 | (2006.01) |

(52) U.S. Cl.
CPC .......... *A61K 47/549* (2017.08); *A61K 31/713* (2013.01); *A61K 45/06* (2013.01); *A61P 35/00* (2018.01); *A61P 35/02* (2018.01); *A61P 37/00* (2018.01); *C12N 15/113* (2013.01); *C12N 15/1135* (2013.01); *A61K 48/00* (2013.01); *C12N 2310/11* (2013.01); *C12N 2310/315* (2013.01); *C12N 2310/3519* (2013.01); *C12N 2320/30* (2013.01); *C12N 2320/31* (2013.01); *C12N 2320/35* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 8,816,056 B2 * | 8/2014 | Swayze .................. | C07H 21/00 536/23.1 |
| 2011/0250138 A1 * | 10/2011 | Fan ..................... | A61K 49/0017 424/9.1 |
| 2012/0065125 A1 * | 3/2012 | Yu ...................... | A61K 31/7105 514/2.3 |
| 2014/0287987 A1 | 9/2014 | Yu et al. | |
| 2015/0190525 A1 * | 7/2015 | Tatro ................... | C12N 15/111 424/78.22 |
| 2016/0298113 A1 * | 10/2016 | Sætrom ............... | C12N 15/113 |

FOREIGN PATENT DOCUMENTS

| | | |
|---|---|---|
| WO | WO-00/61602 A1 | 10/2000 |
| WO | WO-2004/087920 A1 | 10/2004 |
| WO | WO-2008/094254 A2 | 8/2008 |
| WO | WO-2008/094254 A3 | 8/2008 |
| WO | WO-2012/128785 A1 | 9/2012 |
| WO | WO-2012/135736 A2 | 10/2012 |
| WO | WO-2012/135736 A3 | 10/2012 |
| WO | WO-2014/070868 A1 | 5/2014 |
| WO | WO-2014/153023 A1 | 9/2014 |
| WO | WO-2015/075557 A2 | 5/2015 |
| WO | WO-2015/075557 A3 | 5/2015 |

(Continued)

OTHER PUBLICATIONS

Donner, A. et al. (2014). "RNA is for activation," *SciBX:Science—Business exchange*, 3 pages.
Huang, V. et al. (Jan. 22, 2010). "RNAa is conserved in mammalian cells," *PLoS One* 5(1):e8848.
Li, L.C. et al. (Nov. 14, 2006, e-published Nov. 3, 2006). "Small dsRNAs induce transcriptional activation in human cells," *PNAS USA* 103(46):17337-17342.
Reebye, V. et al. (Jan. 2014, e-published Dec. 9, 2013). "A novel RNA oligonucleotide improves liver function and inhibits liver carcinogenesis in vivo," *Hepatology* 59(1):216-227.

(Continued)

*Primary Examiner* — Tracy Vivlemore
(74) *Attorney, Agent, or Firm* — Mintz, Levin, Cohn, Ferris, Glovsky and Popeo, P.C.

(57) ABSTRACT

The present disclosure relates to an isolated compound including a phosphorothioated oligodeoxynucleotide (ODN) sequence conjugated to a short-activating RNA (saRNA) or an antisense oligonucleotide sequence (ASO), compositions of such a compound, and method of treatment of cancer and autoimmune diseases (with or without stimulating immune response), method of immune stimulation, method of activating CEBPA, and method of reducing activity of STAT transcription factor, by one of the disclosed compounds or compositions.

20 Claims, 37 Drawing Sheets

Specification includes a Sequence Listing.

(56) References Cited

FOREIGN PATENT DOCUMENTS

WO     WO-2015/077657 A2     5/2015
WO     WO-2015/077657 A3     5/2015

OTHER PUBLICATIONS

International Search Report dated Dec. 1, 2016, for PCT Application No. PCT/US2016/040361, filed Jun. 30, 2016, 6 pages.
Dhir, R. et al. (Jun. 2002). "Stat3 activation in prostatic carcinomas," *Prostate* 51(4):241-246.
Hedvat, M. et al. (Dec. 8, 2009). "The JAK2 inhibitor AZD1480 potently blocks Stat3 signaling and oncogenesis in solid tumors," *Cancer Cell* 16(6):487-497.
Kortylewski, M. et al. (Oct. 2009, e-published Sep. 133, 2009). "In vivo delivery of siRNA to immune cells by conjugation to a TLR9 agonist enhances antitumor immune responses," *Nat Biotechnol* 27(10):925-932.
Lee, S.O. et al. (Sep. 2004). "RNA interference targeting Stat3 inhibits growth and induces apoptosis of human prostate cancer cells," *Prostate* 60(4):303-309.
Mora, L.B. et al. (Nov. 15, 2002). "Constitutive activation of Stat3 in human prostate tumors and cell lines: direct inhibition of Stat3 signaling induces apoptosis of prostate cancer cells," *Cancer Res* 62(22):6659-6666.
Written Opinion dated Dec. 1, 2016, for PCT Application No. PCT/US2016/040361, filed Jun. 30, 2016, 11 pages.
European Search Report dated Jan. 28, 2019, for EP Patent Application No. 16818778.9, 6 pages.
Extended European Search Report dated May 21, 2019, for EP Patent Application No. 16818778.9, 11 pages.

\* cited by examiner

CpG ODN     C3 Linker     CEBPA

5x(CH₂)₃     2'OMe

FIG. 1A
5' GGTGCATCGATGCAGGGGG 3' - /\/\/\/\/\ - 5' GACCAGUGACAAUGACCGCUU 3' (AS)
                                      3' UUCUGGUCACUGUUACUGGGC 5' (SS)

FIG. 1B
5' GGTGCATCGATGCAGGGGGG 3' - /\/\/\/\/\ - 5' GCGUUAUGUCACUGGUCUU 3' (SS)
                                      3' UUCGCCAGUAACAGUGACCAG 5' (AS)

FIG. 1C
5' GGTGCATCGATGCAGGGGG 3' - /\/\/\/\/\ - 5' GACCAGUGACAAUGACCGCUU 3' (AS)

FIG. 1D
5' GGTGCATCGATGCAGGGGG 3' - /\/\/\/\/\ - 5' GCGUUAUGUCACUGGUCUU 3' (SS)

FIG. 1E
5' GGTGCATCGATGCAGGGGG 3' - /\/\/\/\/\ - 5' UGACCAGUGACAAUGACCGUU 3' (AS)
                                      3' UUACUGGUCACUGUUACUGGC 5' (SS)

FIG. 1F
5' GGTGCATCGATGCAGGGGG 3' - /\/\/\/\/\ - 5' CGGUCAUUGUCACUGGUCAUU 3' (SS)
                                      3' UUGCCAGUAACAGUGACCAGU 5' (AS)

— Untreated
— *CEBPA* saRNA SS/AS (50nM, Lipofectamine)
— CpG-*CEBPA* saRNA SS/AS
······ CpG-*CEBPA* saRNA AS/SS
--- CpG-*CEBPA* saRNA SS/CpG-*CEBPA* saRNA-AS

DU-145

LNCaP S17

FIG. 19D
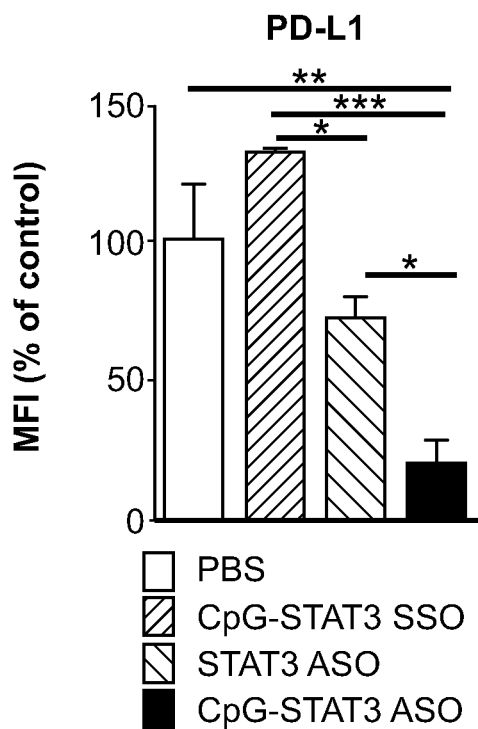
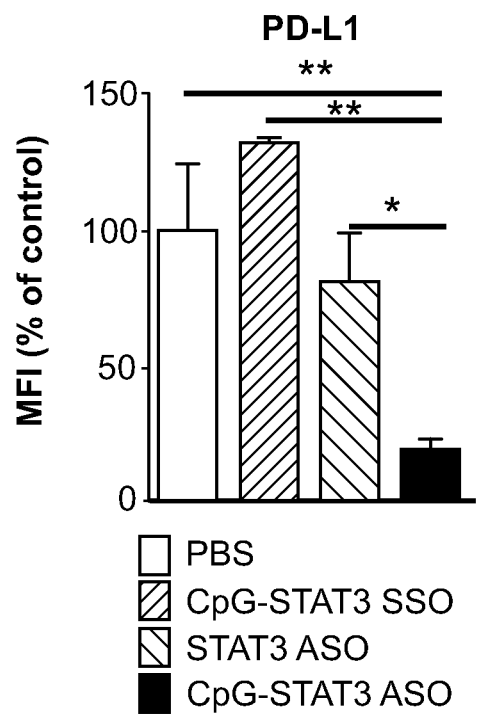

FIG. 19E
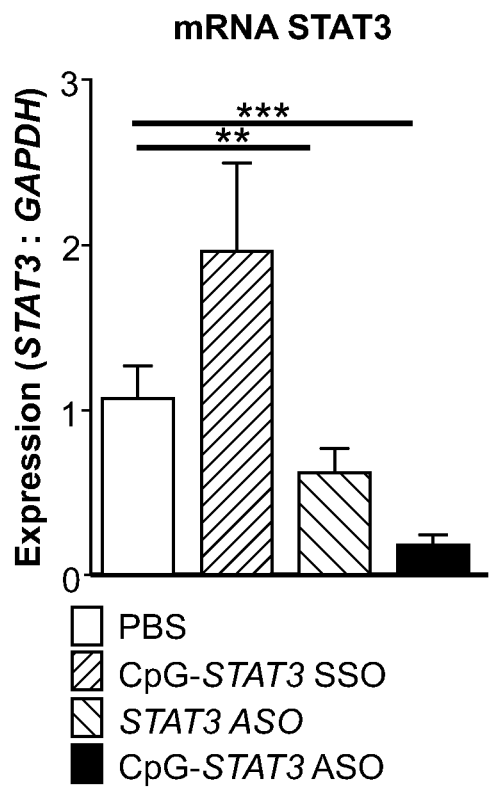
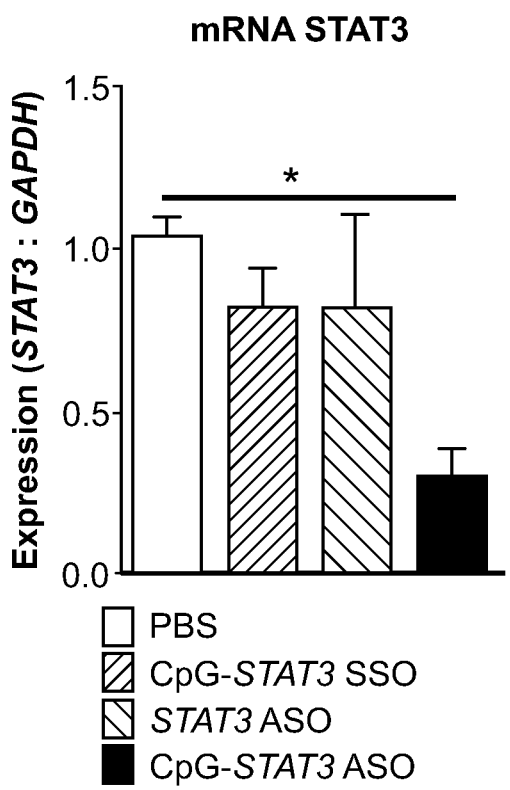

COMPOUNDS AND COMPOSITIONS INCLUDING PHOSPHOROTHIOATED OLIGODEOXYNUCLEOTIDE, AND METHODS OF USE THEREOF

CROSS-REFERENCES TO RELATED APPLICATIONS

This application claims the benefit of U.S. Provisional Application No. 62/187,878, filed Jul. 2, 2015, and U.S. Provisional Application No. 62/264,026, filed on Dec. 7, 2015, contents of each of which is hereby incorporated in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 48440-570001WO_ST25.TXT, created on Jun. 14, 2016, 73,469 bytes, machine format IBM-PC, MS-Windows operating system, is hereby incorporated by reference.

BACKGROUND OF THE DISCLOSURE

Acute myeloid leukemia is characterized by accumulation of immature myeloid progenitor cells. Leukemogenesis results from deregulation of oncogenes, tumor suppressors or transcription factors which control myeloid lineage differentiation, self-renewal and/or proliferation. The transcription factor CCAAT/enhancer binding protein alpha (C/EBPα) promotes differentiation of granulocyte and macrophages and negatively regulates hematopoietic stem cell self-renewal. During emergency granulopoiesis and during leukemogenesis C/EBPα is substituted by transcriptional activity of C/EBPβ and STAT3 transcription factors. Mutations or down-regulation of C/EBPα are frequently observed in patients with AML. Short activating RNAs (saRNAs) are capable of inducing gene expression. A factor in the clinical application of saRNA and other oligonucleotide therapeutics is difficulty in their targeted delivery, additionally complicated by the inherent sensitivity of the immune system to nucleic acids. STAT3 operates in both cancer cells and non-malignant tumor-associated cells. However, targeting transcription factors such as STAT3, is complicated by their lack of enzymatic activity and requires non-pharmacologic approaches. Antisense technology for suppressing STAT3 has limited effect because available antisense oligonucleotides lack cell selectivity. The present disclosure relates to compounds, compositions, and methods of treating cancer, e.g., AML, with saRNA conjugated phosphorothioated oligonucleotides that are stable and are suitable for systemic administration against disseminated cancers. The present disclosure also relates to compounds, compositions, and methods of treating cancer, e.g., prostate cancer and glioblastoma with antisense oligonucleotides conjugated to phosphorothioated oligonucleotides.

BRIEF SUMMARY OF THE DISCLOSURE

In one aspect, the current disclosure provides, inter alia, an isolated compound including a phosphorothioated oligodeoxynucleotide (ODN) conjugated to an oligonucleotide for modulating expression of a target gene. In one aspect, the present disclosure includes an isolated compound including a phosphorothioated oligodeoxynucleotide (ODN), conjugated to an antisense nucleic acid sequence or to a short-activating RNA (saRNA) of a gene of interest. In embodiments, the ODN is a 15 to 30 bases long, single-stranded, partly or completely phosphorothioated oligodeoxynucleotide.

In embodiments, the compound of the present disclosure include a short-activating RNA (saRNA) for enhancing gene expression, or an antisense sequence for suppressing gene expression.

In one aspect, the present disclosure includes a method of treating cancer in a subject with the compound or a composition including the compound, with or without stimulating an immune response in a subject with a compound or a composition including a compound of the present disclosure. In one aspect, the present disclosure includes a method of enhancing C/EBPα expression in a cell with a compound or a composition including a compound including saRNA of C/EBPα conjugated to a phosphorothioated oligonucleotide of the present disclosure. In one aspect, the present disclosure includes a method of suppressing expression of transcription factor Signal Transducer and Activator of Transcription (STAT) (STAT1-STAT6) with a compound or a composition including a compound including an antisense oligonucleotide (ASO) of one or more of STAT1-STAT6 conjugated to a phosphorothioated oligonucleotide of the present disclosure.

In one aspect, the present disclosure includes a method of inhibiting cell growth by contacting the cell with an effective amount of the compound or a composition including the compound.

The short-activating RNA (saRNA) is capable of activating a CCAAT/enhancer-binding protein-α (C/EBPα). The method includes treating myeloma, acute myeloid leukemia, prostate cancer, breast cancer, glioblastoma, ovarian cancer, lung cancer, head and neck cancer, esophageal cancer, skin cancer, melanoma, brain cancer, colorectal cancer, leukemia, or lymphoma. The composition may be administered to the subject by intravenous, parenteral, subcutaneous, intramuscular, transdermal, intraperitoneal, intranasal, aerosol, oral, or topical administration.

Other features and advantages of the disclosure will be apparent from the following detailed description and claims.

Unless noted to the contrary, all publications, references, patents and/or patent applications reference herein are hereby incorporated by reference in their entirety for all purposes.

BRIEF DESCRIPTION OF THE DRAWINGS

FIGS. 1A-1F show design of the chemically stabilizied CpG-CEBPA saRNA oligonucleotides. Sequences of double-stranded and single-stranded CpG-CEBPA saRNA conjugates are shown. Underlined are phosphorothioation sites in the conjugate backbone; the 2'OMe-modified nucleotides are shown inside rectangular boxes and are italicized; position of the linker including five units of the C3 Linker (Glen Research) is indicated; AS=antisense strand; SS=sense strand. FIG. 1A depicts a conjugate sequence comprising SEQ ID NO: 103 and duplex strand SEQ ID NO:2. FIG. 1B depicts a conjugate sequence comprising SEQ ID NO:104 and duplex strand SEQ ID NO:105. FIG. 1C depicts a conjugate sequence comprising SEQ ID NO: 103. FIG. 1D depicts a conjugate sequence comprising SEQ ID NO: 104. FIG. 1E depicts a conjugate sequence comprising SEQ ID NO: 106 and duplex strand SEQ ID NO: 107. FIG. 1F depicts a conjugate sequence comprising SEQ ID NO: 108 and duplex strand SEQ ID NO:109.

FIG. 6A shows line graphs of percentages of AML cells in peripheral blood were assessed using flow cytometry before and after treatment. FIG. 6B shows flow cytometry spectrums showing CpG-CEBPA saRNA treatment reduces the percentage of AML cells in bone marrow and spleen in dose-dependent manner. Shown are representative results of the flow cytometric analysis of GFP+c-Kit+ AML cells in various organs.

FIG. 7A shows representative results of flow cytometry; FIG. 7B shows bar graphs of the levels of CEBPA mRNA were measured in c-Kit+ AML cells enriched from the bone marrow using real-time qPCR.

FIG. 8A shows line graphs of percentages of AML cells in peripheral blood assessed using flow cytometry before, during and after treatment. FIG. 8B shows flow cytometric analysis of AML percentages in peripheral blood, bone marrow and spleen at the end of experiment.

FIG. 13C shows dose-dependent effect of CpG-STAT3ASO compared to the unconjugated STAT3ASO on prostate cancer cells. DU145 cells were treated using different concentration of STAT3 ASO (left panel) or CpG-STAT3ASO (right panel) before analyzing STAT3 mRNA levels using qPCR assay. FIG. 13D shows CpG-STAT3ASO induced a faster STAT3 knockdown than STAT3 ASO alone. Cells were treated with 500 nM of CpG-STAT3ASO, unconjugated STAT3ASO or the negative control CpG-STAT3SSO for 24 or 48 h, as indicated. The activation and protein levels of STAT3 were assessed using Western blotting; β-actin was used as a loading control.

FIG. 15C shows C57BL/6 mice with established RM9 prostate tumors were injected intravenously using 2.5 mg/kg of Cy3-labeled CpG-STAT3 ASO$^{Cy3}$ and euthanized 3 h later. The internalization of oligonucleotide by dendritic cells (DCs) (CD11c+), macrophages (CD11b+F4/80+), B cells (CD19+), T cells (CD3+) or NK cells (CD49b+) were assessed using flow cytometry on single cell suspensions from various organs, as indicated; means±SEM (n=4).

FIG. 16A shows flow cytometry data of Non-Hodgkin's lymphoma B cells incubated with 500 nM of fluorescently-labeled CpG-STAT3 ASO$^{Cy3}$ for one hour without any transfection reagents. The oligonucleotide uptake was measured using flow cytometry. FIG. 16B is a bar graph showing the expression of STAT3 mRNA measured using quantitative real-time PCR (Taqman). OCI-Ly3 cells were incubated for 24 hours with 500 nM of the indicated oligonucleotides. FIG. 16C is a bar graph showing results of OCI-Ly3 cells treated daily with 500 nM of CpG-STAT3ASO for 3 days. Their viability was measured using an XTT (second generation tetrazolium dye; (2,3-bis-(2-methoxy-4-nitro-5-sulfophenyl)-2H-tetrazolium-5-carboxanilide)) assay; results from one of two independent experiments in triplicates is shown; means+/−SEM.

FIG. 17C shows CpG-STAT3ASO induces potent and rapid knockdown of STAT3 at mRNA and protein levels in primary human glioma stem-like cells. Shown are representative results of real time qPCR for STAT3 mRNA levels.

FIG. 18A shows biodistribution studies of fluorescently labeled CSIs demonstrate cell-selective oligonucleotide uptake by TLR9+ GL261 glioma and myeloid cells (CD11b+F4/80$^{LO}$ microglia and CD11b+Gr1+ MDSCs) but not by the non-malignant brain parenchyma. Mice with established orthotopic tumors were euthanized 3 h after injection using the indicated fluorescently labeled reagents and routes of administration (single injection or three repeated IV injections every 6 h). Single cell suspensions from tumors and brain tissues were analyzed for percentages of fluorescent cells using flow cytometry; shown are means±SEM (n=4). FIG. 18B shows representative dot plots showing gating strategy and levels of fluorescent signal in various tested cell populations isolated from IV injected animals. FIG. 18C shows intracranial/IT injections of CpG-STAT3ASO induced STAT3 knockdown in GL261 tumors in vivo. Mice were injected with a single dose of CpG-STAT3ASO (5 mg/kg). Tumors were harvested 21 h later for gene expression analysis using real-time qPCR with normalization to GAPDH expression; means±SEM (n=4).

FIGS. 19A-19E shows that local administration of the CpG-STAT3ASO reduces tumor growth in the distant location and inhibits PD-L1 immune checkpoint regulation. FIG. 19A shows anti-tumor effect of CpGSTAT3ASO conjugated in vivo is more pronounced than STAT3ASO alone. C57/BL6 mice were injected subcutaneously in two locations using 2×10$^5$ mouse prostate cancer RM9 cells. After tumors well established (as shown by arrows), one of the tumors were treated using intra-tumoral (IT) injections of the indicated conjugated 5 mg/kg of CpG-STAT3ASO, STAT3ASO alone, CpGSTAT3SSO or PBS every other day. Tumor growth measured at the indicated time points; means±SEM (n=6). FIG. 19B shows that CpG-STAT3ASO but not STAT3ASO inhibits STAT3 expression in distant, untreated site. Levels of STAT3 mRNA were assessed using qPCR in whole RM9 tumors harvested from differently treated mice. FIGS. 19C-19D shows CpG-STAT3ASO reduces STAT3 activation (FIG. 19C) and PD-L1 immune checkpoint expression (FIG. 19D) on tumor-infiltrating myeloid derived suppressor cells (MDSCs). Levels of pSTAT3 (right panels) and PD-L1 surface expression (left panels) were assessed by flow cytometry in MDSCs (CD11b+Gr1+) isolated from RM9 tumors following treatment as indicated. Shown are representative histogram overlays and bar graphs summarizing results from each group of mice; mean±SEM (n=6). FIG. 19E shows that CpG-STAT3ASO but not STAT3ASO inhibits STAT3 expression in distant, untreated site. Levels of STAT3 mRNA were assessed using qPCR in whole RM9 tumors harvested from differently treated mice.

DETAILED DESCRIPTION OF THE DISCLOSURE

Figure 2A:
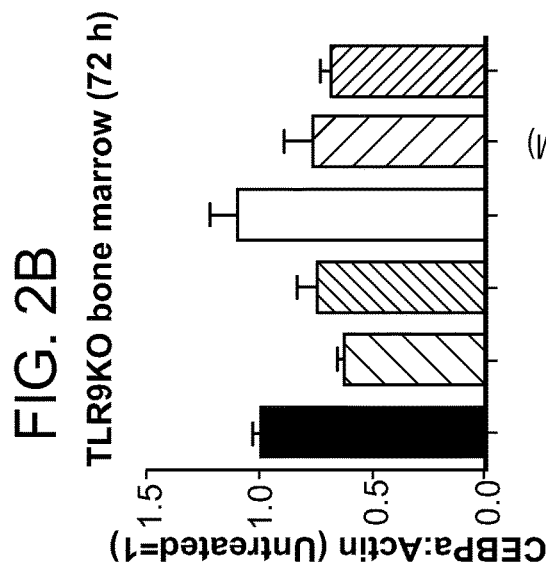
FIGS. 2A and 2B are bar graphs of mRNA expression levels measured by real-time quantitative PCR (qPCR).
Figure 2B:
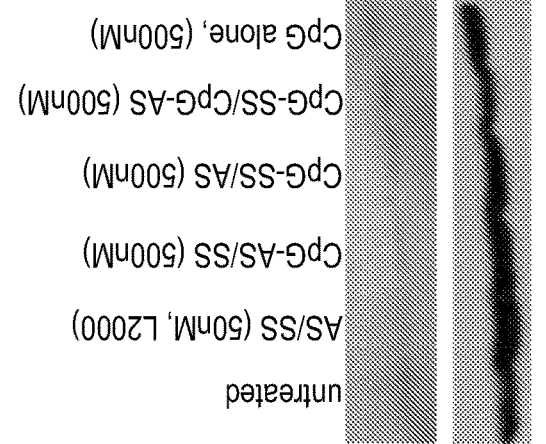
Figure 2C:
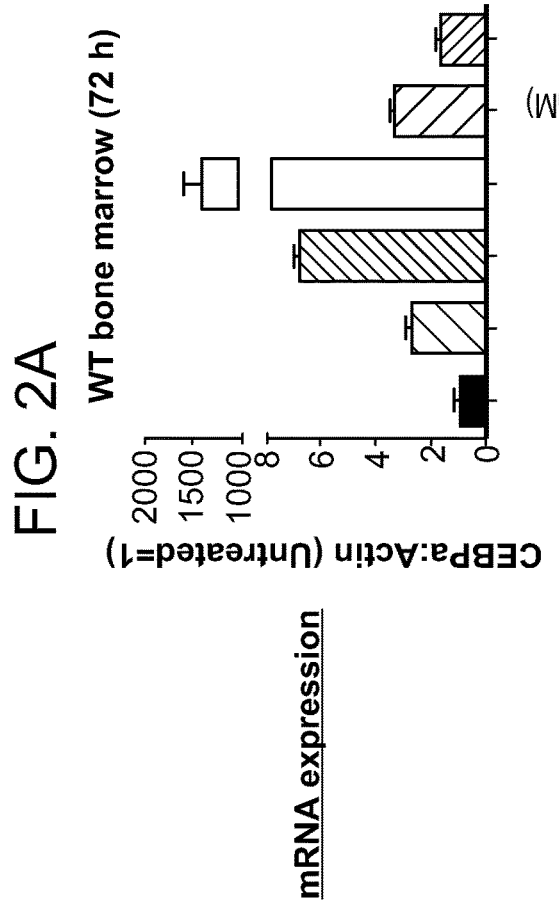
FIGS. 2C and 2D are western blot images of protein expression levels. Fresh bone marrow cells isolated from wild-type (WT) or TLR9-deficient (TLR9KO) mice were incubated in the process of 500 nM of various CpG-saRNA conjugates or transfected with 50 nM of unconjugated saRNA using Lipofectamine 2000. The mRNA and protein levels of C/EBPα were measured using qPCR (FIGS. 2A-2B) and western blotting (FIGS. 2C-2D), respectively.
Figure 2D:
Figure 3:
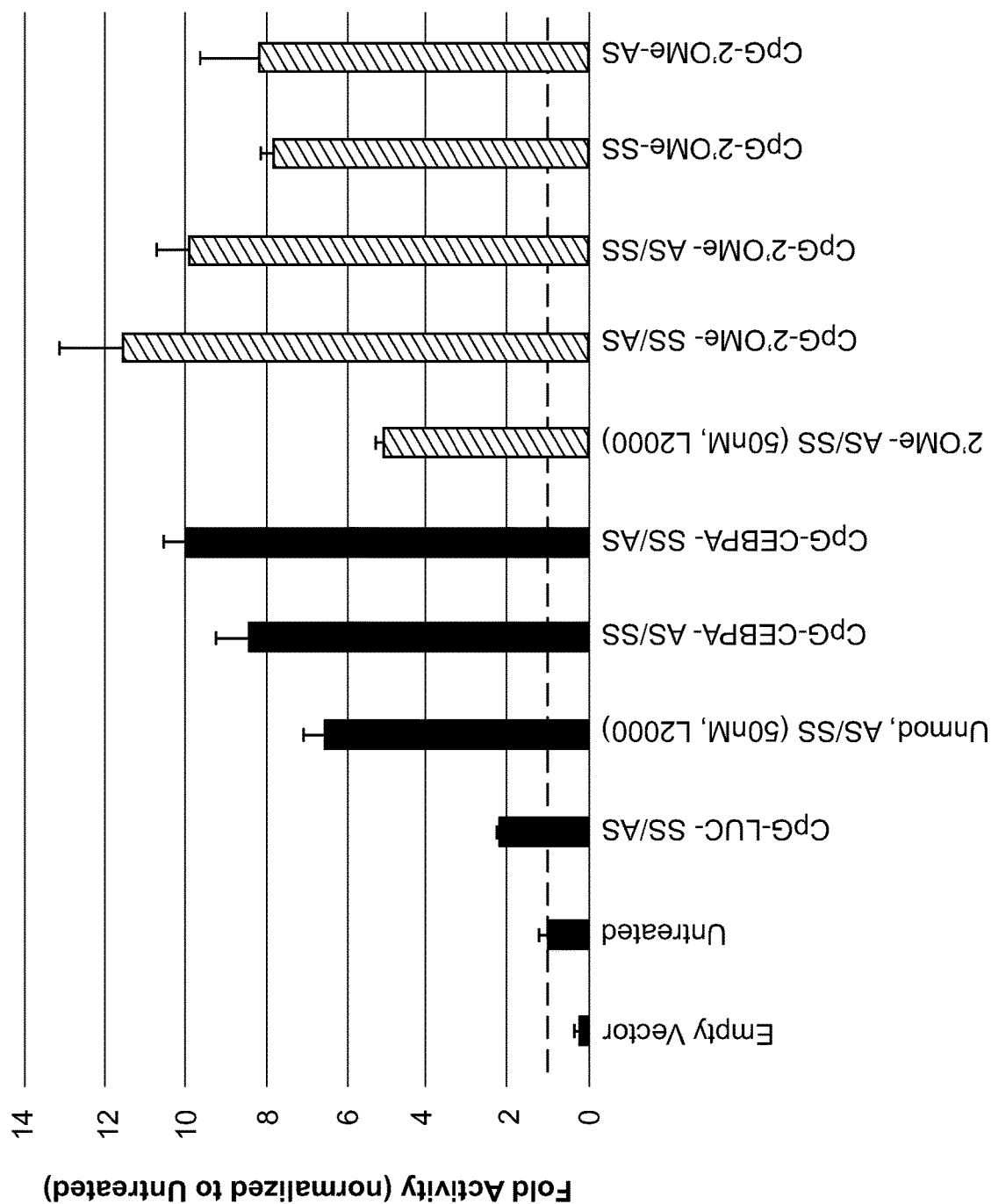
FIG. 3 shows bar graphs showing CpG-CEBPA saRNA triggers transcriptional activity of C/EBPα in target human cancer cells. Human DU145 prostate cancer cells expressing C/EBPα-specific promoter-luciferase construct were incubated in the presence of 500 nM of various CpG-saRNA conjugates or transfected with 50 nM of unconjugated saRNA using Lipofectamine 2000 as indicated; CpG-FLUC-RNA conjugates with a sequence matching firefly luciferase were used as a negative control. 72 h later cells were lysed and analyzed levels using Cignal C/EBP Reporter Assay Kit (Qiagen).
Figure 4A:
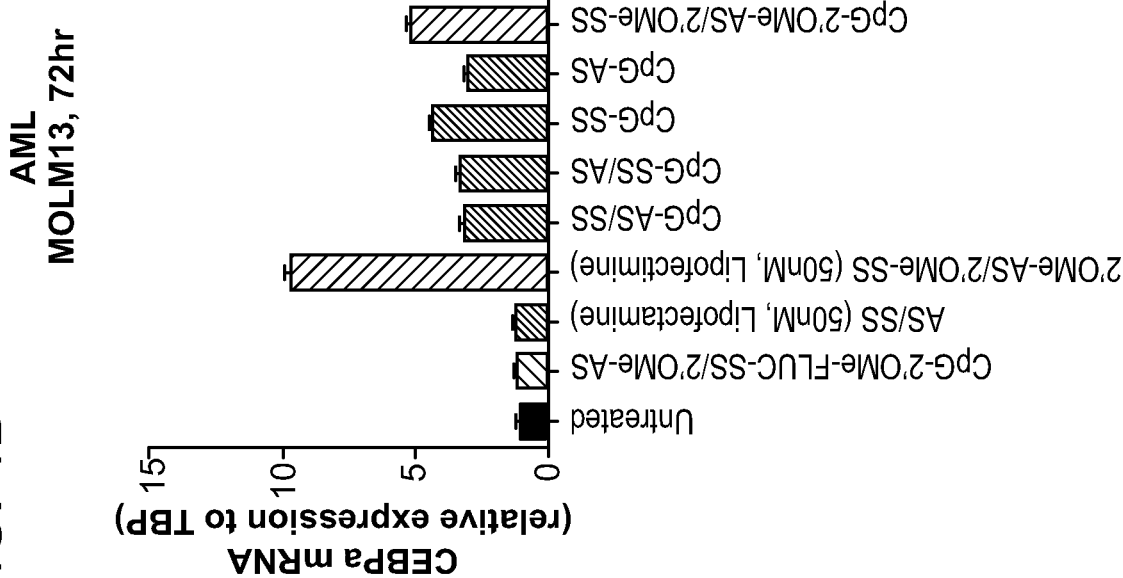
FIGS. 4A and 4B show bar graphs human DU145 prostate cancer cells and MOLM13 leukemia cell, respectively in an assay to show TLR9-dependent effect of CpG-CEBPA saRNA on the C/EBPα mRNA and protein levels in human and mouse cells. Human DU145 prostate cancer cells (FIG. 4A) and MOLM13 leukemia cells (FIG. 4B) were incubated in the process of 500 nM of various CpG-saRNA conjugates or transfected with 50 nM of unconjugated saRNA using Lipofectamine 2000; CpG-FLUC-RNA conjugates with a sequence matching firefly luciferase were uses as a negative control. 72 hours later cells were lysed to isolated RNA for the analysis of CEBPA mRNA levels using real-time quantitative PCR (qPCR).
Figure 4B:
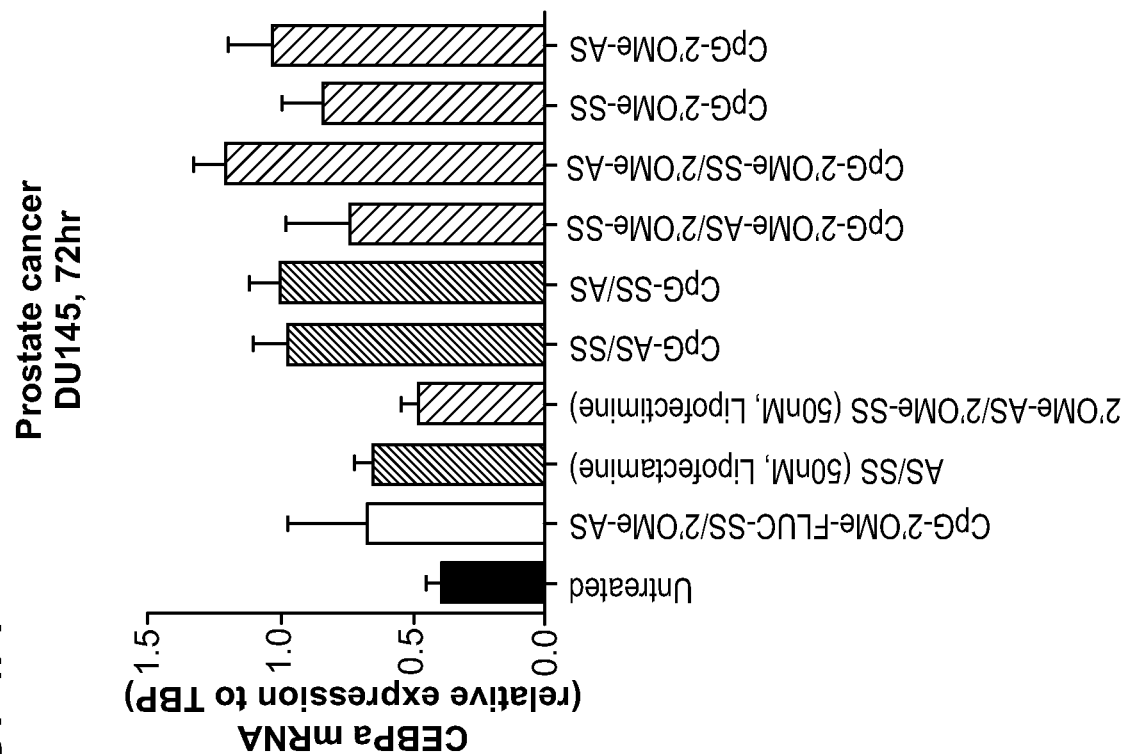
Figure 5A:
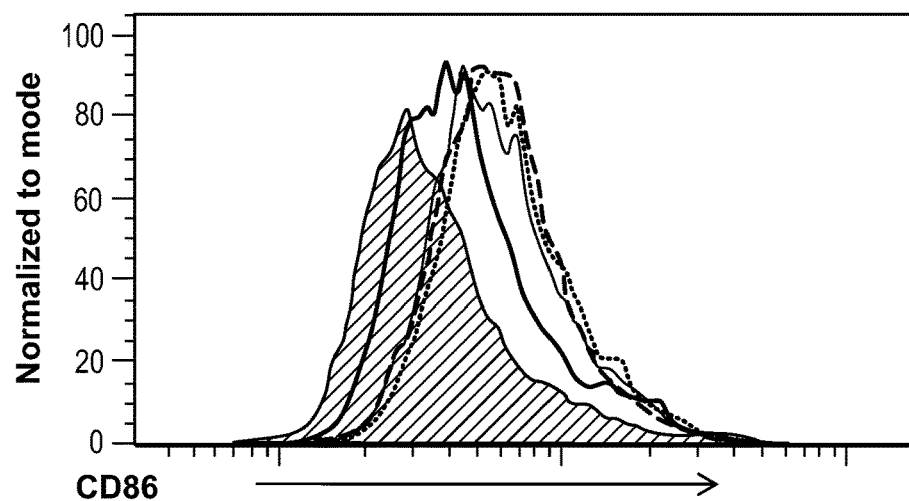
FIGS. 5A-5C are flow cytometry spectra of Human MV4-11 AML cells incubated with 500 nM CpG-CEBPA saRNA or transfected with CEBP saRNA alone in vitro for 48 h. The expression of HLADR and costimulatory molecules CD86 and CD40 was assessed using flow cytometry. Data shows (CD86 (FIG. 5A), CD40 (FIG. 5B), and HLADR (FIG. 5C)) that CpG-CEBPA saRNA has immunostimulatory effects in vivo.
Figure 5B:
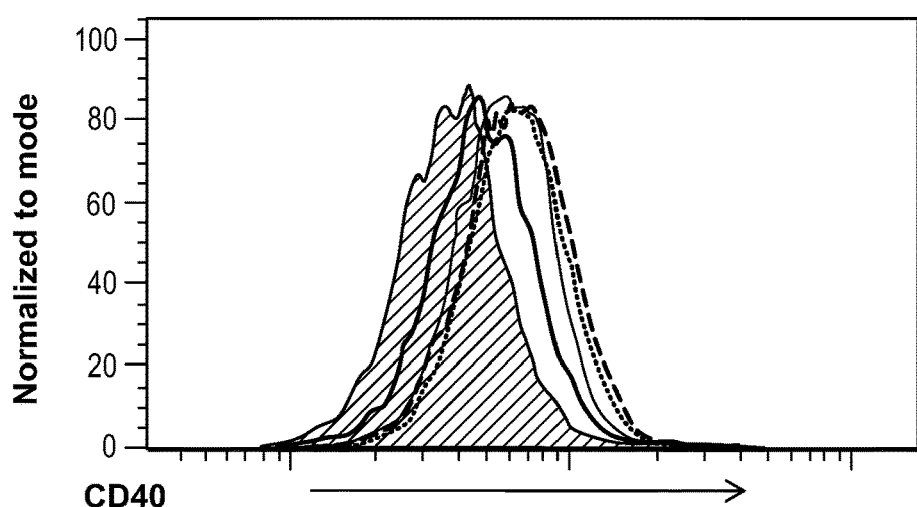
Figure 5C:
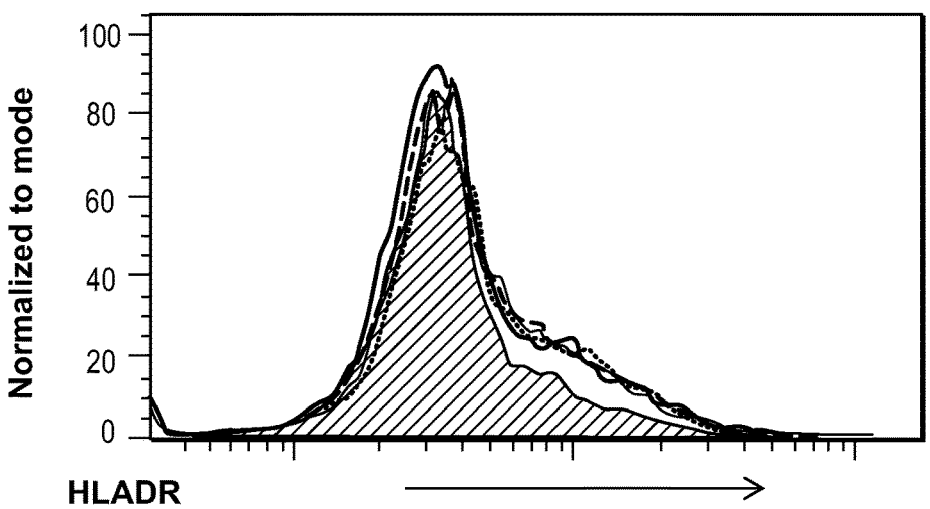
Figure 6A:
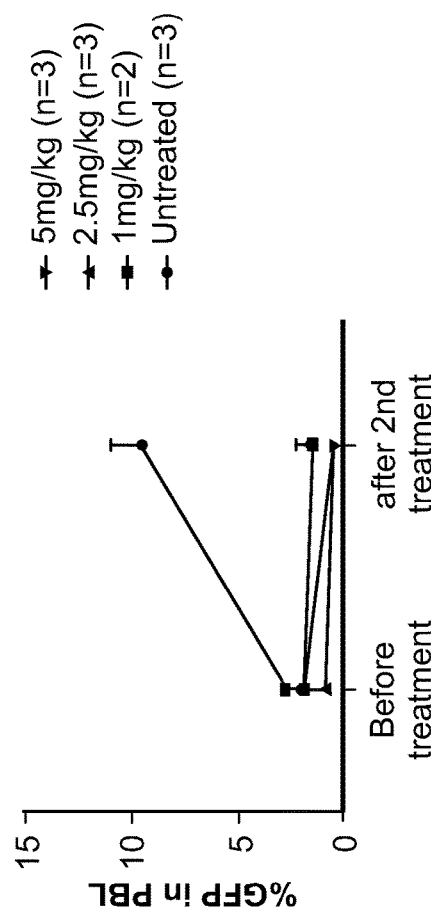
FIGS. 6A-6B show line graphs and flow-cytometry data of dose-dependent effect of CpG-CEBPA saRNA on syngeneic leukemia cells in mice. After Cbfb/MYH11/Mpl leukemia was established (>1%, ranging 1-5% of AML cells in blood), C57BL/6 mice were injected twice using various doses of CpG-CEBPA saRNA every other day and euthanized one day after last treatment.
Figure 6B:
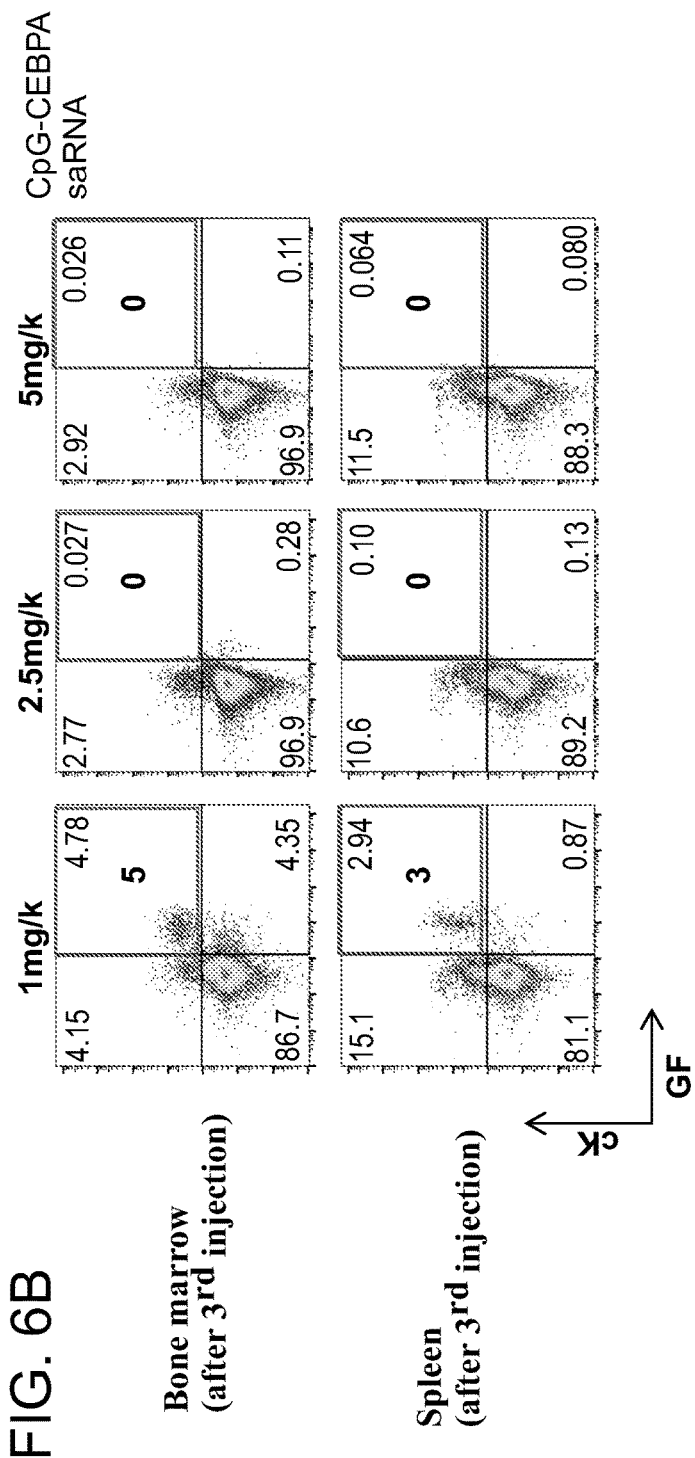
Figure 7A:
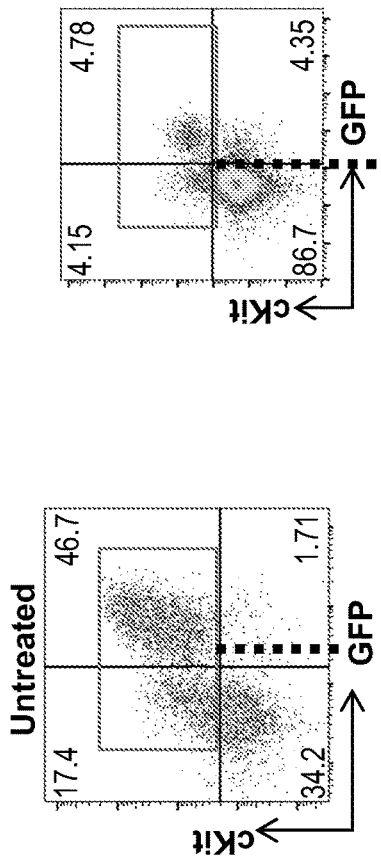
FIGS. 7A-7B show flow cytometry and histrograms data of intravenous injection of CpG-CEBPA saRNA inducing target gene expression in AML cells in the bone marrow. Mice with established Cbfb/MYH11/Mpl leukemia were injected three times every other day using 1 mg/kg of CpG-CEBPA saRNA and euthanized one day after last treatment.
Figure 7B:
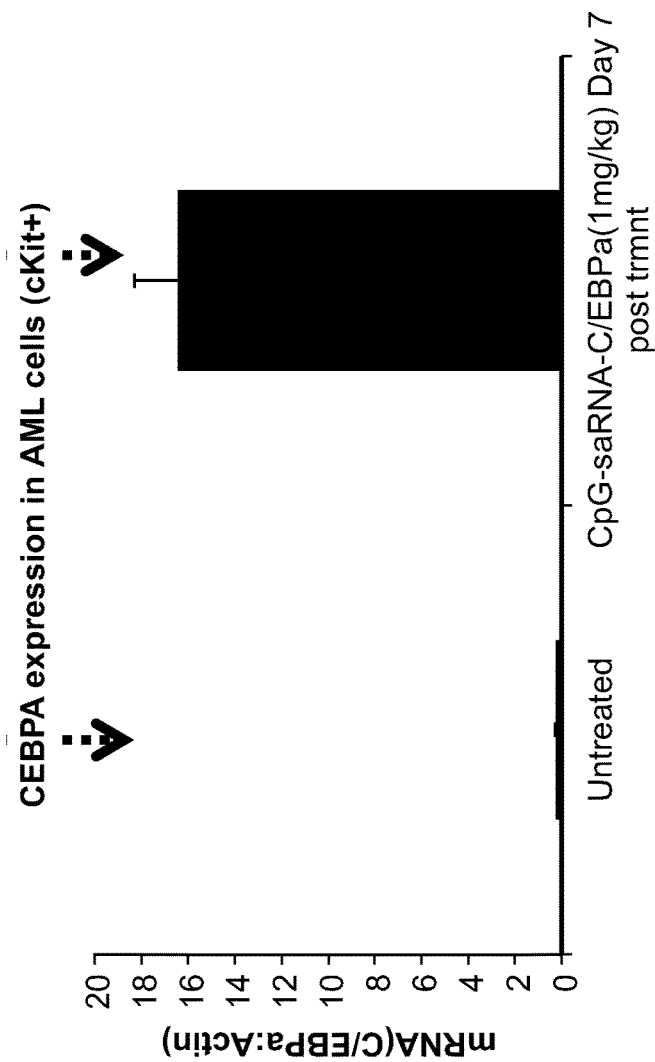
Figures 8A, 8B:
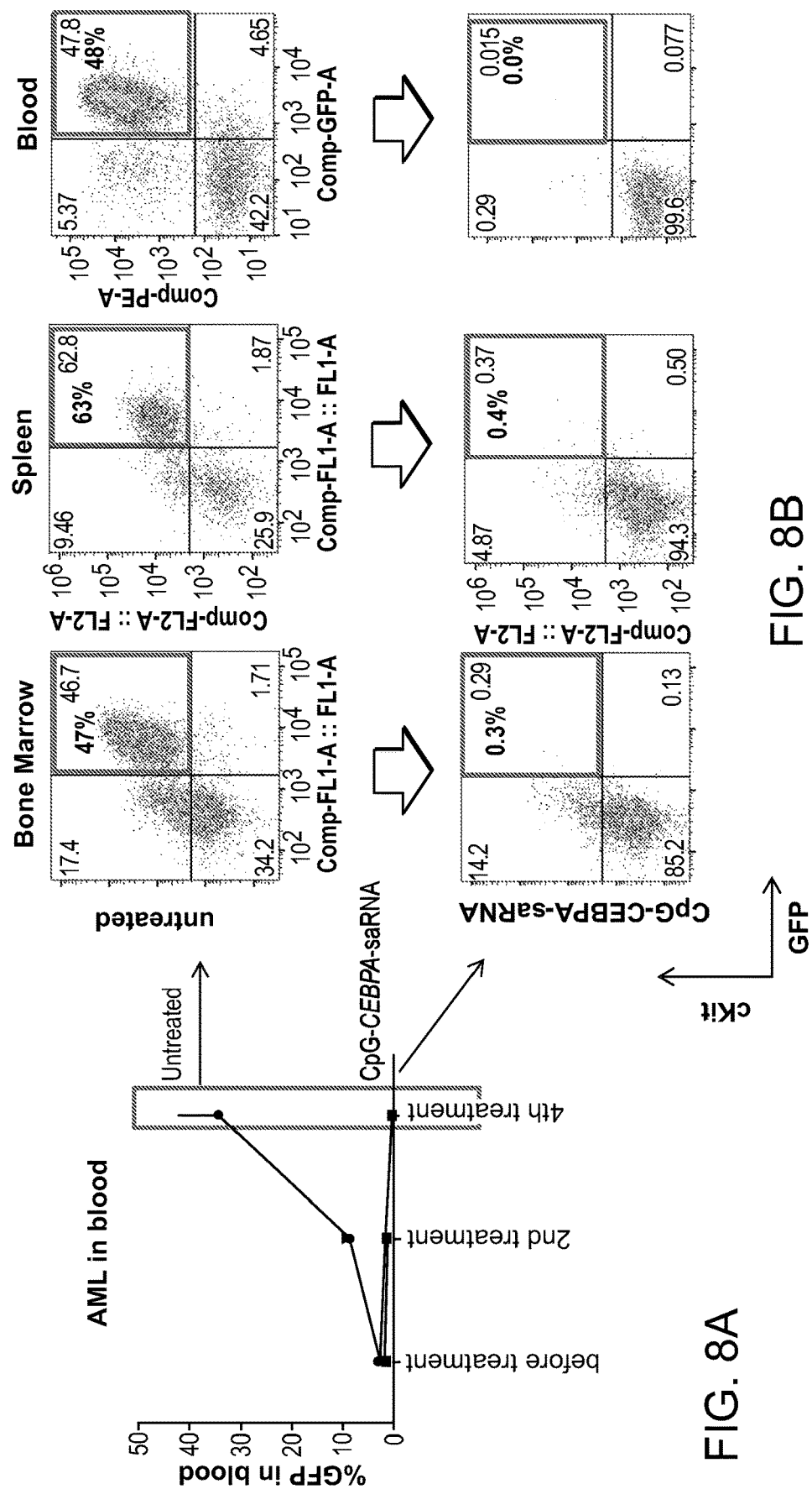
FIGS. 8A-8B show line graphs and flow cytometry data of intravenous injections of CpG-CEBPA saRNA induce target gene expression in AML cells in the bone marrow. Mice with established Cbfb/MYH11/Mpl leukemia were injected four times every other day using 5 mg/kg of CpG-CEBPA saRNA and euthanized one day after last treatment (day 20).

Provided herein, inter alia, is an isolated compound targeting moieties and antisense oligonucleotides. The isolated compounds include a phosphorothioated oligodeoxynucleotide (ODN) nucleic acid sequence conjugated to short-activating RNAs (saRNA) or an antisense oligonucleotide (ASO). The saRNA and/or the ASO may be modified with 2' OMe, locked nucleic acid. Also provided herein are compositions of the compounds disclosed herein, and method of treatment disease in a subject in need thereof with the disclosed compound or composition.

Definitions

The following definitions are included for the purpose of understanding the present subject matter and for constructing the appended patent claims. Abbreviations used herein have their conventional meaning within the chemical and biological arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this disclosure. The following definitions are provided to facilitate understanding of certain terms used frequently herein and are not meant to limit the scope of the present disclosure.

As used herein, the term "short activating RNAs (saRNAs)" is used according to its plain and ordinary meaning and refers to RNA that is capable of activating or inducing gene expression. Gene specific saRNAs target sequences in the promoter of a target gene and induce expression of the gene. In embodiments, the saRNA oligomer may be a double stranded oligomer of 15-30 bases. The saRNA oligomer may be partially double stranded, with single stranded overhangs (see, e.g., FIGS. 1A-1F). The double strand includes a guide strand (antisense, AS) and a passenger strand (sense strand, SS). In embodiments, the saRNA may target regions between nucleotides −75 to +25 relative to a transcription start site of a target gene. In embodiments, the oligomer may have a 2' chemical modification. In embodiments, the oligomer may have serum stability-enhancing chemical modification, e.g., a phosphothioate internucleotide linkage, a 2'-O-methyl ribonucleotide, a 2'-deoxy-2'fluoro ribonucleotide, a 2'-deoxy ribonucleotide, a universal base nucleotide, a 5-C methyl nucleotide, an inverted deoxybasic residue incorporation, or a locked nucleic acid.

As used herein antisense oligonucleotide (ASO) is used according to its plain and ordinary meaning and refers to an oligonucleotide that targets a transcript of a gene to reduce expression of the gene product. In embodiments, the antisense oligonucleotide is an anti-Gene X antisense oligonucleotide sequence. For example, an ASO of STAT can be referred to as an "anti-STAT antisense oligonucleotide sequence. Anti-STAT1 oligonucleotide is an oligonucleotide that reduces or inhibits translation level of messenger RNA (mRNA) of Signal transducer and activator of transcription 1 (STAT1) transcription factor, which in humans is encoded by the STAT1 gene. It is a member of the STAT protein family. Anti-STAT2 oligonucleotide is an oligonucleotide that reduces or inhibits translation level of messenger RNA (mRNA) of Signal transducer and activator of transcription 2 (STAT2). Anti-STAT3 oligonucleotide is an oligonucleotide that reduces or inhibits translation level of messenger RNA (mRNA) of Signal transducer and activator of transcription 3 (STAT3). Anti-STAT4 oligonucleotide is an oligonucleotide that reduces or inhibits translation level of messenger RNA (mRNA) of Signal transducer and activator of transcription 4 (STAT4). Anti-STAT5A oligonucleotide is an oligonucleotide that reduces or inhibits translation level of messenger RNA (mRNA) of Signal transducer and activator of transcription 5A (STAT5A). Anti-STAT5B oligonucleotide is an oligonucleotide that reduces or inhibits translation level of messenger RNA (mRNA) of Signal transducer and activator of transcription 5B (STAT5B). Anti-STAT6 oligonucleotide is an oligonucleotide that reduces or inhibits translation level of messenger RNA (mRNA) of Signal transducer and activator of transcription 6 (STAT6).

In embodiments, the oligomer may have a 2' chemical modification. In embodiments, the oligomer may have serum stability-enhancing chemical modification, e.g., a phosphothioate internucleotide linkage, a 2'-O-methyl ribonucleotide, a 2'-deoxy-2'fluoro ribonucleotide, a 2'-deoxy ribonucleotide, a universal base nucleotide, a 5-C methyl nucleotide, an inverted deoxybasic residue incorporation, or a locked nucleic acid (LNA).

As used herein, the term "phosphorothioated oligodeoxynucleotide ("ODN")" refers to a nucleic acid sequence, e.g., "CpG nucleic acid sequence", "GpC nucleic acid sequence" or "PS (phosphorothioated) nucleic acid sequence" in which some or all the internucleotide linkages constitute a phosphorothioate linkage. In embodiments, phosphorothioated oligodeoxynucleotide (ODN) is 15 to 30 bases long, single-stranded, and/or partly or completely phosphorothioated. The partly phosphorothioated ODN may be an ODN in which 1, 2, 3, 4, 5, 6, 7, 8, 9, 10, 11, 12, 13, 14, 15, 16, 17, 18, 19, 20, 21, 22, 23, 24, 25, 26, 27, or 28, internucleotide linkages constitute a phosphorothioate linkage. Within a sequence, phosphorothioation can be in string on 2, 3, 4, 5, 6, 7, 8, 9, 10, 11, 12, 13, 14, 15, or all nucleotides. In embodiments, some oligodeoxynucleotides are not phosphorothioated.

As used herein, the term "CpG nucleic acid sequence" refers to nucleic acid including a CpG motif in which a 5' C nucleotide connected to a 3' G nucleotide through a phosphodiester internucleotide linkage or a phosphodiester derivative internucleotide linkage. In embodiments, a CpG motif includes a phosphodiester internucleotide linkage. In embodiments, a CpG motif includes a phosphodiester derivative internucleotide linkage. In embodiments, a CpG motif includes a phosphorothioate linkage.

As used herein, the term "GpC nucleic acid sequence" refers to nucleic acid including a GpC motif in which a 5' G nucleotide connected to a 3' C nucleotide through a phosphodiester internucleotide linkage or a phosphodiester derivative internucleotide linkage. In embodiments, a GpC motif includes a phosphodiester internucleotide linkage. In embodiments, a GpC motif includes a phosphodiester derivative internucleotide linkage. In embodiments, a GpC motif includes a phosphorothioate linkage.

As used herein, the term "fully phosphorothioated ODN" refers to an oligonucleotide (e.g., CpG-ODN or GpC-ODN) in which all internuclotide linkage are phosphorothioate linkages.

As used herein, the term "Class A CpG ODN" or "A-class CpG ODN" or "D-type CpG ODN" or "Class A CpG DNA sequence" is used in accordance with its common meaning in the biological and chemical sciences and refers to a CpG motif including oligodeoxynucleotide having one or more of a poly-G sequence at the 5', 3', or both ends; an internal palindrome sequence including CpG motif; having one or more phosphodiester derivatives linking deoxynucleotides. In embodiments, a Class A CpG ODN includes poly-G sequence at the 5', 3', or both ends; an internal palindrome sequence including CpG motif; and one or more phosphodiester derivatives linking deoxynucleotides. In embodiments, the phosphodiester derivative is phosphorothioate. Examples of Class A CpG ODNs include ODN D19, ODN 1585, ODN 2216, and ODN 2336.

As used herein, the term "Class B CpG ODN" or "B-class CpG ODN" or "K-type CpG ODN" or "Class B CpG DNA sequence" is used in accordance with its common meaning in the biological and chemical sciences and refers to a CpG motif including oligodeoxynucleotide including one or more of a 6 mer motif including a CpG motif; phosphodiester derivatives linking all deoxynucleotides. In embodiments, a Class B CpG ODN includes one or more copies of a 6 mer motif including a CpG motif and phosphodiester derivatives linking all deoxynucleotides. In embodiments, the phosphodiester derivative is phosphorothioate. In embodiments, a Class B CpG ODN includes one 6 mer motif including a CpG motif. In embodiments, a Class B CpG ODN includes two copies of a 6 mer motif including a CpG motif. In embodiments, a Class B CpG ODN includes three copies of a 6 mer motif including a CpG motif. In embodiments, a Class B CpG ODN includes four copies of a 6 mer motif including a CpG motif. Examples of Class B CpG ODNs include ODN 1668, ODN 1826, ODN 2006, and ODN 2007.

As used herein, the term "Class C CpG ODN" or "C-class CpG ODN"" or "C-type CpG DNA sequence" is used in accordance with its common meaning in the biological and chemical sciences and refers to an oligodeoxynucleotide including a palindrome sequence including a CpG motif and phosphodiester derivatives (phosphorothioate) linking all deoxynucleotides. Examples of Class C CpG ODNs include ODN 2395 and ODN M362.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —C—H=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$ R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2m'+1), where m' is the total number of carbon atoms in such radical. R, R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond (s), polar bond(s), or combinations or mixtures thereof).

Furthermore, it will be appreciated by one of ordinary skill in the art that the synthetic methods, as described herein, utilize a variety of protecting groups. As used herein, the term "protected reactive group" refers to a particular functional moiety (e.g., oxygen, sulfur, nitrogen and carbon) that is temporarily blocked so that a reaction can be carried out selectively at another reactive site in a multifunctional compound. Protecting groups may be introduced and removed at appropriate stages during the synthesis of a compound using methods that are known to one of ordinary skill in the art. The protecting groups are applied according to standard methods of organic synthesis as described in the literature (see, e.g.: Theodora W. Green and Peter G. M. Wuts (2007) Protecting Groups in Organic Synthesis, 4th edition, John Wiley and Sons; R. Larock, Comprehensive Organic Transformations, VCH Publishers (1989); Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995); each of which is incorporated by reference with respect to protecting groups). Certain exemplary protecting groups are detailed herein, however, it will be appreciated that the present invention is not intended to be limited to these protecting groups; rather, a variety of additional equivalent protecting groups may be utilized according to methods known to one skilled in the art.

Exemplary alcohol protecting groups include, but are not limited to, methyl ethers, substituted methyl ethers (e.g., MOM (methoxymethyl ether), MTM (methylthiomethyl ether), BOM (benzyloxymethyl ether), PMBM (p-methoxybenzyloxymethyl ether), optionally substituted ethyl ethers, optionally substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), esters (e.g., formate, acetate, benzoate (Bz), trifluoroacetate, dichloroacetate) carbonates, cyclic acetals and ketals. In embodiments, a hydroxy group may be protected as an ether (—OR*) or an ester (—OC(=O)R*), where R* is substituted or unsubstituted alkyl, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), or substituted or unsubstituted heteroaryl. Exemplary protected hydroxyl groups include hydroxyls protected as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$ or —OAc).

Exemplary amino protecting groups include, but are not limited to, carbamates (including methyl carbamate, ethyl carbamate, substituted ethyl carbamates (e.g., Troc), t-butyl carbamate (Boc), and benzyl carbamate (Cbz)), amides, cyclic imide derivatives, N-alkyl and N-aryl amines, imine derivatives, enamine derivatives, and the like. For example, protected amino groups include nitrogen groups protected as: an amide (—NR*C(=O)R*) or as a carbamate (—NR*C(=O)OR*), where each R* is, independently, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), or substituted or unsubstituted heteroaryl. In embodiments, a protected amino group is, for example: a methyl amide (—NHC(=O)CH$_3$); a benzyl carbamate (—NHC(=O)OCH$_2$C$_6$H$_5$); as a t-butyl carbamate (—NHC(=O)OC(CH$_3$)$_3$); a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

Exemplary sulfhydryl protecting groups include, but are not limited to thioethers (—SR*), where R* is substituted or unsubstituted alkyl, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), or substituted or unsubstituted heteroaryl. In embodiments, a protected sulfhydryl group is, for example: a substituted or unsubstituted benzyl thioether, a tert-butyl thioether, a 4-methylbenzyl thioether, a trityl thioether, a 2-(trimethylsilyl)ethyl (TMSE) thioether, a 2-cyanoethyl thioether, a 9-fluorenylmethyl (Fmoc) thioether, or an acetamidomethyl ether (—SCH$_2$NHC(=O)CH$_3$).

In embodiments, the click chemistry reactive group is or includes an azide groups, an alkene group, an amino groups, an N-hydroxysuccinimide group, a sulfhydryl group, a divinyl sulfone derivative, or a maleimido derivative. Thus, in embodiments, the linker is substituted with a reactive group (e.g. a click chemistry reactive group) or a protected reactive group, including, for example, a protected amino group or a N-hydroxysuccinimide group, suitable for conjugation by N-hydroxysuccinimide (NHS) chemistry; a sulfhydryl group that may be conjugated with divinyl sulfone; a protected sulfhydryl group, which may be conjugated with 1-alkyl-3-methylacryloyl (acryloyl) chloride or acryloyl derivatives; a protected sulfhydryl group, which may be conjugated with maleimido derivatives.

A "label" or a "detectable moiety" is a composition detectable by spectroscopic, photochemical, biochemical, immunochemical, chemical, magnetic resonance imaging, or other physical means. For example, useful detectable moieties include $^{32}$P, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline SPIO, monochrystalline SPIO aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable moieties also include any of the above compositions encapsulated in nanoparticles, particles, aggregates, coated with additional compositions, derivatized for binding to a targeting agent (e.g. compound described herein). Any method known in the art for conjugating an oligonucleotide or protein to the label may be employed, e.g., using methods described in Hermanson, *Bioconjugate Techniques* 1996, Academic Press, Inc., San Diego.

The term "cell" as used herein also refers to individual cells, cell lines, or cultures derived from such cells. A "culture" refers to a composition comprising isolated cells of the same or a different type.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

"Patient," "subject," "patient in need thereof," and "subject in need thereof" are herein used interchangeably and refer to a living organism suffering from or prone to a disease or condition that can be treated by administration using the methods and compositions provided herein. Non-limiting examples include humans, other mammals, bovines, rats, mice, dogs, monkeys, goat, sheep, cows, deer, and other non-mammalian animals. In some embodiments, a patient is human. Tissues, cells and their progeny of a biological entity obtained in vitro or cultured in vitro are also contemplated.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

The term "inhibiting" also means reducing an effect (disease state or expression level of a gene/protein/mRNA) relative to the state in the absence of a compound or composition of the present disclosure.

A "test compound" as used herein refers to an experimental compound used in a screening process to identify activity, non-activity, or other modulation of a particularized biological target or pathway.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Disease" or "condition" refer to a state of being or health status of a patient or subject capable of being treated with the compounds or methods provided herein. In some instances, "disease" or "condition" refers to a "cancer".

As used herein, the term "cancer" refers to all types of cancer, neoplasm, malignant or benign tumors found in mammals, including leukemia, carcinomas and sarcomas. Exemplary cancers include breast cancer, ovarian cancer, colon cancer, liver cancer, kidney cancer and pancreatic cancer. Additional examples include leukemia (e.g. acute myeloid leukemia ("AML") or chronic myelogenous leukemia ("CML")), cancer of the brain, lung cancer, non-small cell lung cancer, melanoma, sarcomas, and prostate cancer, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture. In some embodiments contacting includes allowing a compound described herein to interact with a protein or enzyme.

The terms "phenotype" and "phenotypic" as used herein refer to an organism's observable characteristics such as onset or progression of disease symptoms, biochemical properties, or physiological properties.

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual*, 18.7-18.88). When used in reference to polypeptides, expression includes any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "an amount of" in reference to a polynucleotide or polypeptide, refers to an amount at which a component or element is detected. The amount may be measured against a control, for example, wherein an increased level of a particular polynucleotide or polypeptide in relation to the control, demonstrates enrichment of the polynucleotide or polypeptide. Thus, in embodiments, an increased amount indicates a greater level or efficiency of grafting HSPCs described herein into a host (e.g. mouse). The term refers to quantitative measurement of the enrichment as well as qualitative measurement of an increase or decrease relative to a control.

Throughout the description and claims of this specification the word "comprise" and other forms of the word, such as "comprising" and "comprises," means including but not limited to, and is not intended to exclude, for example, other components.

"Analog," "analogue," or "derivative" is used in accordance with its plain ordinary meaning within Chemistry and Biology and refers to a chemical agent that is structurally similar to another agent (i.e., a so-called "reference" agent) but differs in composition, e.g., in the replacement of one atom by an atom of a different element, or in the presence of a particular functional group, or the replacement of one functional group by another functional group, or the absolute stereochemistry of a chiral center of the reference agent. In some embodiments, a derivative may be a conjugate with a pharmaceutically acceptable agent, for example, phosphate or phosphonate.

As used herein, the term "salt" refers to acid or base salts of the agents used herein. Illustrative but non-limiting examples of acceptable salts are mineral acid (hydrochloric acid, hydrobromic acid, phosphoric acid, sulfuric acid, and the like) salts, organic acid (acetic acid, propionic acid, glutamic acid, citric acid, and the like) salts, and quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

An "adjuvant" (from Latin, adiuvare: to aid) is a pharmacological and/or immunological agent that modifies the effect of other agents.

A "diluent" (also referred to as a filler, dilutant or thinner) is a diluting agent. Certain fluids are too viscous to be pumped easily or too dense to flow from one particular point to the other. This can be problematic, because it might not be economically feasible to transport such fluids in this state. To ease this restricted movement, diluents are added. This decreases the viscosity of the fluids, thereby also decreasing the pumping/transportation costs.

The terms "administration" or "administering" refer to the act of providing an agent of the current embodiments or pharmaceutical composition including an agent of the current embodiments to the individual in need of treatment.

By "co-administer" it is meant that a composition described herein is administered at the same time, just prior to, or just after the administration of additional therapies. The compound or the composition of the disclosure can be administered alone or can be co-administered to the patient. Co-administration is meant to include simultaneous or sequential administration of the compound individually or in combination (more than one compound or agent). The preparations can also be combined, when desired, with other active substances (e.g. to reduce metabolic degradation).

As used herein, "sequential administration" includes that the administration of two agents (e.g., the compounds or compositions described herein) occurs separately on the same day or do not occur on a same day (e.g., occurs on consecutive days).

As used herein, "concurrent administration" includes overlapping in duration at least in part. For example, when two agents (e.g., any of the agents or class of agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and. Other modes of delivery include, but are not limited to, the use of liposomal formulations, intravenous infusion, transdermal patches, etc.

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Bioniater Sci. Polym. Ed.* 7:623-645, 1995; as biodegradable and injectable gel formulations (see, e.g., Gao *Phann. Res.* 12:857-863, 1995); or, as microspheres for oral administration (see, e.g., Eyles, *J. Phann. Pharmacol.* 49:669-674, 1997).

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compositions/formulations of this disclosure can be administered as frequently as necessary to achieve a therapeutic amount.

Pharmaceutical compositions may include compositions wherein the therapeutic drug (e.g., agents described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of therapeutic drug effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and agents of this disclosure. Adjustment and manipulation of established dosages (e.g., frequency and duration) are well within the ability of those skilled in the art.

For any therapeutic agent described herein, the therapeutically effective amount can be initially determined from cell culture assays. Target concentrations will be those concentrations of therapeutic drug(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring agent's effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the therapeutic drug being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the agent. Thereafter, the dosage is increased by small increments until the optimum effect under circumstances is reached. Dosage amounts and intervals can be adjusted individually to provide levels of the administered agent effective for the particular clinical indication being treated. This will provide a therapeutic regimen that is commensurate with the severity of the individual's disease state.

A weight percent of a component, unless specifically stated to the contrary, is based on the total weight of the formulation or composition in which the component is included.

"Excipient" is used herein to include any other agent that may be contained in or combined with a disclosed agent, in which the excipient is not a therapeutically or biologically active agent/agent. As such, an excipient should be pharmaceutically or biologically acceptable or relevant (for example, an excipient should generally be non-toxic to the individual). "Excipient" includes a single such agent and is also intended to include a plurality of excipients. For the purposes of the present disclosure the term "excipient" and "carrier" are used interchangeably in some embodiments of the present disclosure and said terms are defined herein as, "ingredients which are used in the practice of formulating a safe and effective pharmaceutical composition."

The term "about" refers to any minimal alteration in the concentration or amount of an agent that does not change the efficacy of the agent in preparation of a formulation and in treatment of a disease or disorder. The term "about" with respect to concentration range of the agents (e.g., therapeutic/active agents) of the current disclosure also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Compound

In one aspect, the present disclosure includes an isolated compound including a phosphorothioated oligodeoxynucleotide (ODN), conjugated to an antisense nucleic acid sequence or to a short-activating RNA (saRNA) of a gene of interest. In embodiments, the phosphorothioated ODN is a 15 to 30 bases long, single-stranded, partly or completely phosphorothioated oligodeoxynucleotide. In embodiments, the isolated compound has the formula: PODN-L-ANA (I) or PODN-L-saRNA (II). In Formula (I) and (II), PODN is the phosphorothioated ODN and L is a linker such as a covalent linker. In Formula (I), ANA is the antisense nucleic acid sequence. In Formula (II), saRNA is the short-activating RNA.

In embodiments, the isolated compound includes a nucleic acid sequence having about 80%-100% sequence identity with a continuous 15 nucleobase sequence of one of phosphorothioated oligodeoxynucleotides (ODN) having a sequence of SEQ ID NOs: 7-18, 29-30, and 98-101, conjugated to an antisense oligonucleotide (ASO). In embodiments, the present disclosure provides an isolated compound including a nucleic acid sequence having about 80%-100% sequence identity with a continuous 15 nucleobase sequence of one of phosphorothioated oligodeoxynucleotides (ODN) having a sequence of SEQ ID NOs: 7-18, 29-30, and 98-101, conjugated to a saRNA. In embodiments, the nucleic acid sequence having about 80%-100% sequence identity with a continuous 15 nucleobase sequence of one of phosphorothioated oligodeoxynucleotides (ODN) having a sequence of SEQ ID NOs: 7-18, 29-30, and 98-101, includes a 15 to 30 bases long, single-stranded, partly or completely phosphorothioated oligonucleotide conjugated to a saRNA or an ASO. In embodiments, the antisense oligonucleotide is a STAT (STAT1-STAT6) antisense oligonucleotide. In embodiments, the antisense oligonucleotide is a STAT-3 antisense oligonucleotide. In embodiments, the saRNA is a saRNA of CEBP/α, p21, or p53.

In embodiments, the isolated compound of the present disclosure includes a nucleic acid sequence having about 80-85%, about 85-90%, about 90-95%, about 95%-100% sequence identity with a continuous 15 nucleobase sequence of one of phosphorothioated oligodeoxynucleotides (ODN) having a sequence of SEQ ID NOs: 7-18, 29-30, and 98-101, conjugated to a saRNA or an antisense oligonucleotide (ASO). In embodiments, the nucleic acid sequence having about 80-85%, about 85-90%, about 90-95%, about 95%-100% sequence identity with a continuous 15 nucleobase sequence of one of phosphorothioated oligodeoxynucleotides (ODN) having a sequence of SEQ ID NOs: 7-18, 29-30, and 98-101 includes a 15 to 30 bases long, single-stranded, partly or completely phosphorothioated oligonucleotide conjugated to a saRNA or an antisense oligonucleotide (ASO).

The present disclosure provides an isolated compound including a phosphorothioated oligodeoxynucleotide (ODN) having a sequence of SEQ ID NOs: 7-18, 29-30, and 98-101 conjugated to a short-activating RNA (saRNA) or an ASO. In embodiments, the present disclosure includes a phosphorothioated oligodeoxynucleotide (ODN) having a sequence of SEQ ID NOs: 7-18, 29-30, and 98-101 conjugated to a short-activating RNA (saRNA) that is capable of activating a CCAAT/enhancer-binding protein-α (C/EBPα).

In embodiments, the disclosure provides a phosphorothioated oligodeoxynucleotide (ODN) having a sequence of SEQ ID NOs: 7-18, 29-30, and 98-101 conjugated to a saRNA or an ASO with a linker between the phosphorothioated oligodeoxynucleotide (ODN) having a sequence of SEQ ID NOs: 7-18, 29-30, and 98-101, and the saRNA or the ASO. The linker may be a covalent linker. In embodiments, the linker is or includes a substituted or unsubstituted alkylene or heteroalkylene linker. In embodiments, the nucleic acid conjugated to saRNA includes more than one substituted or unsubstituted heteroalkylene linkers. Linkers may be added during the synthesis in sequence. In embodiments, heteroalkylene linkers are connected to each other with an intervening phosphate bond.

In embodiments, the linker is a substituted or unsubstituted heteroalkylene or substituted or unsubstituted cyclo-heteroalkylene. A "cyclo-heteroalkylene," as used herein is a heteroalkylene having a one or more divalent cyclic moieties within the heteroalkylene chain. The cyclic moiety may be a substituted or unsubstituted cycloalklylene, substituted or unsubstituted heterocycloalkylene, substituted or unsubstituted arylene or substituted or unsubstituted heteroarylene. In embodiments, the cyclic moiety is a substituted or unsubstituted ribose (e.g., a nucleoside). In embodiments, the cyclic moiety serves as a branch point of the linker thereby forming a branched linker. The cyclic moiety branch point may be used to attach additional functional moieties to the conjugates provided herein, such as detectable moieties, drug moieties or biomolecule. As explained in more detail below, the additional functional moieties may be connected using click chemistry techniques as known in the art.

In embodiments, the linker (e.g., L in Formula (I) and (II)) is or contains a moiety having the formula:

—(CH$_2$)$_n$—PO$_4$—[(CH$_2$)$_n$—PO$_4$]$_z$—(CH$_2$)$_n$—.

In the formula above, the symbol n is an integer from 1 to 5 (e.g., 3) and the symbol z is an integer from 0 to 50 (e.g. from 0 to 25, 0 to 10, or 0 to 5). In embodiments, n is 3 and z is 0 to 5 or 1 to 5. In embodiments, n is 3 and z is 0 to 4 or 1 to 4. In embodiments, n is 3 and z is 0 to 3 or 1 to 3. In embodiments, n is 3 and z is 3.

In embodiments, the linker (e.g., L in Formula (I) and (II)) is or contains a moiety having the formula:

—(CH$_2$)$_{n1}$—PO$_4$—[(CH$_2$)$_{n2}$—PO$_4$]$_z$—(CH$_2$)$_{n3}$—.

In the formula above, the symbols n1, n2 and n3 are independently an integer from 1 to 5 (e.g., 3) and the symbol z is an integer from 0 to 50 (e.g. from 0 to 25, 0 to 10, or 0 to 5). In embodiments, n1, n2 and n3 are 3 and z is 0 to 5 or 1 to 5. In embodiments, n1, n2 and n3 are 3 and z is 0 to 4 or 1 to 4. In embodiments, n1, n2 and n3 are 3 and z is 0 to 3 or 1 to 3. In embodiments, n1, n2 and n3 are 3 and z is 3.

For example, the linker may have the structure below, where the linker connects with the 3' phosphate of the guanine on one end and the 5' phosphate of the thymidine on the other end:

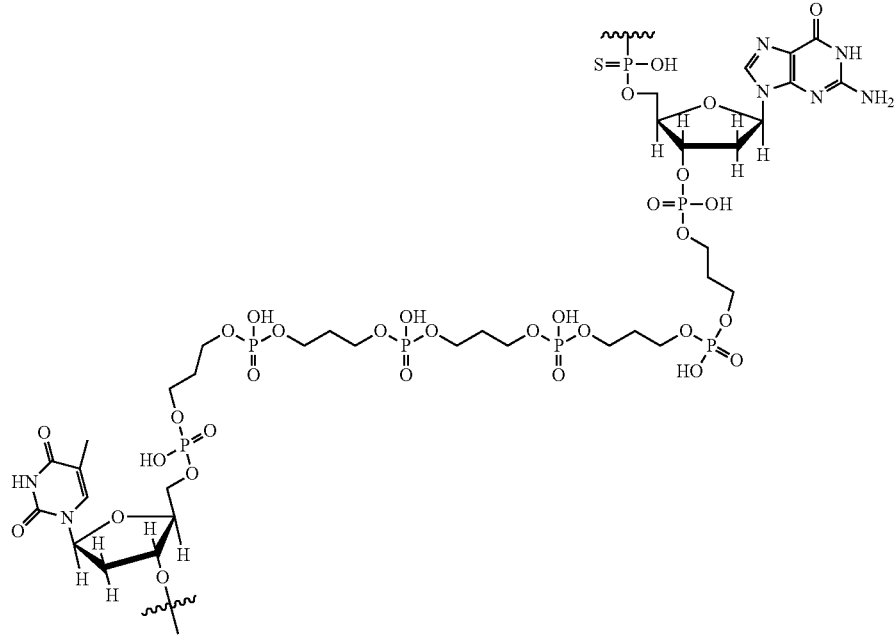

A person having ordinary skill in the art will immediately understand that the guanine and thymidine in the above structure may be replaced with any nucleic acid monomer/nucleobase.

In embodiments, the linker comprises a heteroalkylene having three carbons (—OCH$_2$CH$_2$CH$_2$O—) conjugated to a phosphate moiety. The heteroalkylene moiety can be varied (e.g., the linker can comprise a heteroalkyene having two, four, five, six, seven, or eight carbons).

In embodiments, the guanosine above is connected to the ODN nucleic acid sequence and the thymidine is connected to the short-activating RNA (saRNA) or an ASO.

In embodiments, the linker (e.g., linker may be an heteroalkylene linker) may be substituted with a reactive group (e.g. a click chemistry reactive group) or a protected reactive group. The reactive group may be used to conjugate the phosphorothioated oligodeoxynucleotide (ODN)-saRNA/ASO compound to an additional functional moiety as described herein, such as a detectable moiety or biomolecule (e.g. a targeting moiety).

Thus, the heteroalkylene linker may include further modification, conjugation, or attachment of additional moieties.

The reactive group used to conjugate the phosphorothioated oligodeoxynucleotide (ODN)-saRNA/ASO compound to an additional functional moiety may be any applicable reactive group useful in bioconjugate chemistry. See Hermanson, *Bioconjugate Techniques* 1996, Academic Press, Inc., San Diego.

In embodiments, the reactive group is a click chemistry reactive group. Click chemistry refers to a group of reactions that are fast, simple to use, easy to purify, versatile, regio-specific, and give high product yields. In embodiments, four different click reactions are possible: (1) Cycloadditions—these primarily refer to 1,3-dipolar cycloadditions, but also include hetero-Diels-Alder cycloadditions; (2) Nucleophilic ring-openings—these refer to the opening of strained heterocyclic electrophiles, such as aziridines, epoxides, cyclic sulfates, aziridinium ions, episulfonium ions; (3) carbonyl chemistry of the non-aldol type—examples include the formations of ureas, thioureas, hydrazones, oxime ethers, amides, aromatic heterocycles; (4) additions of carbon-carbon multiple bonds—examples include epoxidations, aziridinations, dihydrooxylations, sulfenyl halide additions, nitrosyl halide additions, and certain Michael additions. In embodiments, the click reaction used may be Cu$^I$-catalyzed Huisgen 1,3-dipolar cycloaddition (HDC) of azides or terminal alkynes to form 1,2,3-triazoles. In embodiments, the click reaction may be a copper-free reaction.

In embodiments, the click chemistry reactive group is or includes an azide group, an alkene group, an amino groups, an N-hydroxysuccinimide group, a sulfhydryl group, a divinyl sulfone derivative, or a maleimido derivative. Thus, in embodiments, the linker is substituted with a reactive group (e.g. a click chemistry reactive group) or a protected reactive group, including, for example, a protected amino group or a N-hydroxysuccinimide group, suitable for conjugation by N-hydroxysuccinimide (NHS) chemistry; a sulfhydryl group that may be conjugated with divinyl sulfone; a protected sulfhydryl group, which may be conjugated with 1-alkyl-3-methylacryloyl (acryloyl) chloride or acryloyl derivatives; a protected sulfhydryl group, which may be conjugated with maleimido derivatives.

Provided below is a structural example of a cyclo-heteroalkylene branched linker:

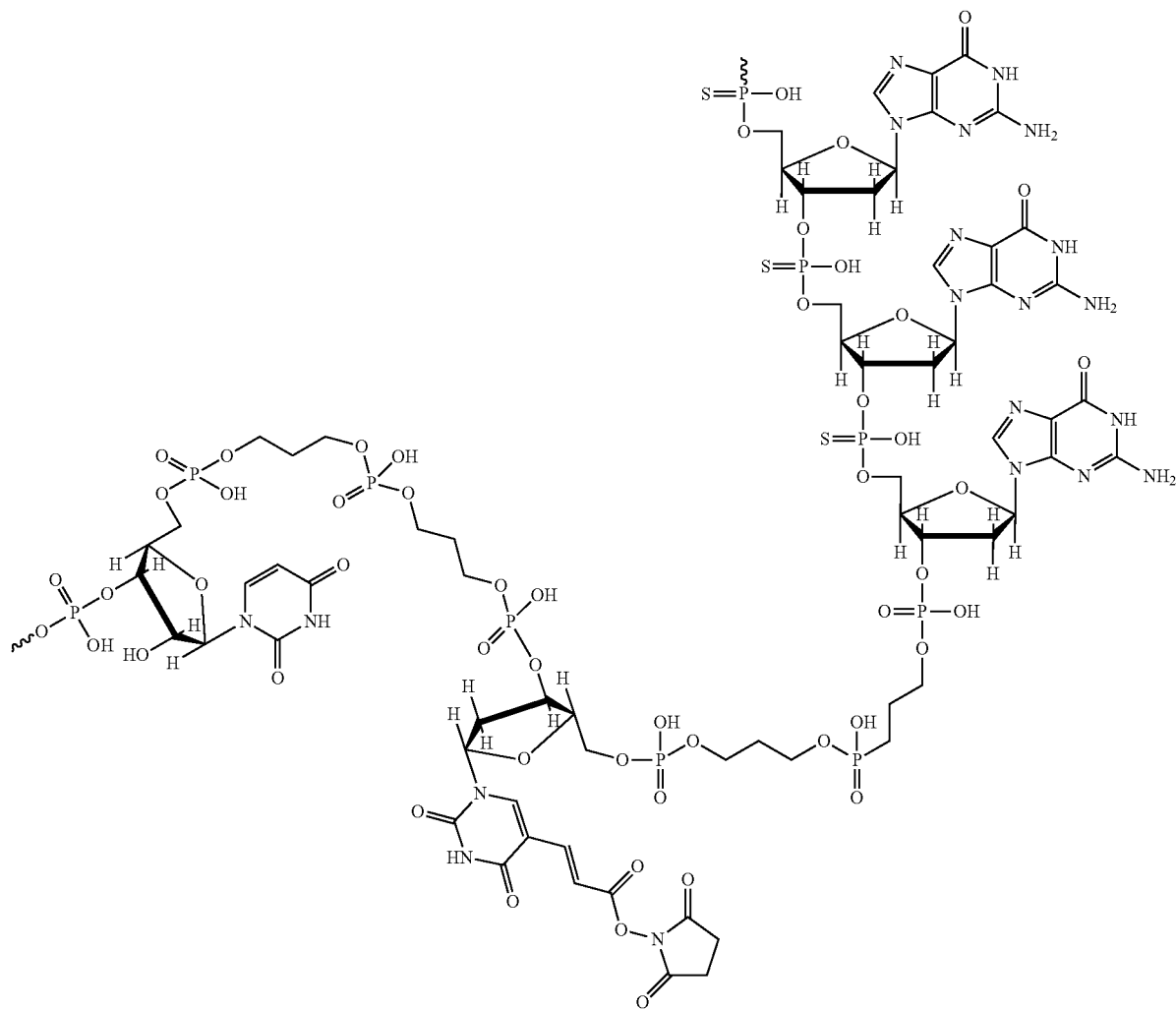

Substitution with NHS-Carboxy-dT
NHS esters react with nucleofiles such as amines.
NHS ester can be used for the introductions of the substituent such as PEG (reaction with PEG-amine)

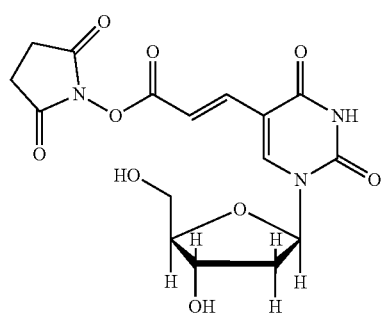

NHS-Carboxy-dT

As shown above, a cyclo-heteroalkylene branched linker connects with the 3' phosphate of the guanine on one end and the 5' phosphate of the thymidine on the other end. The moiety of the cyclo-heteroalkylene branched linker is a branch point and is a 5-substituted thymidine. The thymidine is substituted in position 5 with a reactive group containing an NHS moiety, which can serve as a reactive group to connect to an additional functional moiety.

Additional examples of compounds that can be used to serve as moiety branch points containing reactive functional groups and protected reactive functional groups are provided below.

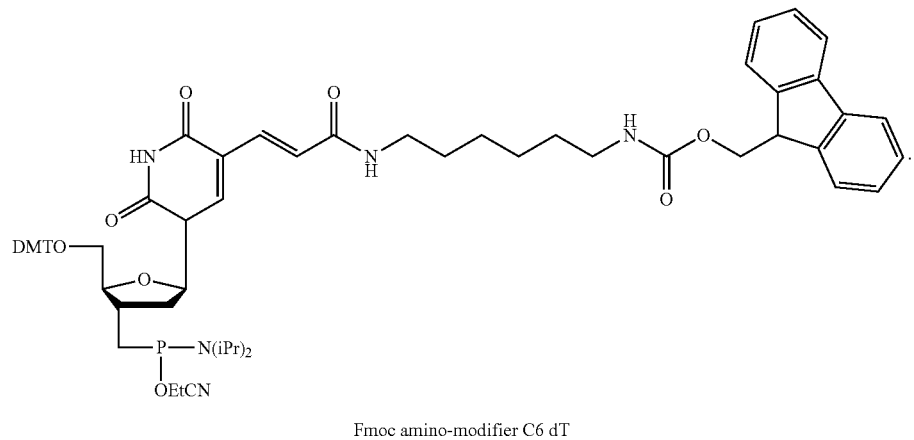

Fmoc amino-modifier C6 dT

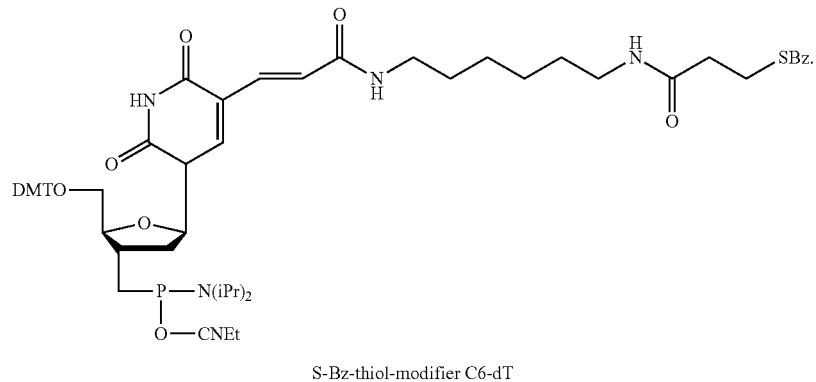

S-Bz-thiol-modifier C6-dT

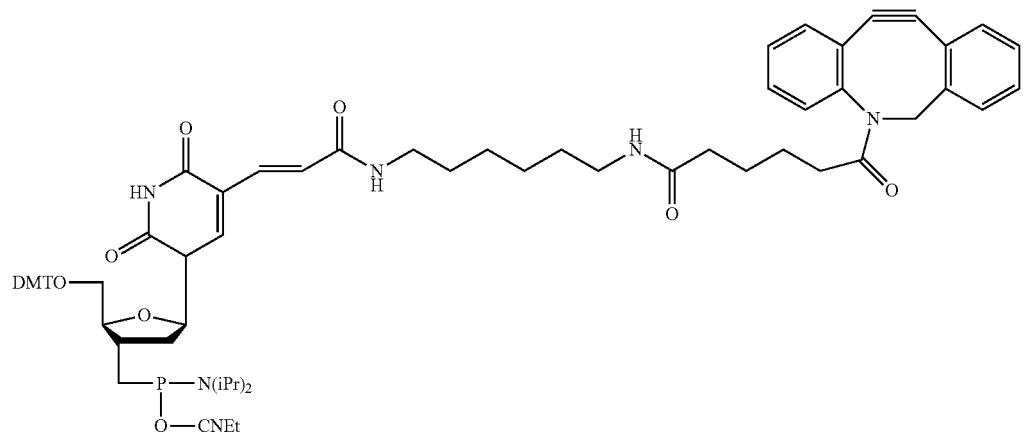

DBCO-dT

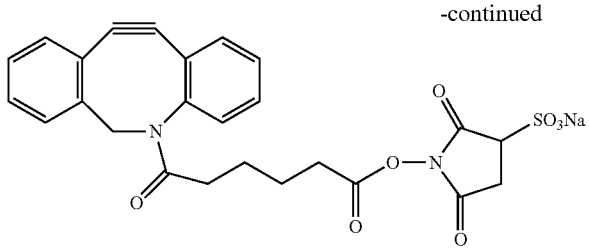

DBCO-sulfo-NHS Ester

In embodiments, the linker branch point may be non-cyclic. An example of a compound that can be used to serve as non-cyclic moiety branch point within the linker that contains a reactive functional group and protected reactive functional groups is provided below.

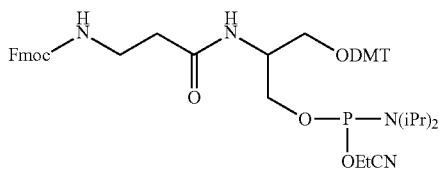

As set forth above, the reactive group may be used to conjugate the phosphorothioated oligodeoxynucleotide (ODN)-saRNA/ASO compound to an additional functional moiety such as a detectable moiety, therapeutic moiety (e.g. drug moiety), targeting moiety or biomolecule. Additional functional moieties include a fluorescent label, a targeting compound (bone targeting bisphosphonates), a drug, or an antibody. In embodiments, additional moiety is a chemically reactive moiety, detectable moiety, therapeutic moiety (e.g. anti-cancer agent or anti-viral agent), nucleic acid sequence, DNA sequence, or nucleic acid analogs. In embodiments, the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, an additional moiety is a therapeutic moiety (e.g. anti-cancer agent or anti-viral agent).

In embodiments, the additional functional moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the additional moiety is a substituted or unsubstituted $C_1$-$C_{40}$ alkyl, substituted or unsubstituted 2 to 40 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, the additional moiety is a substituted $C_1$-$C_{40}$ alkyl, substituted 2 to 40 membered heteroalkyl, substituted $C_3$-$C_8$ cycloalkyl, substituted 3 to 8 membered heterocycloalkyl, substituted $C_6$-$C_{10}$ aryl, or substituted 5 to 10 membered heteroaryl. In embodiments, the additional functional moiety is an $R^1$-substituted $C_1$-$C_{40}$ alkyl, $R^1$-substituted 2 to 40 membered heteroalkyl, $R^1$-substituted $C_3$-$C_8$ cycloalkyl, $R^1$-substituted 3 to 8 membered heterocycloalkyl, $R^1$-substituted $C_6$-$C_{10}$ aryl, or $R^1$-substituted 5 to 10 membered heteroaryl. In embodiments, the additional functional moiety is an $R^1$-substituted C1-$C_{40}$ alkyl. In embodiments, the additional functional moiety is an -(unsubstituted $C_1$-$C_{40}$ alkylene)-$R^1$. In embodiments, the additional functional moiety is an -(unsubstituted linear $C_1$-$C_{40}$ alkylene)-$R^1$. In embodiments, the additional functional moiety is an -(unsubstituted $C_3$-$C_{21}$ alkylene)-$R^1$. In embodiments, the additional functional moiety is an -(unsubstituted $C_3$-$C_{18}$ alkylene)-$R^1$. In embodiments, the additional functional moiety is an -(unsubstituted linear $C_3$-$C_{15}$ alkylene)-$R^1$. In embodiments, the additional functional moiety is an -(unsubstituted linear $C_6$-$C_{21}$ alkylene)-$R^1$. In embodiments, the additional functional moiety is an -(unsubstituted linear $C_9$-$C_{21}$ alkylene)-$R^1$. In embodiments, the additional functional moiety is an -(unsubstituted linear $C_9$-$C_{18}$ alkylene)-$R^1$. In embodiments, the additional functional moiety is an -(unsubstituted linear $C_9$-$C_{15}$ alkylene)-$R^1$. In embodiments, the additional functional moiety is an -(unsubstituted linear $C_{12}$-$C_{15}$ alkylene)-$R^1$. In embodiments, the additional functional moiety is an -(unsubstituted linear $C_{12}$ alkylene)-$R^1$. In embodiments, the additional functional moiety is an -(unsubstituted linear $C_{13}$ alkylene)-$R^1$. In embodiments, the additional functional moiety is an -(unsubstituted linear $C_{14}$ alkylene)-$R^1$. In embodiments, the additional functional moiety is an -(unsubstituted linear $C_{15}$ alkylene)-$R^1$. In embodiments, the additional functional moiety is an $R^1$-substituted 2 to 40 membered heteroalkyl. In embodiments, the additional functional moiety is an -(unsubstituted 2 to 40 membered heteroalkylene)-$R^1$. In embodiments, the additional functional moiety is a -(substituted linear 2 to 40 membered heteroalkylene)-$R^1$. In embodiments, the additional functional moiety is a -(substituted 5 to 40 membered heteroalkylene)-$R^1$. In embodiments, the additional functional moiety is a -(substituted 10 to 40 membered heteroalkylene)-$R^1$. In embodiments, the additional functional moiety is a -(substituted 15 to 40 membered heteroalkylene)-$R^1$. In embodiments, the additional functional moiety is a -(substituted 20 to 40 membered heteroalkylene)-$R^1$. In embodiments, the additional functional moiety is a -(substituted 30 to 40 membered heteroalkylene)-$R^1$. In embodiments, the additional functional moiety is a -(substituted 2 to 35 membered heteroalkylene)-$R^1$. In embodiments, the additional functional moiety is a -(substituted 2 to 30 membered heteroalkylene)-$R^1$. In embodiments, the additional functional moiety is a -(substituted 2 to 25 membered heteroalkylene)-$R^1$. In embodiments, the additional functional moiety is a -(substituted 2 to 20 membered heteroalkylene)-$R^1$. In embodiments, the additional functional moiety is a -(substituted 2 to 10 membered heteroalkylene)-$R^1$. In embodiments, the additional functional moiety is a -(substituted 2 to 50 membered heteroalkylene)-$R^1$. In embodiments, the additional functional moiety is a -(substituted 2 to 60 membered heteroalkylene)-$R^1$. In embodiments, the additional functional moiety is a substituted 2 to 40 membered heteroalkyl. In embodiments, the additional functional moiety is a substituted 10 to 50 membered heteroalkyl. In embodiments, the additional functional moiety is a substituted 20 to 40 membered heteroalkyl. In embodiments, the additional functional moiety is a substituted 25 to 40 membered heteroalkyl. In embodiments, the additional functional moiety is a substituted 30 to 40 membered heteroalkyl.

In embodiments, $R^1$ in an additional functional moiety is a detectable moiety or a therapeutic moiety. In embodiments, $R^1$ in an additional functional moiety is a detectable moiety. In embodiments, the detectable moiety is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, $R^1$ in an additional functional moiety is a therapeutic moiety (e.g. anti-cancer agent or anti-viral agent). In embodiments, $R^1$ in an additional functional moiety is H. In embodiments, an additional functional moiety is oxo. In embodiments, an additional functional moiety is oxygen. In embodiments, an additional functional moiety is sulfur. In embodiments, an additional functional moiety is =S.

In embodiments, the further linking substituent includes a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. The further linking substituent may include a PEG moiety attached to the reactive group or additional moiety.

In embodiments, the linker includes an unsubstituted $C_3$ alkylene (e.g. as described above separated by phosphate diester linker groups). In embodiments, the linker may be unsubstituted $C_{15}$ alkylene. In embodiments, the linker includes an unsubstituted $C_6$ to $C_{16}$ alkylene. In embodiments, the linker may be a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the linker may be a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the linker may be an unsubstituted $C_1$-$C_{40}$ alkylene, unsubstituted 2 to 40 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. The linker may be a substituted 2 to 40 membered heteroalkylene.

A linker may be a bond, nucleic acid sequence, two nucleic acid sequences, DNA sequence, two DNA sequences, nucleic acid analog sequence, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the linker is or contains a substituted or unsubstituted alkylene, substituted or unsubstituted heteroalkylene (e.g. substituted or unsubstituted alkylene groups connected by phosphate diester linker groups), substituted or unsubstituted cycloalkylene, substituted or unsubstituted heterocycloalkylene, substituted or unsubstituted arylene, or substituted or unsubstituted heteroarylene. In embodiments, the linker is a substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the linker is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the linker is an unsubstituted $C_1$-$C_{20}$ alkylene. In embodiments, the linker is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the linker is a substituted or unsubstituted $C_1$-$C_{40}$ alkylene. In embodiments, the linker is a substituted or unsubstituted 2 to 40 membered heteroalkylene. In embodiments, the linker is a substituted 2 to 40 membered heteroalkylene. In embodiments, the linker includes alkyl phosphates (e.g., propyl phosphates). In embodiments, the linker consists of alkyl phosphates (e.g., propyl phosphates) bonded to the reminder of the compound by phosphates at both ends. In embodiments, the linker consists of 1-5 alkyl phosphates (e.g., propyl phosphates) bonded to the reminder of the compound by phosphates at both ends. In embodiments, the linker consists of 1-4 alkyl phosphates (e.g., propyl phosphates) bonded to the reminder of the compound by phosphates at both ends. In embodiments, the linker consists of 4 alkyl phosphates (e.g., propyl phosphates) bonded to the reminder of the compound by phosphates at both ends. A person having ordinary skill in the art will recognize that a linker consisting of alkyl phosphates that is bonded to the remainder of the compound by phosphates on both ends will have one more phosphate than alkylene groups (e.g., a linker consisting of 4 alkyl phosphates that is bonded to the reminder of the compound by phosphates at both ends will have five phosphates and four alkyl groups with alternating phosphate groups and alkyl groups).

In embodiments, saRNA may include modifications such as 2' O-Methyl, 2'-deoxy-2'fluoro, 2'-deoxy, a universal base, 5-C-methyl, an inverted deoxy abasic residue incorporation, or a locked nucleic acid, or any combination(s) thereof. In embodiments, the saRNA may have a modification positioned at the terminal nucleobase of the saRNA. In embodiments, the saRNA may not have a modification positioned at the terminal nucleobase of the saRNA. In embodiments, the modification of the saRNA protects the compound against serum-derived nucleases.

In embodiments, the saRNA includes a guide strand (antisense or AS) sequence of 5'GACCAGUGA-CAAUGACCGCUU 3' [SEQ ID NO: 1] or a sequence having 90%-99% homology to SEQ ID NO: 1, and a passenger strand (sense strand or SS) sequence of 3'UUCUGGUCACUGUUACUGGCG 5' [SEQ ID NO: 2] or a sequence having 90%-99% homology to SEQ ID NO: 2. SEQ ID NO: 1 or a sequence having 90%-99% homology to SEQ ID NO: 1, and SEQ ID NO: 2 or a sequence having 90%-99% homology to SEQ ID NO: 2, together form a saRNA for CEBPA promoter activation. In some embodiments, a saRNA of the present disclosure may include a guide strand (AS) sequence of 5' UACUUGGA-GAAUGAGUUGG 3' [SEQ ID NO: 3] or a sequence having 90%-99% homology to SEQ ID NO: 3, and a passenger strand (SS) sequence of 3' AUGAACCUCUUACUCAACC 5' [SEQ ID NO: 4] or a sequence having 90%-99% homology to SEQ ID NO: 4. SEQ ID NO: 3 or a sequence having 90%-99% homology to SEQ ID NO: 3, and SEQ ID NO: 4 or a sequence having 90%-99% homology to SEQ ID NO: 4, together form a saRNA for p21 promoter activation.

In some embodiments, the saRNA includes a guide strand (AS) sequence of 5'UUAGGAAGGCUUUCCGUAA 3' [SEQ ID NO: 5] or a sequence having 90%-99% homology to SEQ ID NO: 5, and a passenger strand (SS) sequence of 3'AAUCCUUCCGAAAGGCAUU 5' [SEQ ID NO: 6] or a sequence having 90%-99% homology to SEQ ID NO: 6. SEQ ID NO: 5 or a sequence having 90%-99% homology to SEQ ID NO: 5, and 6 or a sequence having 90%-99% homology to SEQ ID NO: 6, together form a saRNA for p53 promoter activation.

In embodiments, the phosphorothioated oligodeoxynucleotide (ODN)-saRNA/ASO conjugate has a terminal moiety. A terminal moiety is a chemically reactive moiety, detectable moiety, therapeutic moiety (e.g. anti-cancer agent or anti-viral agent), nucleic acid sequence, DNA sequence, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, a terminal moiety is a chemically reactive moiety, detectable moiety, therapeutic moiety (e.g. anti-cancer agent or anti-viral agent), nucleic acid sequence, DNA sequence, nucleic acid analogs, $R^1$-substituted or unsubstituted alkyl, $R^1$-substituted or unsubstituted heteroalkyl, $R^1$-substituted or unsubstituted cycloalkyl, $R^1$-substituted or unsubstituted heterocycloalkyl, $R^1$-substituted or unsubstituted aryl, or $R^1$-substituted or unsubstituted heteroaryl.

In embodiments, an phosphorothioated oligodeoxynucleotide (ODN)-saRNA/ASO conjugate includes a terminal moiety, which is a detectable moiety. In embodiments, the phosphorothioated oligodeoxynucleotide (ODN)-saRNA/ASO conjugate includes terminal detectable moiety such as, a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, the phosphorothioated oligodeoxynucleotide (ODN)-saRNA/ASO conjugate includes a terminal moiety, which is a therapeutic moiety (e.g., anti-cancer agent or anti-viral agent).

In embodiments, the phosphorothioated oligodeoxynucleotide (ODN)-saRNA/ASO conjugate includes a terminal moiety, which is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the phosphorothioated oligodeoxynucleotide (ODN)-saRNA/ASO conjugate includes a terminal moiety, which is a substituted or unsubstituted $C_1$-$C_{40}$ alkyl, substituted or unsubstituted 2 to 40 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, the phosphorothioated oligodeoxynucleotide (ODN)-saRNA/ASO conjugate includes a terminal moiety, which is a substituted $C_1$-$C_{40}$ alkyl, substituted 2 to 40 membered heteroalkyl, substituted $C_3$-$C_8$ cycloalkyl, substituted 3 to 8 membered heterocycloalkyl, substituted $C_6$-$C_{10}$ aryl, or substituted 5 to 10 membered heteroaryl. In embodiments, the terminal moiety is an $R^1$-substituted $C1$-$C_{40}$ alkyl, $R^1$-substituted 2 to 40 membered heteroalkyl, $R^1$-substituted $C_3$-$C_8$ cycloalkyl, $R^1$-substituted 3 to 8 membered heterocycloalkyl, $R^1$-substituted $C_6$-$C_{10}$ aryl, or $R^1$-substituted 5 to 10 membered heteroaryl. In embodiments, the terminal moiety is an $R^1$-substituted $C_1$-$C_{40}$ alkyl. In embodiments, the terminal moiety is an -(unsubstituted $C_1$-$C_{40}$ alkylene)-$R^1$. In embodiments, the terminal moiety is an -(unsubstituted linear $C_1$-$C_{40}$ alkylene)-$R^1$. In embodiments, the terminal moiety is an -(unsubstituted $C_3$-$C_{21}$ alkylene)-$R^1$. In embodiments, the terminal moiety is an -(unsubstituted $C_3$-$C_{18}$ alkylene)-$R^1$. In embodiments, the terminal moiety is an -(unsubstituted linear $C_3$-$C_{15}$ alkylene)-$R^1$. In embodiments, the terminal moiety is an -(unsubstituted linear $C_6$-$C_{21}$ alkylene)-$R^1$. In embodiments, the terminal moiety is an -(unsubstituted linear $C_9$-$C_{21}$ alkylene)-$R^1$. In embodiments, the terminal moiety is an -(unsubstituted linear $C_9$-$C_{18}$ alkylene)-$R^1$. In embodiments, the terminal moiety is an -(unsubstituted linear $C_9$-$C_{15}$ alkylene)-$R^1$. In embodiments, the terminal moiety is an -(unsubstituted linear $C_{12}$-$C_{15}$ alkylene)-$R^1$. In embodiments, the terminal moiety is an -(unsubstituted linear $C_{12}$ alkylene)-$R^1$. In embodiments, the terminal moiety is an -(unsubstituted linear $C_{13}$ alkylene)-$R^1$. In embodiments, the terminal moiety is an -(unsubstituted linear $C_{14}$ alkylene)-$R^1$. In embodiments, the terminal moiety is an -(unsubstituted linear $C_{15}$ alkylene)-$R^1$. In embodiments, the terminal moiety is an $R^1$-substituted 2 to 40 membered heteroalkyl. In embodiments, the terminal moiety is an -(unsubstituted 2 to 40 membered heteroalkylene)-$R^1$. In embodiments, the terminal moiety is a -(substituted linear 2 to 40 membered heteroalkylene)-$R^1$. In embodiments, the terminal moiety is a -(substituted 5 to 40 membered heteroalkylene)-$R^1$. In embodiments, the terminal moiety is a -(substituted 10 to 40 membered heteroalkylene)-$R^1$. In embodiments, the terminal moiety is a -(substituted 15 to 40 membered heteroalkylene)-$R^1$. In embodiments, the terminal moiety is a -(substituted 20 to 40 membered heteroalkylene)-$R^1$. In embodiments, the terminal moiety is a -(substituted 30 to 40 membered heteroalkylene)-$R^1$. In embodiments, the terminal moiety is a -(substituted 2 to 35 membered heteroalkylene)-$R^1$. In embodiments, the terminal moiety is a -(substituted 2 to 30 membered heteroalkylene)-$R^1$. In embodiments, the terminal moiety is a -(substituted 2 to 25 membered heteroalkylene)-$R^1$. In embodiments, the terminal moiety is a -(substituted 2 to 20 membered heteroalkylene)-$R^1$. In embodiments, the terminal moiety is a -(substituted 2 to 10 membered heteroalkylene)-$R^1$. In embodiments, the terminal moiety is a -(substituted 2 to 50 membered heteroalkylene)-$R^1$. In embodiments, the terminal moiety is a -(substituted 2 to 60 membered heteroalkylene)-$R^1$.

In embodiments, the phosphorothioated oligodeoxynucleotide (ODN)-saRNA/ASO conjugate includes a terminal moiety, which is a substituted 2 to 40 membered heteroalkyl. In embodiments, the phosphorothioated oligodeoxynucleotide (ODN)-saRNA/ASO conjugate includes a terminal moiety, which is a substituted 10 to 50 membered heteroalkyl. In embodiments, the phosphorothioated oligodeoxynucleotide (ODN)-saRNA/ASO conjugate includes a terminal moiety, which is a substituted 20 to 40 membered heteroalkyl. In embodiments, the phosphorothioated oligodeoxynucleotide (ODN)-saRNA/ASO conjugate includes a terminal moiety, which is a substituted 25 to 40 membered heteroalkyl. In embodiments, the phosphorothioated oligodeoxynucleotide (ODN)-saRNA/ASO conjugate includes a terminal moiety, which is a substituted 30 to 40 membered heteroalkyl.

In embodiments, the phosphorothioated oligodeoxynucleotide (ODN)-saRNA/ASO conjugate includes a terminal moiety with a $R^1$ group, in which $R^1$ is a detectable moiety or a therapeutic moiety. In embodiments, $R^1$ in the phosphorothioated oligodeoxynucleotide (ODN)-saRNA/ASO conjugate terminal moiety is a detectable moiety. In embodiments, $R^1$ in the phosphorothioated oligodeoxynucleotide (ODN)-saRNA/ASO conjugate is a detectable moiety, which is a fluorescent dye, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety. In embodiments, $R^1$ in the phosphorothioated oligodeoxynucleotide (ODN)-saRNA/ASO conjugate terminal moiety is a therapeutic moiety (e.g., anti-cancer agent or anti-viral agent). In embodiments, $R^1$ in the phosphorothioated oligodeoxynucleotide (ODN)-saRNA/ASO conjugate terminal moiety is H. In embodiments, $R^1$ in the phosphorothioated oligodeoxynucleotide (ODN)-saRNA/ASO conjugate terminal moiety is oxo. In embodiments, $R^1$ in the phosphorothioated oligodeoxynucleotide (ODN)-saRNA/ASO conjugate terminal moiety is oxygen. In embodiments, $R^1$ in the phosphorothioated oligodeoxynucleotide (ODN)-saRNA/ASO conjugate terminal moiety is sulfur. In embodiments, $R^1$ in the phosphorothioated oligodeoxynucleotide (ODN)-saRNA/ASO conjugate terminal moiety is =S.

In embodiments, the ODN nucleic acid sequence of the compound includes unmethylated CpG or GpC motif. In embodiments, the CpG nucleic acid sequence includes a Class A CpG nucleic acid sequence, a Class B CpG nucleic acid sequence, or a Class C CpG nucleic acid sequence. In embodiments, the GpC nucleic acid sequence includes a Class A GpC nucleic acid sequence, a Class B GpC nucleic acid sequence, or a Class C GpC nucleic acid sequence.

In embodiments, the compound includes phosphorothioated oligodeoxynucleotide (ODN) in which C and G (CpG or GpC) are nucleotides connected by a phosphodiester internucleotide linkage. In embodiments, the compound includes CpG or GpC, wherein C and G are nucleotides connected by a phosphodiester derivative internucleotide linkage.

In embodiments, a Toll-like receptor (TLR)-binding DNA substituent is a Class A CpG oligodeoxynucleotide (ODN). In embodiments, a TLR-binding DNA substituent is a Class B CpG oligodeoxynucleotide (ODN). In embodiments, a TLR-binding DNA substituent is a Class C CpG oligodeoxynucleotide (ODN). In embodiments, a TLR-binding DNA substituent (e.g., TLR9-binding DNA substituent) consists of deoxyribonucleic acids with A, G, C, or T bases and phosphodiester linkages and/or phosphodiester derivative linkages (e.g., phosphorothioate linkage(s)).

TABLE 1

Partial Sequences of the Compounds

| NAME | SEQUENCE 5'-3'<br>(Underlined = phosphorothioate linkage) | SEQ ID NO: |
|---|---|---|
| CpG(A)-ODN | <u>GG</u>TGCATCGATGCAG<u>GGGGG</u> | 7 |
| GpC(B2)-ODN | <u>TCGTCGTTTTGTGCTTTTGTCGTT</u> | 8 |
| ODN 1585 | <u>GGGG</u>TCAACGTTGA<u>GGGGGG</u> or<br><u>GGGG</u>TCAACGTTGA<u>GGGGGG</u> | 9<br>100 |
| ODN 2216 | <u>GGGG</u>GACGATCGTC<u>GGGGGG</u> | 10 |
| ODN D19 | <u>GG</u>TGCATCGATGCAG<u>GGGGG</u> | 11 |
| ODN 2336 | <u>GGGG</u> ACGACGTCGT <u>GGGGGG</u> or<br><u>GGGG</u> ACGACGTCGT <u>GGGGGG</u> | 12<br>101 |
| ODN 1668<br>CpG(B1)-ODN | <u>TCCATGACGTTCCTGATGCT</u> | 13 |
| ODN 1826 | <u>TCCATGACGTTCCTGACGTT</u> | 14 |
| ODN 2006<br>(ODN7909)<br>CpG(B2)-ODN | <u>TCGTCGTTTTGTCGTTTTGTCGTT</u> | 15 |

TABLE 1-continued

Partial Sequences of the Compounds

| NAME | SEQUENCE 5'-3' (Underlined = phosphorothioate linkage) | SEQ ID NO: |
|---|---|---|
| ODN 2007 | TCGTCGTTGTCGTTTTGTCGTT | 16 |
| ODN 2395 | TCGTCGTTTTCGGCGCGCGCCG | 17 |
| ODN M362 | TCGTCGTCGTTCGAACGACGTTGAT | 18 |
| GpC(A)-ODN | GGTGCATGCATGCAGGGGGG | 29 |
| PS-(CpG/GpC)-ODN | GGT GCA T(CG/GC) ATG CAG GGGGG (the sequence of PS-GpC-ODN has a GC rather than CG at TCG) | 30 |
| CpG(B3)-ODN | TCGTCGTTTTGTCGTTTTGTCCTT | 98 |
| CpG(B4)-ODN | TCCTCGTTTTGTCGTTTTGTCCTT | 99 |
| STAT3 ASO1 | CTATTTGGATGTCAGC CTATTTGGATGTCAGC | 31 110 |
| STAT3 ASO2 | CAGCAGATCAAGTCCAGGGA CAGCAGATCAAGTCCAGGGA | 32 111 |
| STAT3 ASO3 | TTTTGCATGATGTAACCACT | 33 |
| STAT3 ASO1-1 | 5' CTA TTT GGA TGT CAGC 3' | 34 |
| STAT3 ASO2-1 | 5' CAGCAGATCAAGTCCAGGGA 3' | 35 |
| STAT3 ASO3-1 | 5' TTTTGCATGATGTAACCACT 3' | 36 |
| STAT3 ASO4-1 | 5' ATCAAAGTCATCCTGGAG 3' | 37 |
| STAT3 LNA ASO1-1 | 5' *GCA*ACCTGACTTT*AGT* 3' | 38 |
| STAT3 LNA ASO2-1 | 5' *GAT*TCTGCTAATGA*CG* 3' | 39 |
| STAT3 LNA ASO3-1 | 5' *TGA*CGGGTCTGAA*GTT* 3' | 40 |
| STAT3 LNA ASO4-1 | 5' *AGA*TAGCAGAAGTA*GG* 3' | 41 |
| STAT3 LNA ASO5-1 | 5' *GTC*AATGCACACT*TTA* 3' | 42 |
| STAT3 ASO5 | AAAAAGTGCCCAGATTGCCC | 112 |
| STAT3 ASO6 | ACTCAAACTGCCCTCCTGCT | 113 |

*Underlined: phosphorothioation (one non-bridging oxygen on the 3' adjacent phosphate replaced with sulfur) nucleotides (for example GGGGGG is GG*G*G*G*G in 5'-G*G*TGCATCGATGCAGG*G*G*G*G-3', where the asterix (*) is placed between the bases (more accurately: nucleosides) and the phosphorothioated phosphate is also placed between bases); Bold: 2'OMe (2'-O-Methylnucleoside; Hydroxyl in 2'-position replaced with 2'-OMethyl) nucleotides; *italicized*: LNA-modified nucleotides; Bold: 2'OMe (2'-O-Methylnucleoside; Hydroxyl in 2'-position replaced with 2'-OMethyl) nucleotides; *italicized*: LNA-modified nucleotide.

In embodiments, the compounds of the present disclosure include combination of one of phosphorothioated oligodeoxynucleotides (ODN) of SEQ ID NOs: 7-18, 29-30, and 98-101 with CEBPA saRNA (SEQ ID NOs: 1-2), p21 saRNA (SEQ ID NOs: 3-4), or p53 saRNA (SEQ ID NOs: 5-6), joined by a linker, as described in the present disclosure. In embodiments, the compounds of the present disclosure include combination of one of phosphorothioated oligodeoxynucleotides (ODN) of SEQ ID NOs: 7-18, 29-30, and 98-101, with one of SEQ ID NOs: 31-42 and 110-113, joined by a linker, as described in the present disclosure.

Examples of combination of the compounds are listed in Tables 2-4.

In embodiments, the compound binds an endosomal TLR. In embodiments, the compound preferentially binds an endosomal TLR over other TLR. In embodiments, the compound specifically binds an endosomal TLR. In embodiments, the compound binds TLR3. In embodiments, the compound preferentially binds TLR3 over other TLR. In embodiments, the compound specifically binds TLR3. In embodiments, the compound binds TLR7. In embodiments, the compound preferentially binds TLR7 over other TLR. In embodiments, the compound specifically binds TLR7. In embodiments, the compound binds TLR8. In embodiments, the compound preferentially binds TLR8 over other TLR. In embodiments, the compound specifically binds TLR8. In embodiments, the compound binds TLR9. In embodiments, the compound preferentially binds TLR9 over other TLR. In embodiments, the compound specifically binds TLR9. In embodiments, the compound includes CpG, wherein C and G are nucleotides connected by a phosphodiester internucleotide linkage or phosphodiester derivative internucleotide linkage.

In embodiments, the TLR-binding DNA substituent is a Class A CpG oligodeoxynucleotide (ODN). In embodiments, the TLR-binding DNA substituent is a Class B CpG oligodeoxynucleotide (ODN). In embodiments, the TLR-binding DNA substituent is a Class C CpG oligodeoxynucleotide (ODN). In embodiments, the TLR-binding DNA substituent is ODN 1585, ODN 2216, ODN D19, or ODN 2336. In embodiments, the TLR-binding DNA substituent is ODN 1668, ODN 1826, ODN 2006, or ODN 2007. In embodiments, the TLR-binding DNA substituent is ODN 2395 or ODN M362. In embodiments, the TLR-binding DNA substituent is a derivative of ODN 1585, ODN 2216, ODN D19, ODN 2336, ODN 1668, ODN 1826, ODN 2006, ODN 2007, ODN 2395 or ODN M362. In embodiments, a derivative of ODN 1585, ODN 2216, ODN D19, ODN 2336, ODN 1668, ODN 1826, ODN 2006, ODN 2007, ODN 2395 or ODN M362 includes one or more (e.g., 1, 2, 3, 4, 5, 6, 7, 8, 9, or 10) nucleotide substitutions (e.g., A, C, G, or T substituted with a different nucleotide). In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, or 10) internucleotide linkage replacements (e.g., phosphodiester replaced with a phosphodiester derivative or a phosphodiester derivative replaced with a phosphodiester). In embodiments, a derivative of ODN 1585, ODN 2216, ODN D19, ODN 2336, ODN 1668, ODN 1826, ODN 2006, ODN 2007, ODN 2395 or ODN M362 includes one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide deletions. In embodiments, a derivative of ODN 1585, ODN 2216, ODN D19, ODN 2336, ODN 1668, ODN 1826, ODN 2006, ODN 2007, ODN 2395 or ODN M362 includes one or more (e.g., 1, 2, 3, 4, 5, 6, 7, 8, 9, or 10) nucleotide additions.

In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages). In embodiments, the compound includes a plurality of phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof). In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphono- formic acid, methyl phosphonate, boron phosphonate, or O-methylphosphoroamidite linkages) in the TLR9-binding DNA substituent. In embodiments, the compound includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the TLR-binding nucleic acid (e.g., endosomal TLR-, TLR3-, TLR7-, TLR8-, or TLR9-binding nucleic acid) substituent.

In embodiments, the phosphodiester derivative linkage in the CpG nucleic acid sequence may be phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage.

In embodiments, one or more of the nucleic acid internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g., 1, 2, 3, 4, 5, 6, 7, 8, 9, 10, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)).

In embodiments, the present disclosure includes a compound linking CpG to an antisense oligonucleotide targeting CEBPA. In embodiments, the OND-saRNA is present in the cytoplasm (and in the cell nucleus). In embodiments, the nuclear delivery of ODN-Antisense oligonucleotide conjugates affects gene expression as a result of RNaseH-mediated effects on the antisense oligonucleotides.

In embodiments, the present disclosure includes a compound linking an OND to an antisense oligonucleotide targeting STAT. For example, present disclosure includes compounds of ODN-STAT3-ASO (antisense), as listed in Tables 2, 3, and/or 4.

Composition

In one aspect, the present disclosure provides pharmaceutical compositions including a pharmaceutically acceptable excipient and a compound disclosed herein. In embodiments, the composition includes a second therapeutic agent. In embodiments, the second therapeutic agent is an anti-cancer agent. In embodiments, the second therapeutic agent may be part of the same unit dosage or part of a separate unit dosage. The second therapeutic agent is not one of compounds listed in Tables 1-4 or derivatives thereof.

In embodiments, the present disclosure includes compositions of a combination of a compound of the present disclosure with one or more additional anti-cancer therapies, e.g., an anti-VEGF antibody, or anti-STAT agents. Additional examples of anti-cancer therapies include, without limitation, surgery, radiation therapy (radiotherapy), biotherapy, immunotherapy, chemotherapy (e.g., temozolomide), or a combination of these therapies. In addition, cytotoxic agents, anti-angiogenic and anti-proliferative agents can be used in combination with a composition including a compound of the present disclosure.

In certain aspects of any of the methods and uses, the disclosure includes treating cancer, by administering effective amounts of a compound of the present disclosure and a chemotherapeutic agents to a subject diagnosed with cancer. A variety of chemotherapeutic agents may be used in the combined treatment methods and uses of the present disclosure. In embodiments, the chemotherapeutic agent may be temolozolomide. In embodiments, the chemotherapeutic agent may be administered concommitantly with radiotherapy.

In one example, the combined treatment may involve administration which includes simultaneous administration, using separate formulations or a single pharmaceutical formulation, and consecutive administration in either order, where there may be a time period when both (or all) active agents simultaneously exert their biological activities. Preparation and dosing schedules for such chemotherapeutic agents may be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). The chemotherapeutic agent may precede, or follow administration of a compound or composition of the present disclosure or may be given simultaneously therewith.

In some other aspects of any of the methods and uses, other therapeutic agents useful for combination tumor therapy with a compound of the present disclosure include antagonist of other factors that are involved in tumor growth, such as VEGF, EGFR, ErbB3, ErbB4, STAT or TNF. Sometimes, it may be beneficial to also administer one or more cytokines to the subject. In embodiments, a compound or composition of the present disclosure is co-administered with a growth inhibitory agent. For example, the growth inhibitory agent may be administered first, followed by the compound or composition of the present disclosure. However, simultaneous administration or administration of a compound or composition of the present disclosure first may be possible. Suitable dosages for the growth inhibitory agent are those presently used and may be lowered due to the combined action (synergy) of the growth inhibitory agent and a compound of the present disclosure.

The formulation herein may also contain more than one active compound as necessary for the particular indication being treated, e.g., those with complementary activities that do not adversely affect each other. For example, it may be desirable to further provide agents which bind to EGFR, VEGF (e.g., an antibody which binds a different epitope or same epitope on VEGF), VEGFR, or ErbB2 in the one formulation. Alternatively, or in addition, the composition may include a chemotherapeutic agent, or a cytotoxic agent. Such molecules may be suitably present in combination in amounts that are effective for the purpose intended.

In certain aspects of any of the methods and uses, other therapeutic agents useful for combination cancer therapy with a compound or composition of the present disclosure include other anti-angiogenic agents. Many anti-angiogenic agents have been identified and are known in the arts, including those listed by Carmeliet and Jain (2000). In embodiments, a compound or composition of the present disclosure is used in combination with another CEBPA antagonist, neutralizing anti-CEBPA antibodies, low molecule weight inhibitors of CEBPA, and any combinations thereof.

In embodiments, the present disclosure includes a composition including a CpG nucleic acid sequence conjugated to a short-activating RNA (saRNA) and a compound including a TLR-binding nucleic acid substituent conjugated to a STAT-binding DNA substituent. In embodiments, the STAT is human STAT1, STAT2, STAT3, STAT4, STAT5A, STAT5B, or STAT6. In embodiments, a TLR9-binding DNA substituent conjugated to a STAT3-binding DNA substituent. In embodiments, the TLR9-binding DNA substituent includes a CpG motif. In embodiments, the TLR9-binding DNA substituent includes an unmethylated CpG motif. In embodiments, the TLR9-binding DNA substituent includes a DNA sequence capable of forming a G-quadruplex. In embodiments, the TLR9-binding DNA substituent includes a Class A CpG DNA sequence, a Class B CpG DNA sequence, or a C-type CpG DNA sequence. In embodiments, the STAT3-binding DNA substituent includes a first STAT3-binding DNA sequence covalently bound to a second STAT3-binding DNA sequence by a linker; and In embodiments, the present disclosure includes a composition linking CpG to an antisense oligonucleotide targeting CEBPA. In embodiments, the ODN-saRNA is present in the cytoplasm (and in the cell nucleus). In embodiments, the nuclear delivery of ODN-Antisense oligonucleotide conjugates affects gene expression as a result of RNaseH-mediated effects on the antisense oligonucleotides.

In embodiments, the present disclosure includes a composition linking ODN to an antisense oligonucleotide targeting STAT. For example, three ODN-STAT3-ASO (antisense) conjugates (CpG-ODN and STAT3-ASO conjugates) are listed in Table 2.

TABLE 2

```
1 CpG(D19)- PS + 3 5' GGT GCA TCG ATG CAGGGGGG xxxxx
  STAT3     x        CTATTTGGATGTCAGC 3'
  ASO1-1    2'OM3    (SEQ ID NO: 19)
                     x = -(CH₂)ₙ-PO₄-[(CH₂)ₙ-PO₄]₂-(CH₂)ₙ
                     Underlined bases: phosphorothioation (One non-bridging
                     oxygen replaced with sulfur)
                     Bolded: 2'OMe (2'-O-Methylnucleoside. Hydroxyl in
                     2'-position replaced with 2'-OMethyl 2 CpG(D19)- PS + 5 5' GGT GCA TCG ATG CAGGGGGG xxxxx
  STAT3     x        CAGCAGATCAAGTCCAGGGA 3'
  ASO2-1    2'OMe    (SEQ ID NO: 20)
                     x = -(CH₂)ₙ-PO₄-[(CH₂)ₙ-PO₄]₂-(CH₂)ₙ
                     Underlined bases: phosphorothioation (One non-bridging
                     oxygen replaced with sulfur)
                     Bolded: 2'OMe (2'-O-Methylnucleoside; Hydroxyl in
                     2'-position replaced with 2'-OMethyl
```

TABLE 2-continued

```
3 CpG(D19)- PS + 5 5' GGT GCA TCG ATG CAGGGGGG xxxxx
  STAT3       x       TTTTGCATGATGTAACCACT 3'
  ASO3-1    2'OMe     (SEQ ID NO: 21)
                      x = —(CH₂)ₙ—PO₄—[(CH₂)ₙ—PO₄]ᵤ—(CH₂)ₙ
                      Underlined bases: phosphorothioation (One non-bridging
                      oxygen replaced with sulfur)
                      Bolded: 2'OMe (2'-O-Methylnucleoside; Hydroxyl in
                      2'-position replaced with 2'-OMethyl
```

The linker represented by "x" in Table 2 is —(CH$_2$)$_n$—PO$_4$—[(CH$_2$)$_n$—PO$_4$]$_z$—(CH$_2$)$_n$, in which the symbol n is an integer from 1 to 5 (e.g., 3) and the symbol z is an integer from 0 to 50 (e.g. from 0 to 25, 0 to 10, or 0 to 5). In embodiments, n is 3 and z is 0 to 5 or 1 to 5. In embodiments, n is 3 and z is 0 to 4 or 1 to 4. In embodiments, n is 3 and z is 0 to 3 or 1 to 3. In embodiments, n is 3 and z is 3. 2'OMe (2'-O-Methylnucleoside; Hydroxyl in 2'-position replaced with 2'-OMethyl); PS is phosphorothioation. One none-bridging oxygen replaced with sulfur; PS+3 represents three phosphates in the sequence modified, had one none-bridging oxygen replaced with sulfur; PS+5 represents five phosphates in the sequence modified, had one none-bridging oxygen replaced with sulfur.

For example, as shown below, in embodiments, the nucleobases in the CpG sequence may include a phosphorothioate internucleotide linkage.

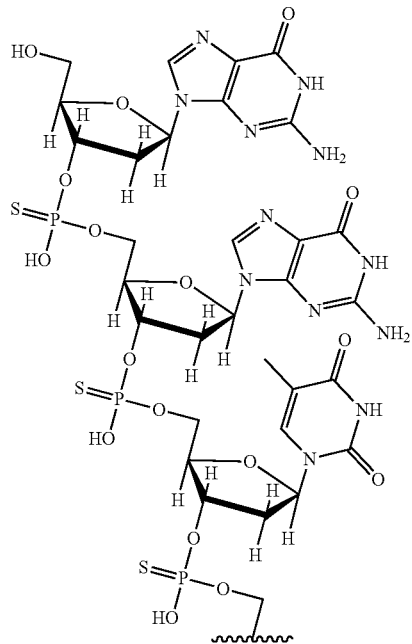

A portion of the CpG nucleic acid sequence with phosphorothioate internucleotide linkage is shown above.

The linker may have the structure below, where the linker connects with the 3' phosphate of the guanine on one end and the 5' phosphate of the thymidine on the other end, and the nucleobases in the antisense part may be modified with 2'OMe.

Five C3 Linkers

The above formula represents a portion of the CpG nucleic acid linked at the 3'-OH end with a (CH2)3 linker, which is links to the 5'-phosphate of the anti-sense RNA.

The linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, a linker connects the TLR9-binding DNA substituent and the STAT3-binding DNA substituent. In embodiments, the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the present disclosure includes a composition including a CpG nucleic acid sequence conjugated to a short-activating RNA (saRNA) and a compound listed in Table 3.

TABLE 3

Compound and component sequences.

| NAME | SEQUENCE (Underlined: phosphorothioation (one non-bridging oxygen on the 3' adjacent phosphate replaced with sulfur) nucleotides), x = —(CH$_2$)$_n$—PO$_4$—[(CH$_2$)$_n$—PO$_4$]$_z$—(CH$_2$)$_n$ bonded to phosphate groups at both ends except at the termini where terminal phosphates are optionally added and 5' x has an OH terminus and 3' x has a —C$^6$-NH$_2$ bonded to the final phosphate group, other linkages are phosphodiester. | SEQ ID NO: |
|---|---|---|
| CpG(A)-STAT3dODN | 5' <u>GGT</u>GCATCGATGCAG<u>GGGGG</u>-xxxxx-<u>CAT</u>TTCCCGTAAATC-xxxx-GATTTACGGG<u>AAT</u>G-xxxxx 3' | 22 |
| GpC(A)-STAT3dODN | 5' <u>GG</u>*TGCATGCATGCAG<u>GGGGG</u>-xxxxx-<u>CAT</u>TTCCCGTAAATC-xxxx-GATTTACGGG<u>AAT</u>G-xxxxx 3' | 23 |
| CpG(A)-scrambled ODN (negative control) | 5' <u>GGT</u>GCATCGATGCAG<u>GGGGG</u>-xxxxx-<u>ACT</u>CTTGCCAATTAC-xxxx-GTAATTGGCA<u>AGA</u>GT-xxxxx 3' | 24 |
| CpG(B2)-STAT3dODN | 5' <u>TCGTCGTTTTGTCGTTTTGTCGTT</u> -xxxxx-<u>CAT</u>TTCCCGTAAATC-xxxx-GATTTACGGG<u>AAT</u>G-xxxxx 3' | 25 |
| CpG(B2)-mutSTAT3 dODN (negative control) | 5' <u>TCGTCGTTTTGTCGTTTTGTCGTT</u>-xxxxx-<u>CAT</u>TTCCCTTAAATC-xxxx-GATTTAAGGG<u>AAT</u>G-xxxxx 3' | 26 |
| CpG(B2)-scrambled ODN (negative control) | 5' <u>TCGTCGTTTTGTCGTTTTGTCGTT</u>-xxxxx-<u>ACT</u>CTTGCCAATTAC-xxxx-GTAATTGGCA<u>AGA</u>GT-xxxxx 3' | 27 |
| STAT3dODN (lacks CpG) | 5' xxxxx-<u>CAT</u>TTCCCGTAAATC-xxxx-GATTTACGGG<u>AAT</u>G-xxxxx 3' | 28 |

TABLE 4

Examples of ASO Compounds

| Sequences of Targeting Moieties and Antisense Oligonucleotides | | SEQ ID NO: |
|---|---|---|
| CpG ODN Sequences (phosphorothioated ASO) | | |
| CpG(A)-ODN-STAT3 ASO1 | 5' <u>GGT</u> GCA TCG ATG CAG <u>GGGGG</u> xxxxx CTA TTT GGA TGT CAGC 3' | 43 |
| CpG(A)-ODN-STAT3 ASO2 | 5' <u>GGT</u> GCA TCG ATG CAG <u>GGGGG</u> xxxxx CAGCAGATCAA GTCCAGGGA 3' | 44 |
| CpG(A)-ODN-STAT3 ASO3 | 5' <u>GGT</u> GCA TCG ATG CAG <u>GGGGG</u> xxxxx TTTTG CATGA TGTAACCACT 3' | 45 |
| CpG(A)-ODN-STAT3 ASO4 | 5' <u>GGT</u> GCA TCG ATG CAG <u>GGGGG</u> xxxxx ATC AAA GTC ATC CTG GAG 3' | 46 |
| CpG(A)-ODN-STAT3 LNA ASO1 | 5' <u>GGT</u> GCA TCG ATG CAG <u>GGGGG</u> xxxxx <u>*GCA ACC TGA CTT TAGT*</u> 3' | 47 |
| CpG(A)-ODN-STAT3 LNS ASO2 | 5' <u>GGT</u> GCA TCG ATG CAG <u>GGGGG</u> xxxxx <u>*GAT TCT GCT AAT GACG*</u> 3' | 48 |
| CpG(A)-ODN-STAT3 LNA ASO3 | 5' <u>GGT</u> GCA TCG ATG CAG <u>GGGGG</u> xxxxx <u>*TGA CGG GTC TGA AGTT*</u> 3' | 49 |
| CpG(A)-ODN-STAT3 LNA ASO4 | 5' <u>GGT</u> GCA TCG ATG CAG <u>GGGGG</u> xxxxx <u>*AGA TAG CAG AAG TAGG*</u> 3' | 50 |

TABLE 4-continued

Examples of ASO Compounds

| Sequences of Targeting Moieties and Antisense Oligonucleotides | | SEQ ID NO: |
|---|---|---|
| CpG(A)-ODN-STAT3 LNA AS05 | 5' <u>GGT GCA TCG ATG CAG GGGGG</u> xxxxx *GTC AAT GCA CAC TTTA* 3' | 51 |
| CpG(B2)-ODN-STAT3 ASO1 | 5' <u>TCGTCGTTTTGTCGTTTTGTCGTT</u>xxxxx CTA TTT GGA TGT CAGC 3' | 52 |
| CpG(B2)-ODN-STAT3 ASO2 | 5' <u>TCGTCGTTTTGTCGTTTTGTCGTT</u> xxxxx CAGCAGATCAAG TCCAGGGA 3' | 53 |
| CpG(B2)-ODN-STAT3 ASO3 | 5' <u>TCGTCGTTTTGTCGTTTTGTCGTT</u> xxxxx TTTTGCATGATG TAACCACT 3' | 54 |
| CpG(B2)-ODN-STAT3 ASO4 | 5' <u>TCGTCGTTTTGTCGTTTTGTCGTT</u> xxxxx ATC AAA GTC ATC CTG GAG 3' | 55 |
| CpG(B2)-ODN-STAT3 LNA ASO1 | 5' <u>TCGTCGTTTTGTCGTTTTGTCGTT</u> xxxxx *GCA* ACC TGA CTT *TAGT* 3' | 56 |
| CpG(B2)-ODN-STAT3 LNA ASO2 | 5' <u>TCGTCGTTTTGTCGTTTTGTCGTT</u> xxxxx *GAT* TCT GCT AAT *GACG* 3' | 57 |
| CpG(B2)-ODN-STAT3 LNA ASO3 | 5' <u>TCGTCGTTTTGTCGTTTTGTCGTT</u> xxxxx *TGA* CGG GTC TGA *AGTT* 3' | 58 |
| CpG(B2)-ODN-STAT3 LNA ASO4 | 5' <u>TCGTCGTTTTGTCGTTTTGTCGTT</u> xxxxx *AGA* TAG CAG AAG *TAGG* 3' | 59 |
| CpG(B2)-ODN-STAT3 LNA ASO5 | 5' <u>TCGTCGTTTTGTCGTTTTGTCGTT</u> xxxxx *GTC AAT GCA CAC TTTA* 3' | 60 |

GpC-ODN Sequences (phosphorothioated ASO)

| | | |
|---|---|---|
| GpC(A)-ODN-STAT3 ASO1 | 5' <u>GGT GCA TGC ATG CAG GGGGG</u> xxxxx CTA TTT GGA TGT CAGC 3' | 61 |
| GpC(A)-ODN-STAT3 ASO2 | 5' <u>GGT GCA TGC ATG CAG GGGGG</u> xxxx CAGCAGATCAAG TCCAGGGA 3' | 62 |
| GpC(A)-ODN-STAT3 ASO3 | 5' <u>GGT GCA TGC ATG CAG GGGGG</u> xxxxx TTTTG CATGA TGTAA CCACT 3' | 63 |
| GpC(A)-ODN-STAT3 ASO4 | 5' <u>GGT GCA TGC ATG CAG GGGGG</u> xxxxx ATC AAA GTC ATC CTG GAG 3' | 64 |
| GpC(A)-ODN-STAT3 LNA ASO1 | 5' <u>GGT GCA TGC ATG CAG GGGGG</u> xxxxx *GCA* ACC TGA CTT *TAGT* 3' | 65 |
| GpC(A)-ODN-STAT3 LNA ASO2 | 5' <u>GGT GCA TGC ATG CAG GGGGG</u> xxxxx *GAT* TCT GCT AAT *GACG* 3' | 66 |
| GpC(A)-ODN-STAT3 LNA ASO3 | 5' <u>GGT GCA TGC ATG CAG GGGGG</u> xxxxx *TGA CGG GTC* TGA *AGTT* 3' | 67 |
| GpC(A)-ODN-STAT3 LNA ASO4 | 5' <u>GGT GCA TGC ATG CAG GGGGG</u> xxxxx *AGA* TAG CAG AAG *TAGG* 3' | 68 |
| GpC(A)-ODN-STAT3 LNA ASO5 | 5' <u>GGT GCA TGC ATG CAG GGGGG</u> xxxxx *GTC AAT GCA CAC TTTA* 3' | 69 |
| GpC(B)-ODN-STAT3 ASO1 | 5' <u>TGCTGCTTTTGTGCTTTTGTGCTT</u> xxxxx CTA TTT GGA TGT CAGC 3' | 70 |
| GpC(B)-ODN-STAT3 ASO2 | 5' <u>TGCTGCTTTTGTGCTTTTGTGCTT</u> xxxxx CAGCAGATCAAG TCCAGGGA 3' | 71 |
| GpC(B)-ODN-STAT3 ASO3 | 5' <u>TGCTGCTTTTGTGCTTTTGTGCTT</u> xxxxx TTTTG CATGAT GTAACCACT 3' | 72 |

TABLE 4-continued

Examples of ASO Compounds

| Sequences of Targeting Moieties and Antisense Oligonucleotides | | SEQ ID NO: |
|---|---|---|
| GpC(B)-ODN-STAT3 ASO4 | 5' TGCTGCTTTTGTGCTTTTGTGCTT xxxxx ATC AAA GTC ATC CTG GAG 3' | 73 |
| GpC(B)-ODN-STAT3 LNA ASO1 | 5' TGCTGCTTTTGTGCTTTTGTGCTT xxxxx *GCA ACC TGA CTT TAGT* 3' | 74 |
| GpC(B)-ODN-STAT3 LNA ASO2 | 5' TGCTGCTTTTGTGCTTTTGTGCTT xxxxx *GAT TCT GCT AAT GACG* 3' | 75 |
| GpC(B)-ODN-STAT3 LNA ASO3 | 5' TGCTGCTTTTGTGCTTTTGTGCTT xxxxx *TGA CGG GTC TGA AGTT* 3' | 76 |
| GpC(B)-ODN-STAT3 LNA ASO4 | 5' TGCTGCTTTTGTGCTTTTGTGCTT xxxxx *AGA TAG CAG AAG TAGG* 3' | 77 |

PS-CpG-ODN Sequences (phosphorothioated ASO)
PS-CpG-ODN (GGTGCATCGATGCAGGGGGG) [SEQ ID NO: 102]

| | | |
|---|---|---|
| PS-CpG-ODN-STAT3 ASO1 | 5' GGT GCA TCG ATG CAG GGGGG xxxxx CTA TTT GGA TGT CAGC 3' | 78 |
| PS-CpG-ODN-STAT3 ASO2 | 5' GGT GCA TCG ATG CAG GGGGG xxxxx CAGCAGATCAA GTCCAGGGA 3' | 79 |
| PS-CpG-ODN-STAT3 ASO3 | 5' GGT GCA TCG ATG CAG GGGGG xxxxx TTTTG CATGA TGTAA CCACT 3' | 80 |
| PS-CpG-ODN-STAT3 ASO4 | 5' GGT GCA TCG ATG CAG GGGGG xxxxx ATC AAA GTC ATC CTG GAG 3' | 81 |
| PS-CpG-ODN-STAT3 LNA ASO1 | 5' GGT GCA TCG ATG CAG GGGGG xxxxx *GCA ACC TGA CTT TAGT* 3' | 82 |
| PS-CpG-ODN-STAT3 LNA ASO2 | 5' GGT GCA TCG ATG CAG GGGGG xxxxx *GAT TCT GCT AAT GACG* 3' | 83 |
| PS-CpG-OSN-STAT3 LNA ASO3 | 5' GGT GCA TCG ATG CAG GGGGG xxxxx *TGA CGG GTC TGA AGTT* 3' | 84 |
| PS-CpG-ODN-STAT3 LNA ASO4 | 5' GGT GCA TCG ATG CAG GGGGG xxxxx *AGA TAG CAG AAG TAGG* 3' | 85 |
| PS-CpG-ODN-STAT3 LNA ASO5 | 5' GGT GCA TCG ATG CAG GGGGG xxxxx *GTC AAT GCA CAC TTTA* 3' | 86 |

PS-CpG-ODN Sequences (phosphorothioated ASO)

| | | |
|---|---|---|
| PS-GpC-ODN-STAT3 ASO1 | 5' GGT GCA TGC ATG CAG GGGGG xxxxx CTA TTT GGA TGT CAGC 3' | 87 |
| PS-GpC-ODN-STAT3 ASO2 | 5' GGT GCA TGC ATG CAG GGGGG xxxxx CAGCAGATCAA GTCCAGGGA 3' | 88 |
| PS-GpC-ODN-STAT3 ASO3 | 5' GGT GCA TGC ATG CAG GGGGG xxxxx TTTTG CATGA TGTAA CCACT 3' | 89 |
| PS-GpC-ODN-STAT3 ASO4 | 5' GGT GCA TGC ATG CAG GGGGG xxxxx ATC AAA GTC ATC CTG GAG 3' | 90 |
| PS-GpC-ODN-STAT3 LNA ASO1 | 5' GGT GCA TGC ATG CAG GGGGG xxxxx *GCA ACC TGA CTT TAGT* 3' | 91 |
| PS-GpC-ODN-STAT3 LNA ASO2 | 5' GGT GCA TGC ATG CAG GGGGG xxxxx *GAT TCT GCT AAT GACG* 3' | 92 |
| PS-GpC-ODN-STAT3 LNA ASO3 | 5' GGT GCA TGC ATG CAG GGGGG xxxxx *TGA CGG GTC TGA AGTT* 3' | 93 |
| PS-GpC-ODN-STAT3 LNA ASO4 | 5' GGT GCA TGC ATG CAG GGGGG xxxxx *AGA TAG CAG AAG TAGG* 3' | 94 |

TABLE 4-continued

Examples of ASO Compounds

| Sequences of Targeting Moieties and Antisense Oligonucleotides | SEQ ID NO: |
|---|---|
| PS-GpC-ODN-STAT3 5' <u>GGT GCA TGC ATG CAG GGGGG</u> xxxxx <u>*GTC AAT GCA*</u><br>LNA AS05          <u>*CAC TTTA*</u> 3' | 95 |

*<u>Underlined</u>: phosphorothioation (one non-bridging oxygen on the 3' adjacent phosphate replaced with sulfur) nucleotides (for example G<u>GGGGG</u> is GG*G*G*G*G in 5'-G*G*TGCATCGATGCAG**G*G*G*G**-3', where the asterix (*) is placed between the bases (more accurately: nucleosides) and the phosphorothioated phosphate is also placed between bases); Bold: 2'OMe (2'-O-Methylnucleoside; Hydroxyl in 2'-position replaced with 2'-OMethyl) nucleotides; *italicized*: LNA-modified nucleotide; Bold: 2'OMe (2'-O-Methylnucleoside; Hydroxyl in 2'-position replaced with 2'-OMethyl) nucleotides; *italicized*: LNA-modified nucleotide.

The linker represented by "x" in Table 3 and in Table 4 is —(CH$_2$)$_n$—PO$_4$—[(CH$_2$)$_n$—PO$_4$]$_z$—(CH$_2$)$_n$, in which the symbol n is an integer from 1 to 5 (e.g., 3) and the symbol z is an integer from 0 to 50 (e.g. from 0 to 25, 0 to 10, or 0 to 5). In embodiments, n is 3 and z is 0 to 5, or 1 to 5. In embodiments, n is 3 and z is 0 to 4, or 1 to 4. In embodiments, n is 3 and z is 0 to 3, or 1 to 3. In embodiments, n is 3 and z is 3. Linker "x" may be present multiple times in concatenation (e.g., 1, 2, 3, 4, 5 or even 6 times), wherein n and z are independent for each occurrence of linker "x."

The present disclosure includes compositions with an effective dose of a compound of the present disclosure. The effective dose may be between about 0.001 mg/kg to about 100 mg/kg of the agent.

The effective dose of a compound of the present disclosure for treating cancer, enhancing C/EBPA expression in a cell, inhibiting cell growth, and/or reducing STAT transcription factor activity may be between about 0.001 mg/kg to about 0.01 mg/kg of the compound, between about 0.01 mg/kg to about 0.1 mg/kg of the compound, between about 0.1 mg/kg to about 1.0 mg/kg of the compound, between about 1.0 mg/kg to about 5.0 mg/kg of the compound, between about 5.0 mg/kg to about 10 mg/kg of the compound, between about 10 mg/kg to about 15 mg/kg of the compound, between about 15 mg/kg to about 20 mg/kg of the compound, between about 20 mg/kg to about 25 mg/kg of the compound, between about 25 mg/kg to about 30 mg/kg of the compound, between about 30 mg/kg to about 35 mg/kg of the compound, between about 35 mg/kg to about 40 mg/kg of the compound, between about 40 mg/kg to about 45 mg/kg of the compound, between about 45 mg/kg to about 50 mg/kg of the compound, between about 50 mg/kg to about 55 mg/kg of the compound, between about 55 mg/kg to about 60 mg/kg of the compound, between about 60 mg/kg to about 65 mg/kg of the compound, between about 65 mg/kg to about 70 mg/kg of the compound, between about 70 mg/kg to about 75 mg/kg of the compound, between about 75 mg/kg to about 80 mg/kg of the compound, between about 80 mg/kg to about 85 mg/kg of the compound, between about 85 mg/kg to about 90 mg/kg of the compound, between about 90 mg/kg to about 95 mg/kg of the compound, or between about 95 mg/kg to about 100 mg/kg of the compound.

In some aspects, the present disclosure includes compositions with an effective dose of a compound of the present disclosure in which the compound may be between about 0.1% to about 20% w/v of the composition.

For example, the effective dose of a compound disclosed herein may be between about 0.001%-about 0.01%, between about 0.01%-about 0.1%, between about 0.1%-about 1.0%, between about 1.0%-about 2.0%, between about 2.0%-about 3.0%, between about 3.0%-about 4.0%, between about 4.0%-about 5.0%, between about 5.0%-about 6.0%, between about 6.0%-about 7.0%, between about 7.0%-about 8.0%, between about 8.0%-about 9.0%, between about 9.0%-about 10%, between about 10%-about 11%, between about 11%-about 12%, between about 12%-about 13%, between about 13%-about 14%, between about 14%-about 15%, between about 15%-about 16%, between about 16%-about 17%, between about 17%-about 18%, between about 18%-about 19%, or between about 19%-about 20% w/v of the composition.

Method of and/or Use in Enhancing or Suppressing Gene Expression

Enhancing Gene Expression and Stimulating Immune Response

In one aspect, the present disclosure includes a method of enhancing expression gene expression and stimulating immune response, with a compound and/or composition of the disclosure. In embodiments, the enhancing expression of a gene and stimulating immune response is achieved with a saRNA conjugated with a phosphorothioated oligodeoxynucleotide (ODN) sequence having a CpG sequence. In embodiments, expression of C/EBPA, p21, and p53 is enhanced and immune response is stimulated with saRNA of C/EBPA, p21, and p53, respectively, conjugated with a phosphorothioated oligodeoxynucleotide (ODN) sequence, e.g., one of SEQ ID NO: 7-18.

Enhancing Gene Expression and Stimulating Immune Response

In one aspect, the present disclosure includes a method of enhancing expression gene expression, without stimulating immune response, with a compound and/or composition of the disclosure. In embodiments, the enhancing expression of a gene without stimulating immune response is achieved with a saRNA conjugated with a phosphorothioated oligodeoxynucleotide (ODN) sequence having a GpC or PS sequence of the present disclosure. In embodiments, expression of C/EBPA, p21, and p53 is enhanced, without stimulating immune response, with saRNA of C/EBPA, p21, and p53, respectively, conjugated with a phosphorothioated oligodeoxynucleotide (ODN) sequence, e.g., one of SEQ ID NO: 29-30.

Suppressing Gene Expression and Stimulating Immune Response

Figure 15A:
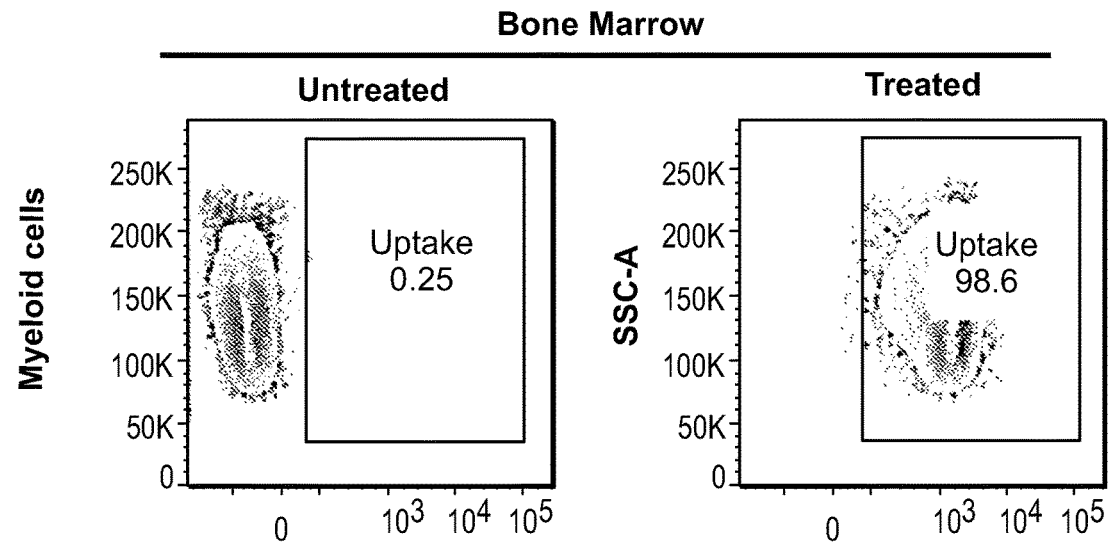
FIGS. 15A-15C show flow cytometry data of the in vivo biodistribution of systemically injected CpG-STAT3ASO$^{Cy3}$. C57BL/6 mice were injected intravenously using 5 mg/kg of Cy3-labeled CpG-STAT3 ASO$^{Cy3}$ and euthanized 3 hours later. Representative contour plots (Bone marrow is depicted in FIG. 15A; and Lymph node is depicted in FIG. 15B) show internalization of oligonucleotide by CD11b$^+$ myeloid cells or CD11c$^+$ dendritic cells (DCs) using flow cytometry on single cell suspensions from bone marry and peripheral lymph nodes; (n=4).
Figure 15B:
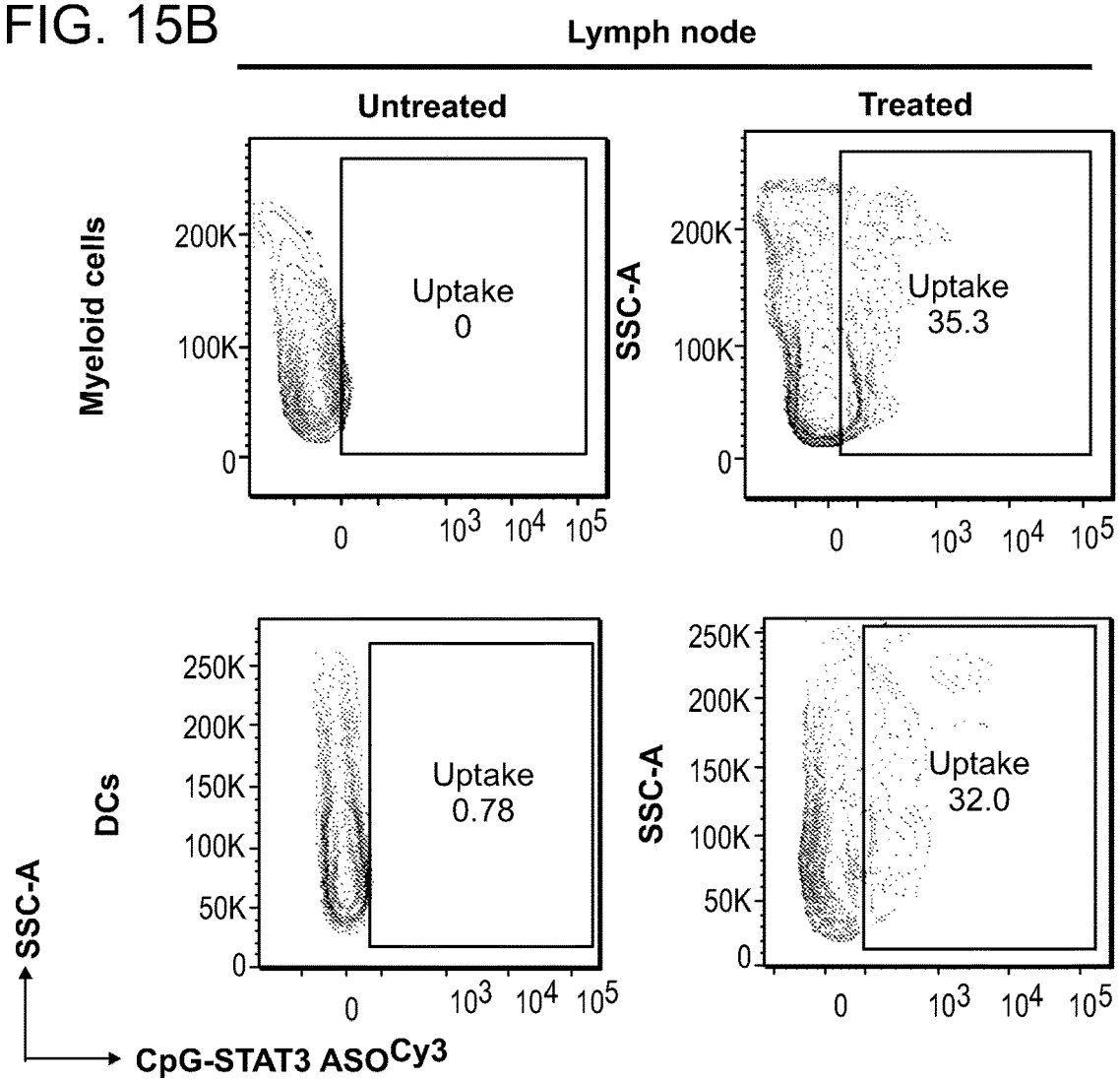

In one aspect, the present disclosure includes a method of suppressing a gene with a compound and/or composition while inducing an immunogenic effect. In embodiments, the present disclosure provides a method of suppressing a gene, e.g., a STAT, with a compound of one of phosphorothioated oligodeoxynucleotides (ODN) of SEQ ID NOs: 7-18 and 98-101 linked to one of SEQ ID NOs: 31-42 and 110-113. For example, the method of suppressing STAT gene (one of STAT1-STAT5) is achieved with a compound of SEQ ID NOs: 43-60. These compounds allow for quick internalization by target TLR9+ cells such as mammalian (e.g. human) immune cells, prostate cancer cells, within one hour of incubation. The uptake of the compounds may be detectable at the low concentration (e.g., 50 nM). These sequences are nuclease-resistant and allow for systemic administration and targeting of TLR9+ cells in distant organs, such as spleen or bone marrow (FIGS. 15A-15B). Intravenous (IV) injection of the compound may deliver the compound to the majority of myeloid cells in the bone marrow and significant proportion of myeloid cells, including DCs, in the peripheral lymph nodes (FIGS. 15A-15B). In embodiments, STAT expression is suppressed, while stimulating immune response, in malignant cells and/or tumor-associated immune cells, e.g., myeloid-derived suppressor cells (MDSCs). MDSCs are heterogeneous population of immature and potentially immunosuppressive myeloid cells, which play pivotal role in prostate cancer progression and poor patient survival. In embodiments, STAT expression is suppressed in hormone-refractory/castration-resistant prostate cancer (CRPC), while simultaneously stimulating immune response.

Suppressing Gene Expression without Stimulating Immune Response

In one aspect, the present disclosure includes a method of suppressing a gene with a compound and/or composition without inducing an immunogenic effect. In embodiments, the present disclosure provides a method of suppressing a gene, e.g., a STAT (one of STAT1-STAT5), with a compound, e.g., of one of phosphorothioated oligodeoxynucleotides (ODN) of SEQ ID NOs: 29-30 linked to, e.g., one of SEQ ID NOs: 31-42 and 110-113. For example, suppression of STAT1-STAT5 is achieved with a compound of SEQ ID NOs: 61-95, without stimulating an immunogenic effect. The compounds of SEQ ID NOs: 78-95 have higher stability compared to compounds of SEQ ID NOs: 61-77. In embodiments, STAT expression is suppressed, without stimulating immune response, in malignant cells and/or tumor-associated immune cells, e.g., myeloid-derived suppressor cells (MDSCs). In embodiments, STAT expression is suppressed in hormone-refractory/castration-resistant prostate cancer (CRPC), without stimulating immune response.

Method of Suppressing Gene Expression and Inducing Apoptosis

In one aspect, the present disclosure includes a method of suppressing a gene with a compound and/or composition of the present disclosure while inducing apoptosis. In embodiments, the present disclosure provides a method of suppressing a gene, e.g., a STAT (STAT1-STAT5), with a compound of, e.g., one of phosphorothioated oligodeoxynucleotides (ODN) of SEQ ID NOs: 7-18 and 98-101 linked to, e.g., one of SEQ ID NOs: 31-42 and 110-113. For example, the method of suppressing STAT1-STAT5 is achieved with a compound of, e.g., SEQ ID NOs: 43-60, while inducing apoptosis of the target cells.

Method of Suppressing Gene Expression without Inducing Apoptosis

In one aspect, the present disclosure includes a method of suppressing a gene with a compound and/or composition without inducing apoptosis. In embodiments, the present disclosure provides a method of suppressing a gene, e.g., a STAT (STAT1-STAT5), with a compound of, e.g., one of phosphorothioated oligodeoxynucleotides (ODN) of SEQ ID NOs: 29-30 linked to, e.g., one of SEQ ID NOs: 31-42 and 110-113, without inducing apoptosis. For example, the method of suppressing STAT1-STAT5 is achieved with a compound of, e.g., SEQ ID NOs: 61-95, without inducing apoptosis of the target cell.

Method of Treating Cancer

In one aspect, the present disclosure includes a method of treating cancer and/or a tumor with a compound and/or composition of the disclosure, while inducing an immunogenic effect. In one aspect, the method includes treating cancer and/or a tumor with a compound and/or composition of the disclosure, without inducing an immunogenic effect.

In embodiments, the cancer may be a hematopoietic cell cancer. In embodiments, the cancer is not a hematopoietic cell cancer. In embodiments, the cancer is myeloma or acute myeloid leukemia. In embodiments, the cancer is prostate cancer (e.g., hormone-refractory/castration-resistant prostate cancer (CRPC)), breast cancer, glioblastoma, ovarian cancer, lung cancer, head and neck cancer, esophageal cancer, skin cancer, melanoma, brain cancer, colorectal cancer, leukemia, lymphoma, or myeloma.

In embodiments, the compound or the composition is administered to the subject by intravenous, parenteral, subcutaneous, intramuscular, transdermal, intraperitoneal, intranasal, aerosol, oral, or topical administration. In embodiments, the treatment is dose-dependent of the compound or composition. In embodiments, about 0.001 mg/kg to about 100 mg/kg of the compound is administered to the subject. All digits and various ranges within this range are also implied.

Treating Cancer and Inducing Immune Response

In embodiments, the present disclosure provides a method of treating cancer in a subject in need thereof, the method including administering to the subject an effective amount of a compound or the pharmaceutical composition including a compound disclosed herein. The present disclosure provides a method of treating cancer and stimulating an immune response in a subject in need thereof, the method including administering to the subject an effective amount of a compound or a pharmaceutical composition including a compound of one of phosphorothioated oligodeoxynucleotides (ODN) of, e.g., SEQ ID NOs: 7-18 and 98-101 linked to, e.g., one of CEBPA saRNA (SEQ ID NOs: 1-2), p21 saRNA (SEQ ID NOs: 3-4), p53 saRNA (SEQ ID NOs: 5-6), or one of STAT ASOs of, e.g., SEQ ID NOs: 31-42 and 110-113.

In embodiments, the method of treating cancer includes administering a subject in need thereof, compound or a composition of a compound of a combination of one of phosphorothioated oligodeoxynucleotides (ODN) of, e.g., SEQ ID NOs: 7-18, 29-30, and 98-101, with CEBPA saRNA (SEQ ID NOs: 1-2), p21 saRNA (SEQ ID NOs: 3-4), or p53 saRNA (SEQ ID NOs: 5-6), joined by a linker, as described in the present disclosure. In embodiments, the method of treating cancer includes administering a subject in need thereof, a compound or a composition of a compound of a combination of one of phosphorothioated oligodeoxynucleotides (ODN) of, e.g., SEQ ID NOs: 7-18, 29-30, and 98-101, with one of, e.g., SEQ ID NOs: 31-42 and 110-113, joined by a linker, as described in the present disclosure.

In embodiments, the stimulation of immune response includes maturation, differentiation, or proliferation of natural killer cells, T cells, B cells or myeloid cells. In embodiments, the stimulation of immune response includes an increase in $T_H1$-type immune response. In embodiments the stimulation of immune response may recruit dendritic cells and CD8+ T cells into an organ of the subject. In embodiments, the stimulation of immune response expands population of antigen-presenting cells in the subject. In embodiments, the stimulation of immune response suppresses proliferation of cancer cells in the subject. In embodiments, the compound or the composition is administered to the subject by intravenous, parenteral, subcutaneous, intramuscular, transdermal, intraperitoneal, intranasal, aerosol, oral, or topical administration in order to stimulate immune response.

The present disclosure provides a method of enhancing C/EBPα, p21, and/or p53 expression in a cell, and simultaneously inducing immunogenic effect, the method including contacting the cell with an effective amount of a compound or a pharmaceutical composition of a compound of one of phosphorothioated oligodeoxynucleotides (ODN) of, e.g., SEQ ID NOs: 7-18 and 98-101 linked to one of CEBPA saRNA (SEQ ID NOs: 1-2), p21 saRNA (SEQ ID NOs: 3-4), and p53 saRNA (SEQ ID NOs: 5-6), respectively. The present disclosure provides a method of inhibiting cell growth including contacting the cell with an effective amount of a compound or a pharmaceutical composition of a compound of one of phosphorothioated oligodeoxynucleotides (ODN) of, e.g., SEQ ID NOs: 7-18 and 98-101 linked to one of CEBPA saRNA (SEQ ID NOs: 1-2), p21 saRNA (SEQ ID NOs: 3-4), and p53 saRNA (SEQ ID NOs: 5-6), respectively. The present disclosure provides a method of reducing the activity of a STAT transcription factor in a cell including contacting the cell with an effective amount of a compound or a pharmaceutical composition of one of phosphorothioated oligodeoxynucleotides (ODN) of, e.g., SEQ ID NOs: 7-18 and 98-101 linked to one of, e.g., SEQ ID NOs: 31-42 and 110-113.

In embodiments, the cell is a cancer cell. In embodiments, the cell is an acute myeloid lymphoid (AML) cell or a prostate cancer cell. In embodiments, the AML cell is from the bone marrow. In embodiments, the cell is a cultured cell in vitro, the cell is in situ in a host, the cell is in a cultured tissue ex vivo. In embodiments, the contacting step is free of viral transduction. In embodiments, the contacting step is free of viral transduction and the cell is contacted with a compound of the present disclosure or a pharmaceutical composition including a compound of the present disclosure. In embodiments the cell is contacted with about 1 nanomolar to about 100 nanomolar of the compound. All digits and various ranges within this range are also implied.

Intravenous injections of CpG-CEBPA saRNA induced expression of C/EBPα protein and led to dose-dependent reduction in the percentage of leukemic cells in blood and in various organs. At 2.5 mg/kg and above repeated injections of CpG-CEBPA saRNA resulted in complete AML eradication. The antitumor efficacy of this strategy seems to be further enhanced by immunostimulatory effect of combined TLR9-triggering and C/EBPα upregulation. In Cbfb/MYH11/Mp11 leukemia model, i.v. injections of CpG-CEBPA saRNA resulted in recruitment of dendritic cells and CD8+ T cells into various organs. Thus, CpG-CEBPA saRNA strategy can provide a novel and cell-selective strategy for therapy of AML and potentially prostate cancer. With a known role of C/EBPα in myeloid cell differentiation, CpG-CEBPA saRNA could allow for expanding population of antigen-presenting cells in cancer patients, while suppressing proliferation of cancer cells.

Phosphorothioated and single-stranded CpG ODN part of the conjugate trigger internalization by target cells. The endosomal uptake of CpGCEBPA saRNA is mediated through scavenger receptors and leads to interaction with TLR9. TLR9 activation generates immunostimulatory signal (signal 1) while also enables release of the conjugate into cytoplasm. CpG-CEBPA saRNA eventually reaches nucleus interacting with gene expression machinery and thereby leading to expression of the target gene. The C/EBPα protein acts as a transcriptional activator of cell differentiation (signal 2). The combination of both immunostimulation and differentiation signals enhance the antigen presentation and result in potent antitumor immune responses.

STAT3 activity is often triggered by cytokines released in response to stress and inflammation, downstream from Toll-like receptor (TLR) and NF-κB signaling. The TLR9/NF-κB/STAT3 signaling axis has a role in the prostate cancer cell self-renewal, tumorigenic potential and therapeutic resistance. As a unique a point of convergence for inflammatory and tumorigenic signaling, STAT3 is activated in both malignant cells and tumor-associated immune cells such as myeloid-derived suppressor cells (MDSCs). The MDSCs are heterogeneous population of immature and potently immunosuppressive myeloid cells which play pivotal role in prostate cancer progression and poor patients' survival. TLR9$^+$ granulocytic MDSCs (G-MDSCs; Lin$^-$HLA-DR$^-$CD14$^-$CD15$^{HI}$CD33$^{LO}$) are a population of cells with highly activated STAT3 which accumulated in blood of prostate cancer patients during progression of the disease from localized to metastatic/castration-resistant prostate cancer (mCRPC). In embodiments, the strategy is for targeted gene suppression, e.g., in TLR9+ cells in the tumor microenvironment such as myeloid immune cells and B lymphocytes. In embodiments, TLR9-positive hematologic malignancies and cancer stem-like cells in solid tumors such as prostate cancers and glioblastoma is treated. In embodiments, STAT expression is suppressed, without stimulating immune response, in malignant cells and/or tumor-associated immune cells, e.g., myeloid-derived suppressor cells (MDSCs). In embodiments, STAT expression is suppressed in hormone-refractory/castration-resistant prostate cancer (CRPC), while simultaneously stimulating immune response, thereby treating CRPC.

Treating Cancer without Stimulating an Immune Response

The present disclosure provides a method of treating cancer without stimulating an immune response in a subject in need thereof, the method including administering to the subject an effective amount of a compound or a pharmaceutical composition including a compound of, e.g., one of SEQ ID NOs: 29-30 linked to, e.g., one of CEBPA saRNA (SEQ ID NOs: 1-2), p21 saRNA (SEQ ID NOs: 3-4), p53 saRNA (SEQ ID NOs: 5-6), or one of STAT ASOs of, e.g., SEQ ID NOs: 31-42 and 110-113.

In embodiments, the compound or the composition including a compound of, e.g., SEQ ID NOs: 29-30 linked to one of CEBPA saRNA (SEQ ID NOs: 1-2), p21 saRNA (SEQ ID NOs: 3-4), p53 saRNA (SEQ ID NOs: 5-6), or one of, e.g., STAT ASOs of SEQ ID NOs: 31-42 and 110-113, is administered to the subject by intravenous, parenteral, subcutaneous, intramuscular, transdermal, intraperitoneal, intranasal, aerosol, oral, or topical administration in order to treat cancer, without stimulating an immune response.

The present disclosure provides a method of enhancing C/EBPα, p21, and/or p53 expression in a cell, without simultaneously inducing immunogenic effect, the method including contacting the cell with an effective amount of a compound or a pharmaceutical composition of a compound of, e.g., one of SEQ ID NOs: 29-30 linked to one of CEBPA saRNA (SEQ ID NOs: 1-2), p21 saRNA (SEQ ID NOs: 3-4), and p53 saRNA (SEQ ID NOs: 5-6), respectively. The present disclosure provides a method of inhibiting uncontrolled cell growth and/or proliferation, without simultaneously inducing an immune response, including contacting the cell with an effective amount of a compound or a pharmaceutical composition of a compound of, e.g., one of SEQ ID NOs: 29-30 linked to one of CEBPA saRNA (SEQ ID NOs: 1-2), p21 saRNA (SEQ ID NOs: 3-4), and p53 saRNA (SEQ ID NOs: 5-6), respectively, or one of STAT ASOs of, e.g., SEQ ID NOs: 31-42 and 110-113. The present disclosure provides a method of reducing the activity of a STAT transcription factor in a cell, without simultaneously inducing an immune response, including contacting the cell with an effective amount of a compound or a pharmaceutical composition of, e.g., one of SEQ ID NOs: 29-30 linked to, e.g., one of SEQ ID NOs: 31-42 and 110-113. In embodiments, the present disclosure provides a method of treating cancer, inhibiting uncontrolled cell growth and/or proliferation, and/or reducing activity of STAT transcription factor in a cell, e.g., a STAT, without inducing immune response, with a compound of, e.g., one of SEQ ID NOs: 29-30 linked to, e.g., one of SEQ ID NOs: 31-42 and 110-113. For example, the method of includes administering a compound of, e.g., SEQ ID NOs: 61-95, which do not induce immune response. In embodiments, STAT expression is suppressed in hormone-refractory/castration-resistant prostate cancer (CRPC), without stimulating immune response, thereby treating CRPC.

Disruption of Signaling Cross Talk within the Tumor Microenvironment

Figure 9A:
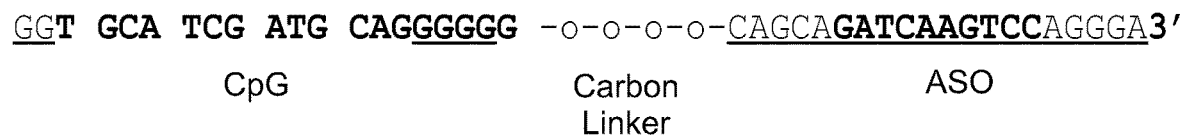
FIGS. 9A-9C show exemplary sequence design and PAGE gel data of CpG-STAT3 ASO conjugates. An example of the single-stranded CpG-STAT3 ASO design is shown in FIG. 9A. Phosphorothioated nucleotides are underlined; $(CH_2)_3$ units of the carbon linker are in blue; 2'OMe-modified nucleotides in the gapmer sequence of STAT3ASO2 are in red. CpG-STAT3ASO2 (FIG. 9B) and CpG-STAT3ASO4 (FIG. 9C) conjugates were incubated in 50% human serum at 37 C for up to 5 days. The samples were then resolved on 7.5M Urea/20% PAGE gel and stained using ethidium bromide; the representative gel images are shown; M indicates position of DNA marker.
Figure 12A:
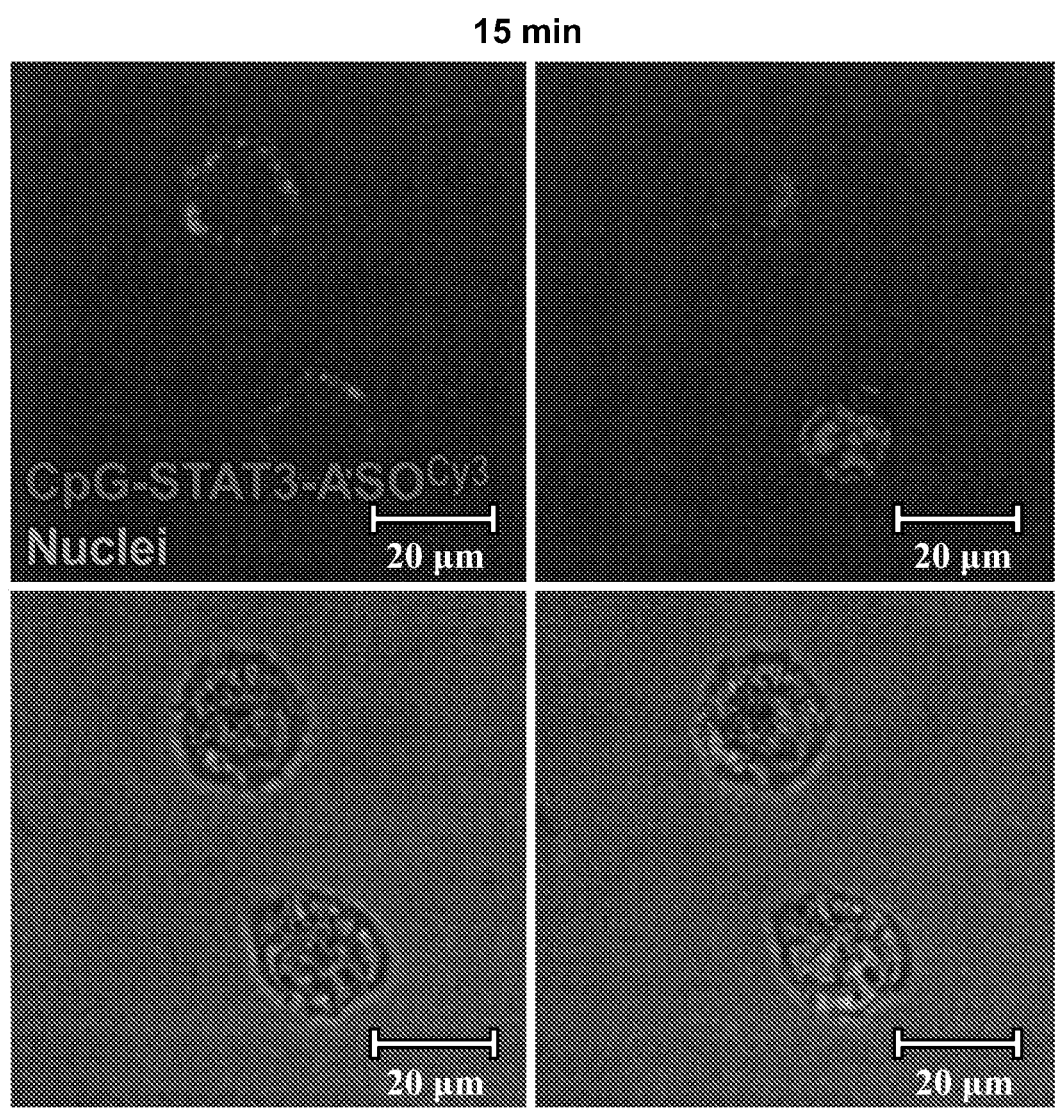
FIGS. 12A-12D shows confocal microscopy images showing the intracellular localization of CpG-STAT3 ASO$^{Cy3}$ after uptake by prostate cancer cells in vitro. DU-145 prostate cancer cells were incubated with 500 nM of fluorescently-labeled CpG-STAT3 ASO$^{Cy3}$ at different times, as indicated (15 min (FIG. 12A) 1 hour (FIG. 12B), 2 hours (FIG. 12C), and 4 hours (FIG. 12D)). The intracellular localization of the conjugate was assessed using confocal microscopy after nuclear staining with DRAQ5®. Representative images from one of two independent experiments are shown.
Figure 12B:
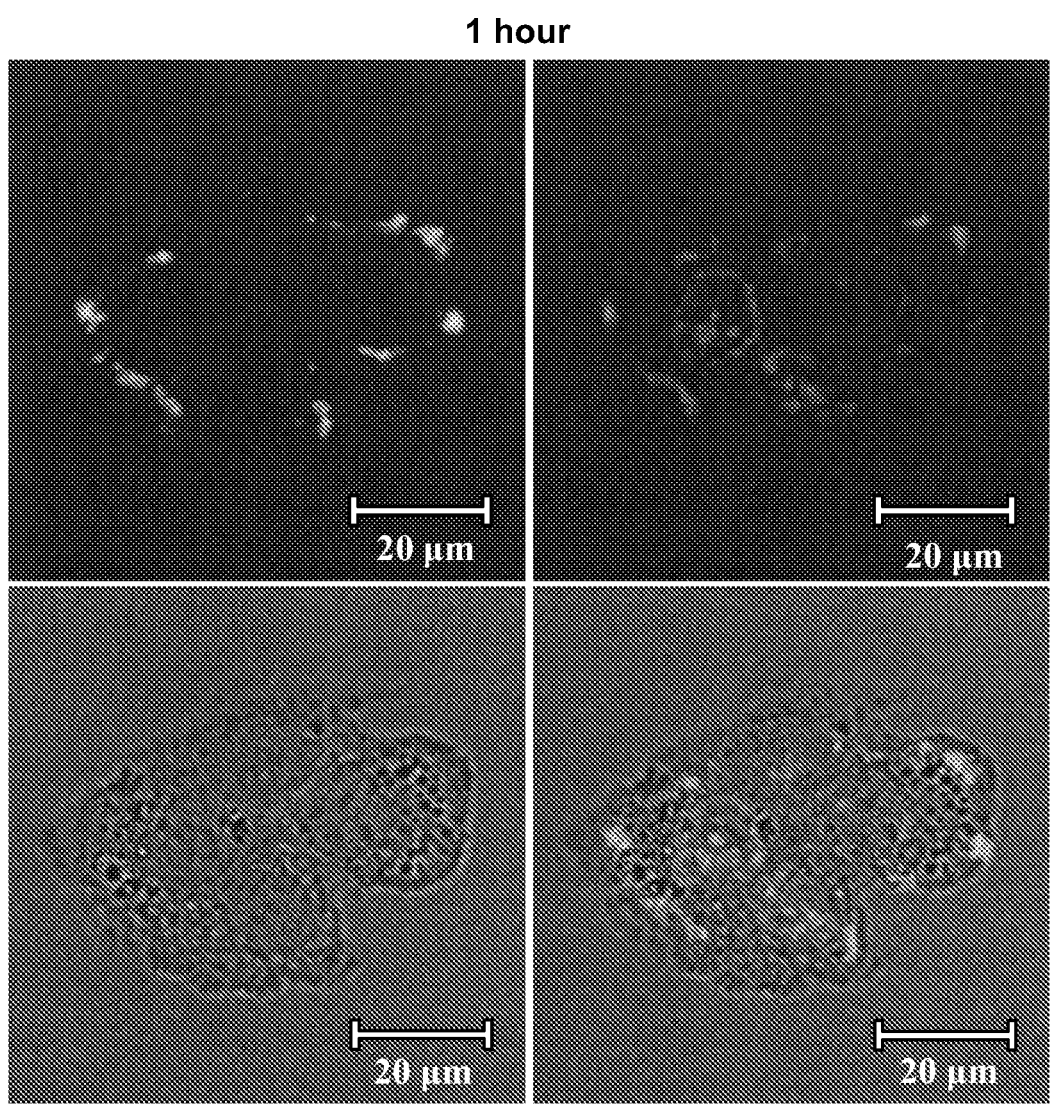
Figure 12C:
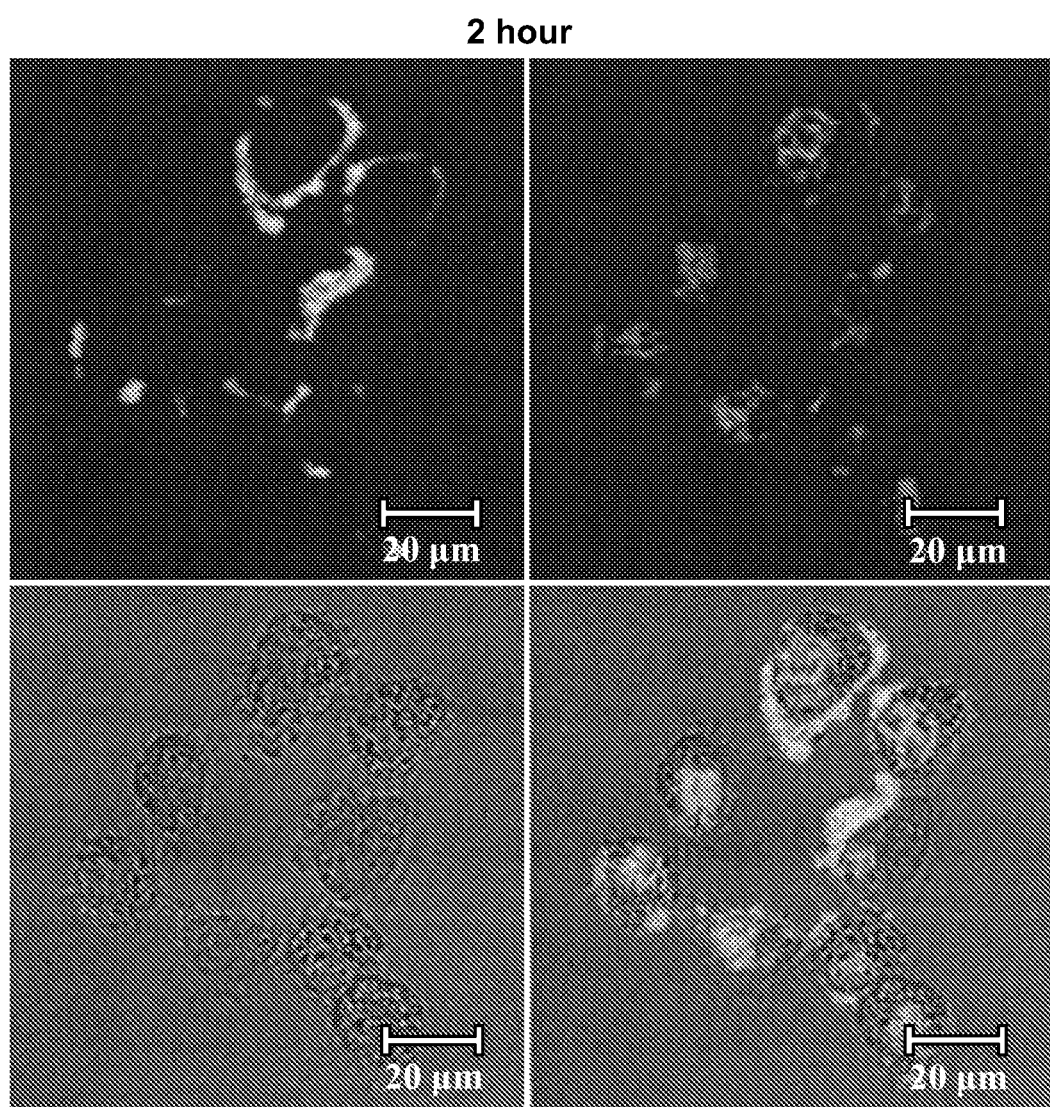
Figure 12D:
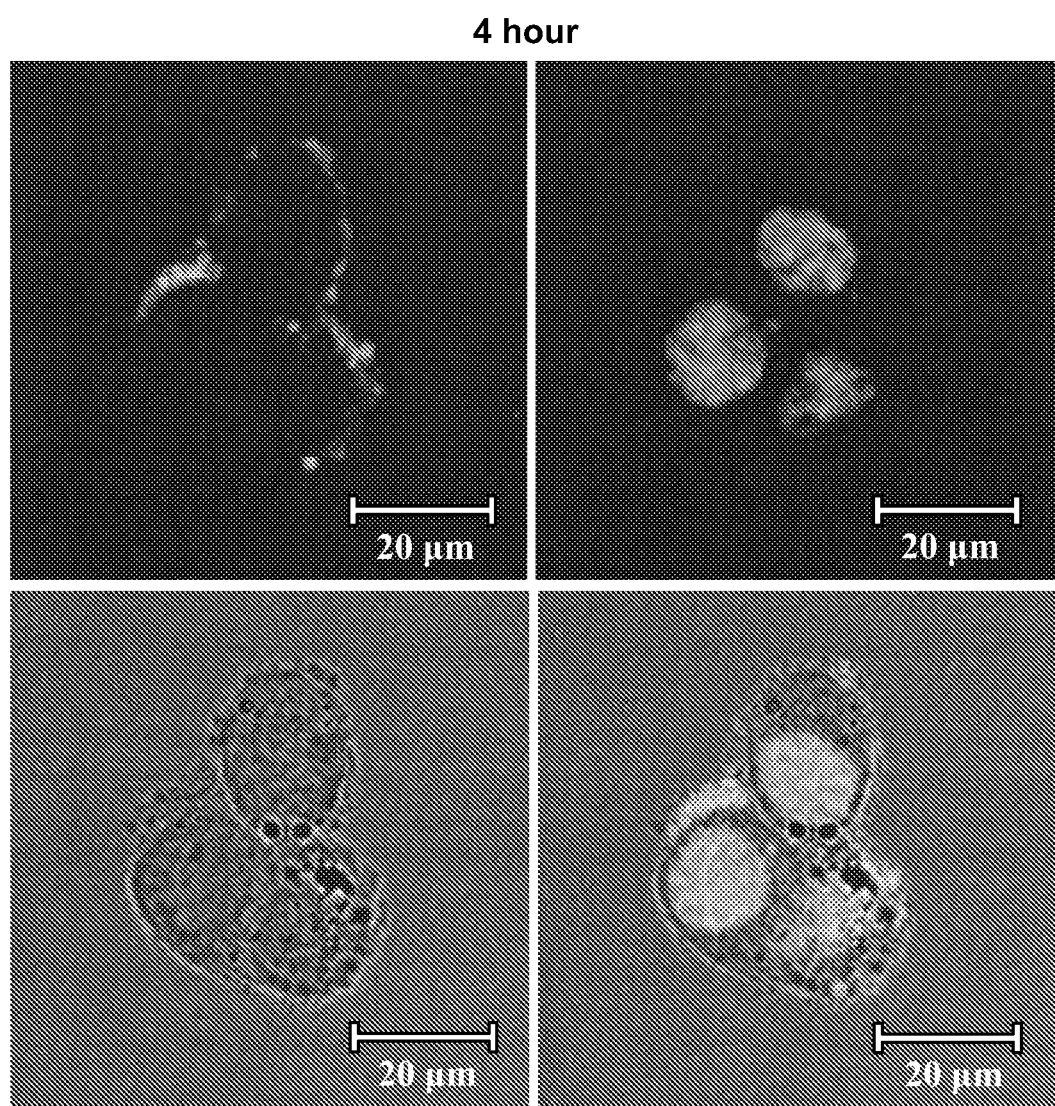
Figure 13A:
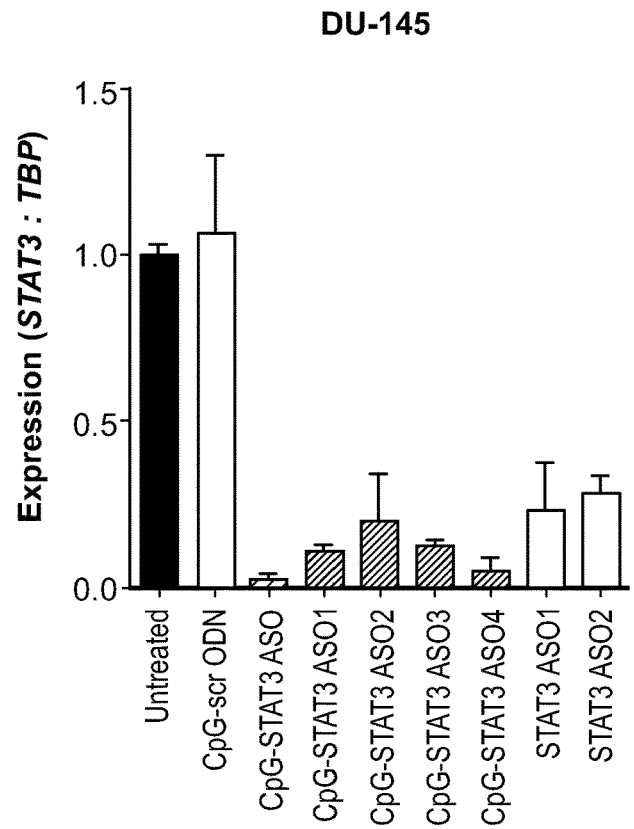
FIGS. 13A-13D are bar graphs and expression data showing that CpG-STAT3 ASO$^{Cy3}$ induced potent STAT3 knockdown in androgen-independent DU-145 (FIG. 13A) and LNCaP-S17 (FIG. 13B) prostate cancer cells. DU-145 (FIG. 13A) and LNCaP-S17 (FIG. 13B) prostate cancer cells were incubated in vitro for 24 hours with 500 nM of various CpG/GpC-STAT3ASOs, unconjugated STAT3ASOs or non-targeting CpG-scrambled ODN. The expression of STAT3 mRNA was measured using quantitative real-time PCR (Taqman; qPCR); results from one of two independent experiments in triplicates; means+/−SD.
Figure 13B:
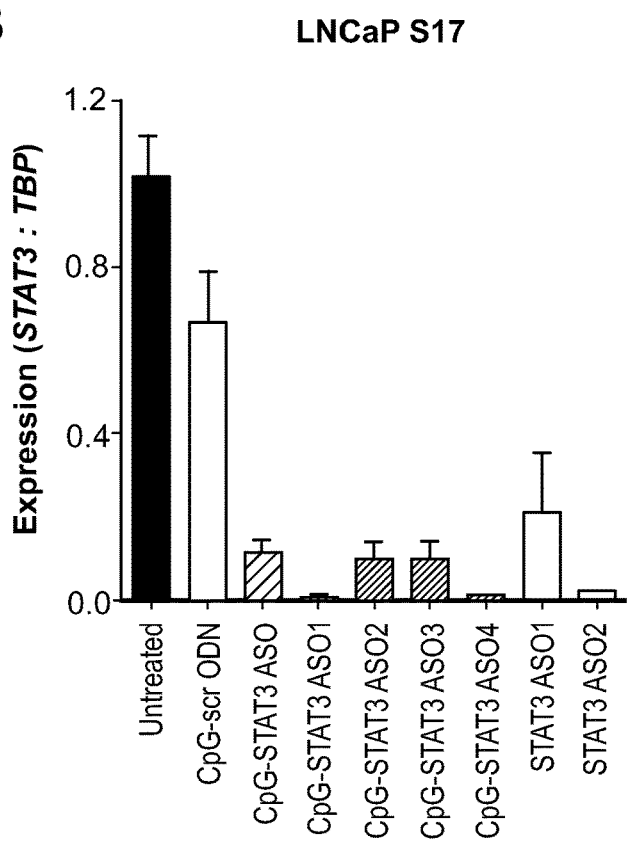
Figure 13C:
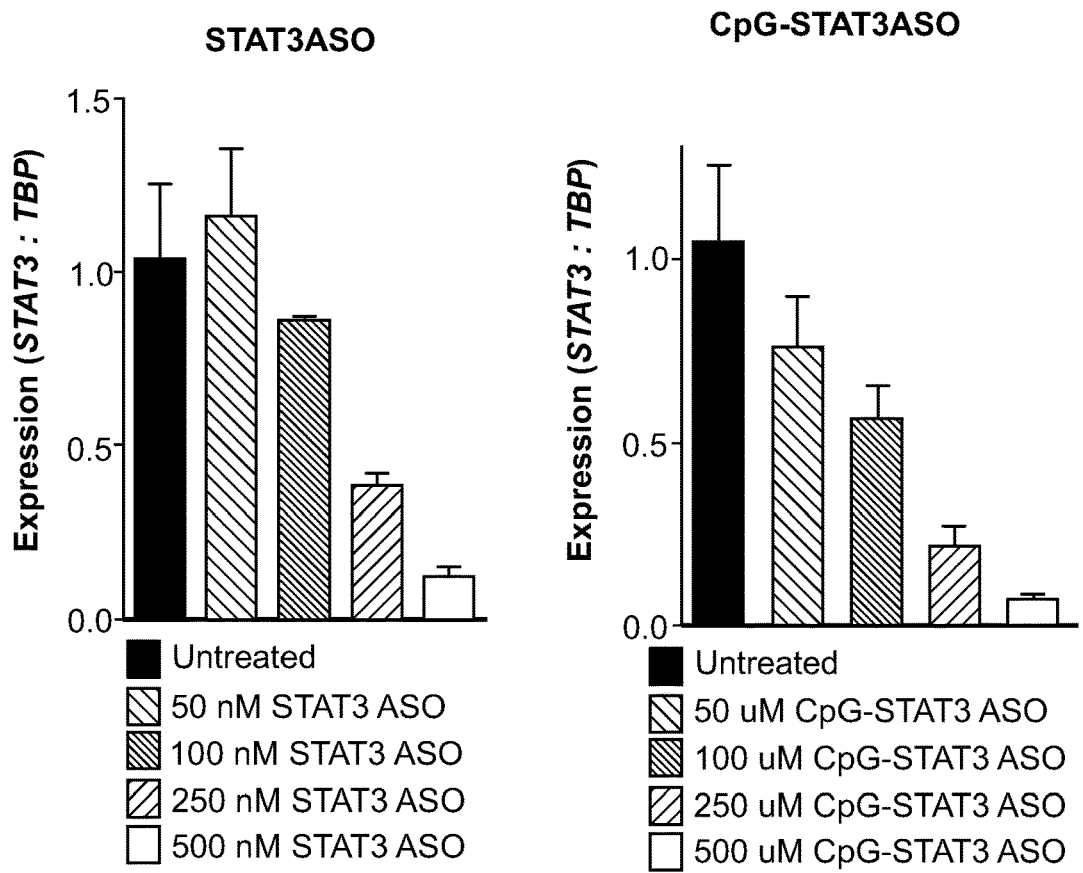
Figure 13D:
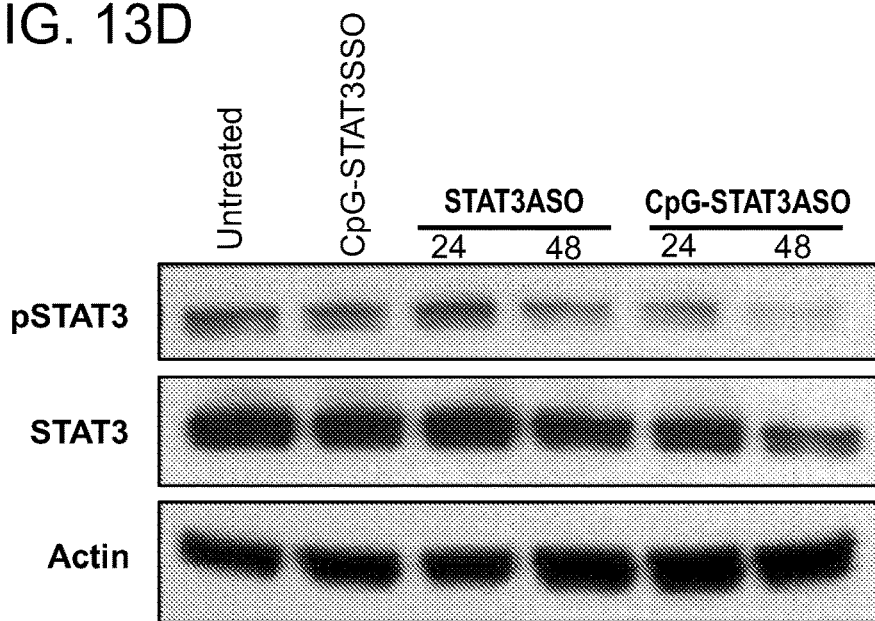
Figure 14A:
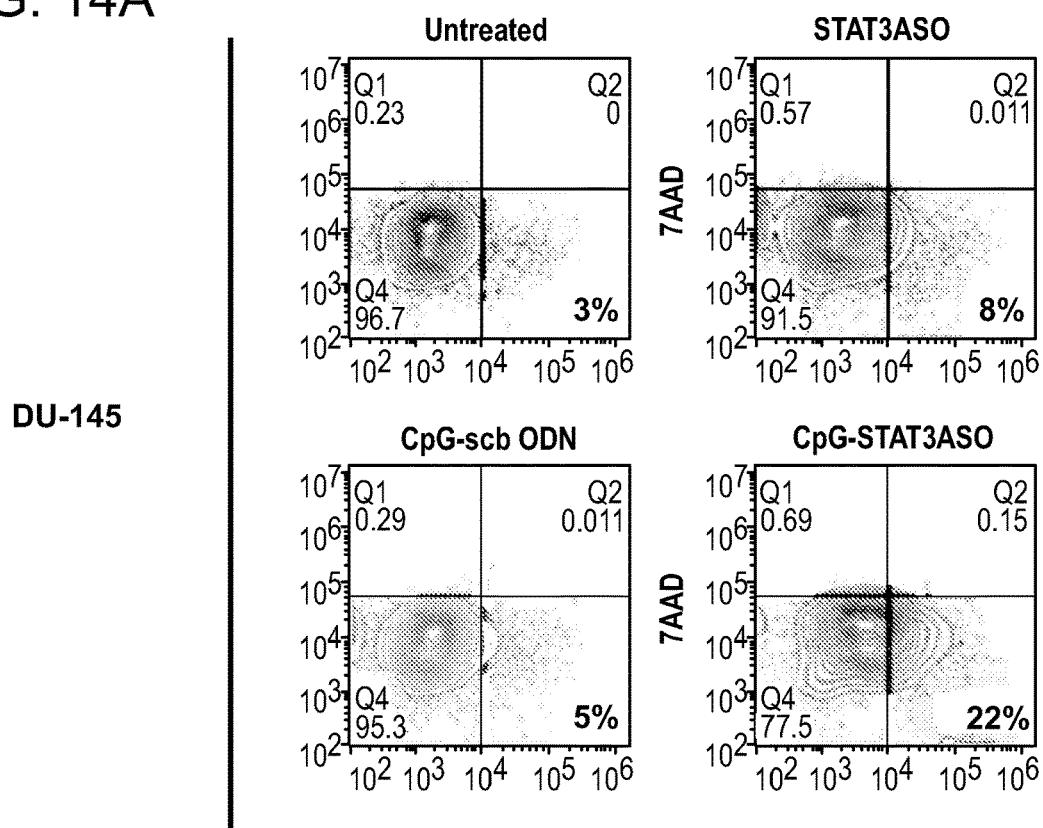
FIGS. 14A-14B are flow cytometry data showing that CpG-STAT3ASO conjugates were more effective than the STAT3ASO alone in the induction of apoptosis in prostate cancer cells in vitro. Cells (DU-145 (FIG. 14A), and LNCaP S17 (FIG. 14B)) were incubated for 24 hours with 500 nM of the CpG-STAT3 ASO conjugate, the STAT3ASO alone or control non-targeting conjugate, CpG-scrambled ODN (CpG-scbODN). The percentages of apoptotic cells were measured using flow cytometry after staining for 7AAD and Annexin V.
Figure 14B:
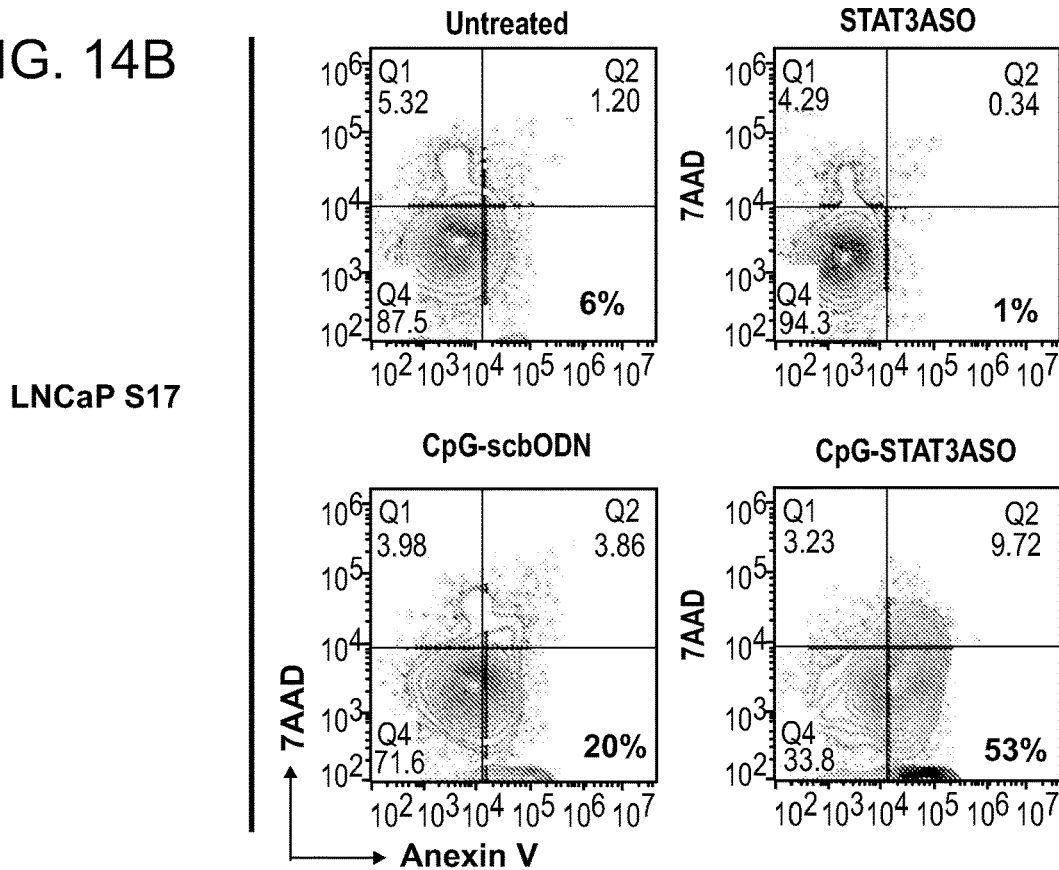
Figure 17A:
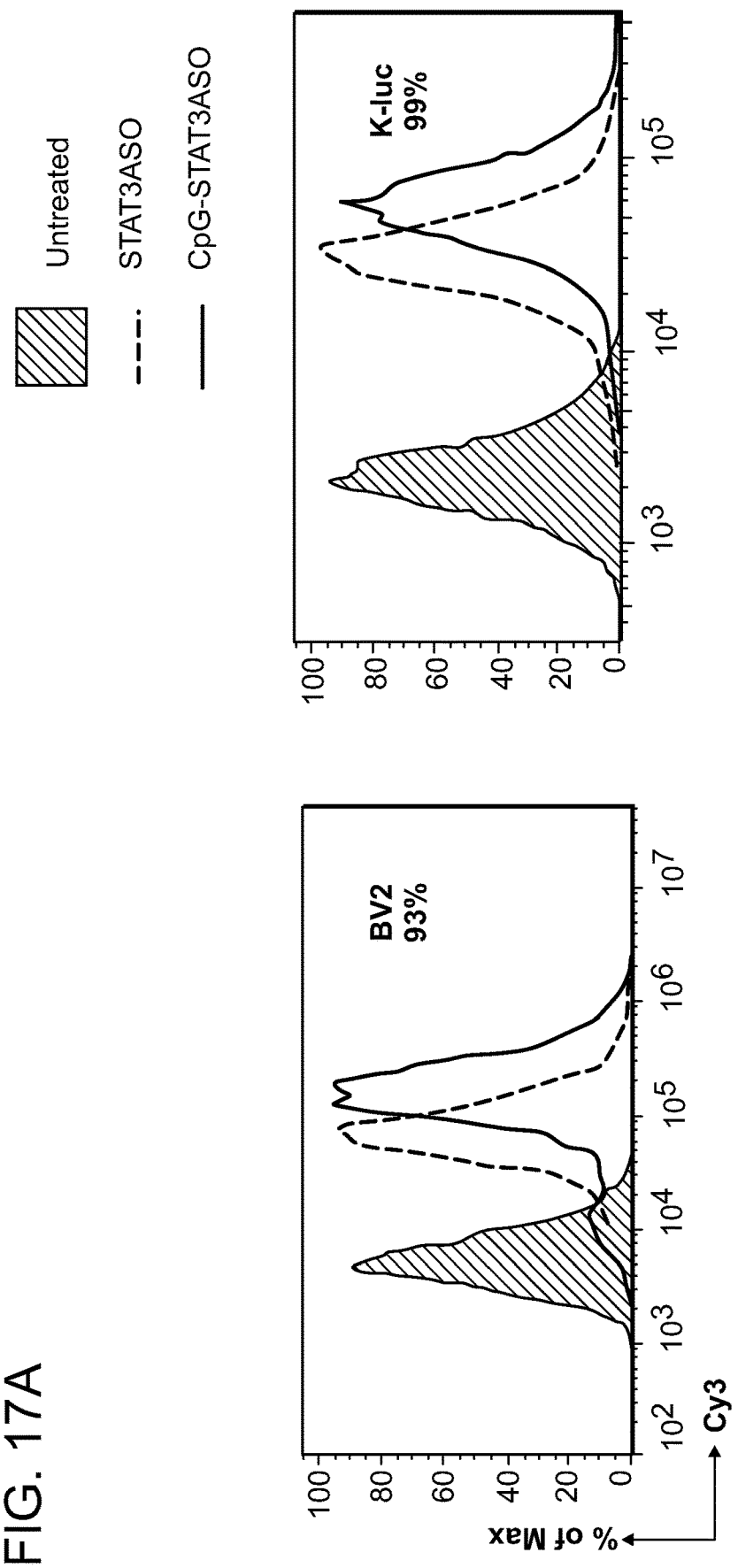
FIGS. 17A-17C are flow cytometry data and bar graphs showing microglia and glioma cell-specific uptake and STAT3 inhibition by CpG-STAT3ASO. Mouse TLR9+ BV2 and K-luc cells (FIG. 17A) and human primary glioma stem-like cells (FIG. 17B) quickly internalize CpG-STAT3ASO and to lesser extent the unconjugated STAT3ASO in vitro (250 nM/1 h). Cells were incubated with 250 nM CpG-STAT3ASO$^{Alexa488}$ or unconjugated STAT3ASO$^{Alexa488}$ for indicated times and percentages of Alexa488-positive cells were measured using flow cytometry.
Figure 17B:
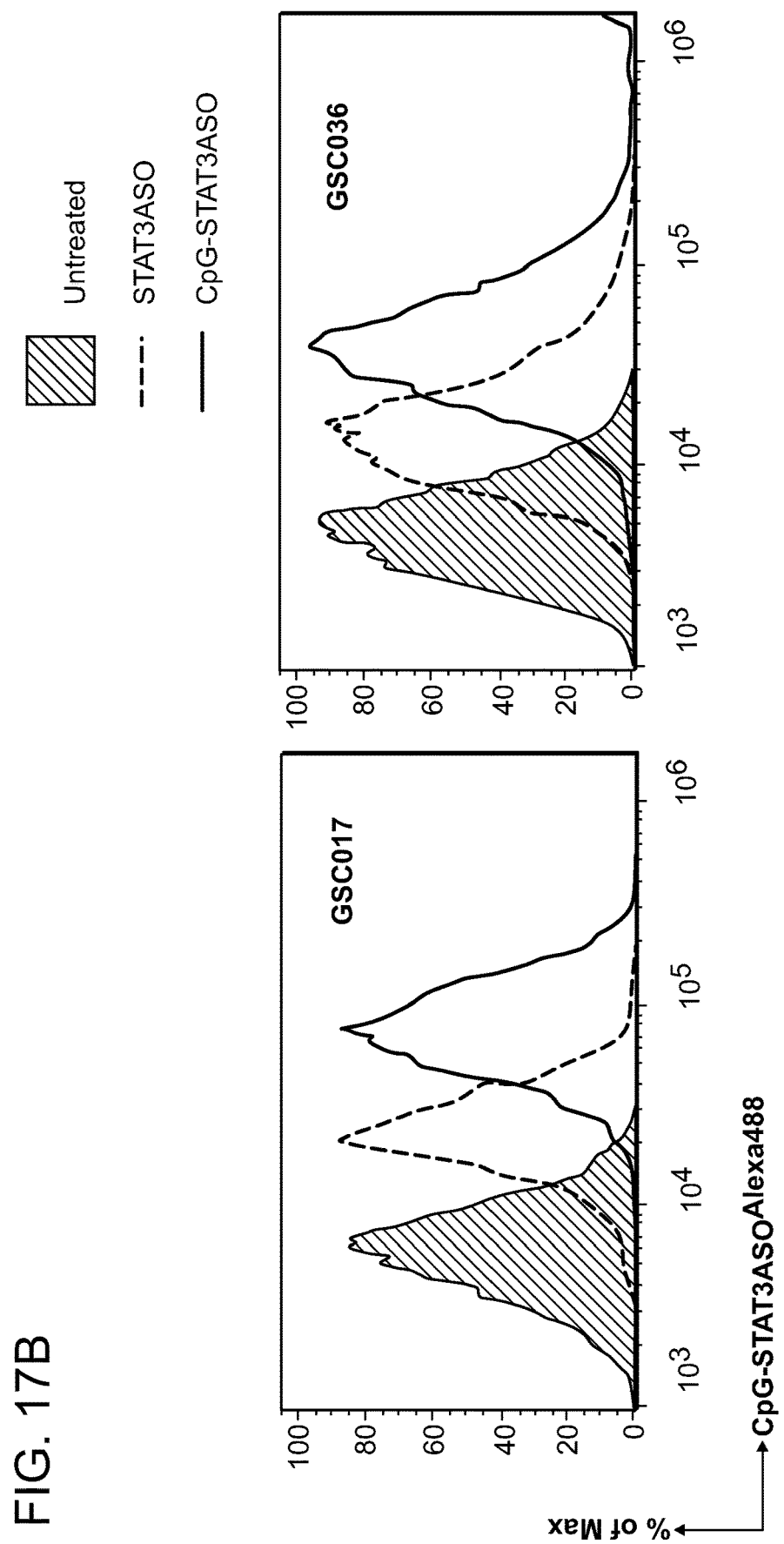
Figure 17C:
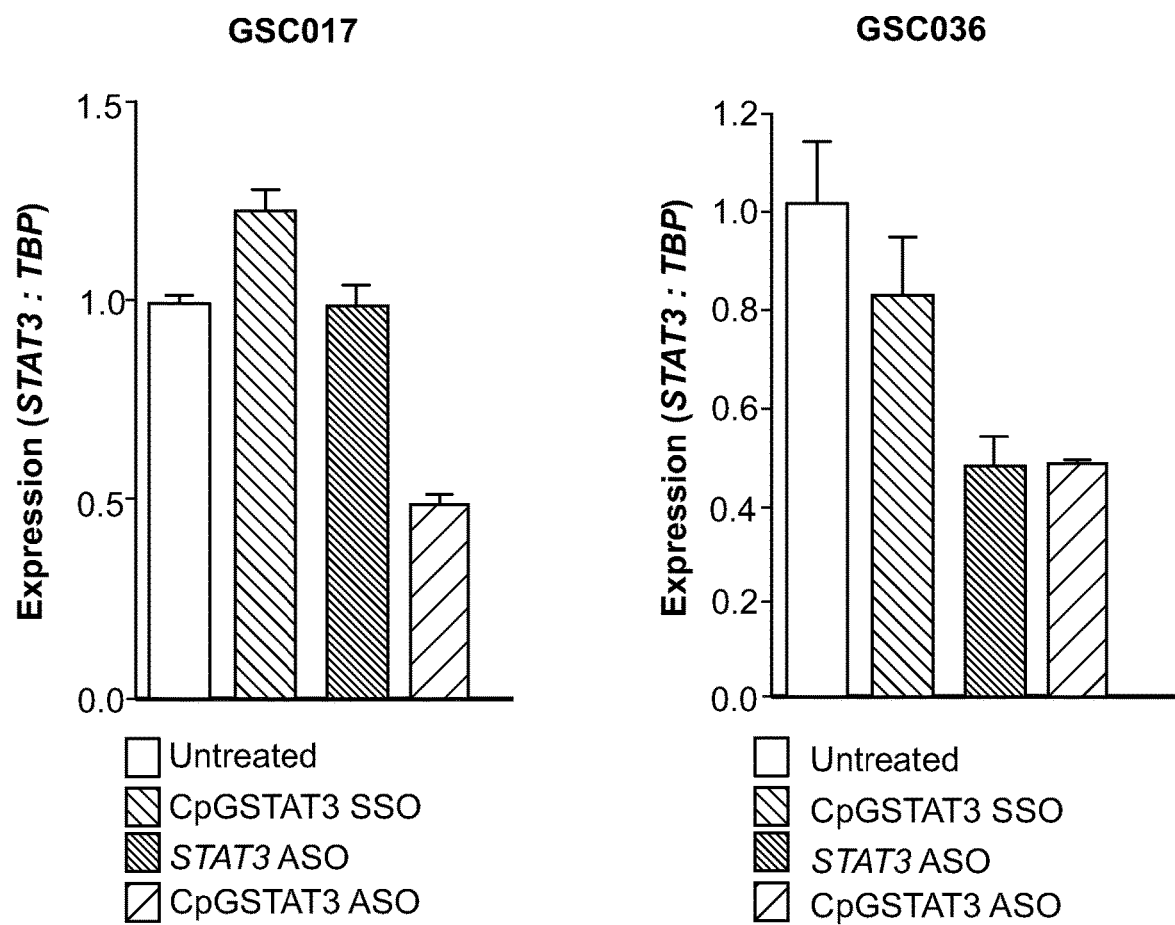

In embodiments, conjugates of CpG oligodeoxynucleotide (ODN), a synthetic TLR9 ligand, with various chemically-modified and nuclease-resistant STAT ASO sequences, e.g., CpG/GpC-ODN-STAT3 ASO, are generated (e.g., SEQ ID NOs: 43-95) (Tables 1, 2, and 4; and FIG. 9A). In embodiments, conjugates of CpG oligodeoxynucleotide (ODN), a synthetic TLR9 ligand, with various chemically-modified and nuclease-resistant STAT ASO sequences, e.g., CpG/GpC-ODN-STAT3 ASO, (e.g., SEQ ID NOs: 43-95) are administered to TLR9+ cells. In embodiments, conjugates of CpG/GpC oligodeoxynucleotide (ODN), a synthetic TLR9 ligand, with various chemically-modified and nuclease-resistant STAT ASO sequences, e.g., CpG/GpC-ODN-STAT3 ASO, (e.g., SEQ ID NOs: 43-95) are administered to subjects. In embodiments, linking the CpG ODN to STAT ASO, e.g., CpG/GpC-ODN-STAT3 ASO, allows for quick internalization by target TLR9$^+$ cells. In embodiments, linking the CpG ODN to STAT ASO, e.g., CpG-ODN-STAT3 ASO, allows for quick internalization by target TLR9+ cells within an hour or less of incubation (e.g., 1 minute, 5 minutes, 10 minutes, 15 minutes, 20 minutes, 25 minutes, 30 minutes, 45 minutes, 50 minutes, 55 minutes or 60 minutes). TLR9+ cells include human and mouse immune cells as well as prostate cancer cells (FIGS. 10A-10B and FIGS. 11A-11B). In embodiments, the uptake of CpG-STAT ASO, e.g., CpG-ODN-STAT3 ASO, (e.g., SEQ ID NOs: 43-60) by human and mouse myeloid immune cells is detectable at a concentration of 50 nM or less (e.g., 1 nM, 5 nM, 10 nM, 15 nM, 20 nM, 25 nM, 30 nM, 35 nM, 40 nM, 45 nm, or 50 nM) (FIGS. 10A-10B and FIGS. 1A-11B). In embodiments, intracellular uptake of CpG-STAT ASO, e.g., CpG/GpC-ODN-STAT3 ASO, (e.g., SEQ ID NOs: 43-95) is verified using confocal microscopy. In embodiments, the conjugate is detectable in the cytoplasm of target cells within 15 min after adding it to culture media (e.g., 30 seconds, 1 minute, 2 minutes, 5 minutes, 10 minutes, 12 minutes, or 15 minutes) (FIGS. 12A-12B). The efficient uptake of these conjugates corresponded to improved efficacy of STAT3 knockdown in DU145 and LNCaP-S17 cells within 24 h of incubation often exceeding the effect of the respective ASO alone (FIGS. 13A-13B). In embodiments, a conjugate of ASO to GpC ODN which does not activate TLR9 (GpC-STAT3 ASO; e.g., SEQ ID NO: 61-77) also strongly inhibits STAT3 expression (FIGS. 13A-13B). In embodiments, CpG-STAT3ASO (e.g., SEQ ID NOs: 43-60) shows more rapid induction of STAT3 knock-down at both mRNA (FIG. 13C) and protein (FIG. 13D) levels compared to the unconjugated STAT3ASO. In embodiments, CpG-STATASO, e.g., CpG-ODN-STAT3 ASO, (e.g., SEQ ID NOs: 43-60, 78-86) internalization and target knock-down is similarly effective in glioma and microglia cells (FIGS. 17A-17C). In embodiments, CpG-STAT ASO conjugate, e.g., CpG-ODN-STAT3 ASO, (e.g., SEQ ID NOs: 43-60), but not STAT3 ASO alone or control CpG-scrambled ODN, induces cell death in cells (FIGS. 14A-14B). In embodiments, CpG-STAT3 ASO conjugate (e.g., SEQ ID NOs: 43-60, 78-86), but not STAT3 ASO alone or control CpG-scrambled ODN, induces cell death in cells within 24 h of culture (e.g., 30 minutes, 1 hour, 1.5 hours, 2 hours, 3 hours, 5 hours, 10 hours, 12 hours, 16 hours, 20 hours, 24 hours). In embodiments, CpG-STAT3 ASO conjugate (e.g., SEQ ID NOs: 43-60, 78-86), but not STAT3 ASO alone or control CpG-scrambled ODN, induces cell death in cells within 24 h of culture in the presence of oligonucleotides. In embodiments, CpG-STAT3 ASO conjugate (e.g., SEQ ID NOs: 43-60, 78-86), but not STAT3 ASO alone or control CpG-scrambled ODN, induces cell death in cells within 24 h of culture in the presence of oligonucleotides at a concentration of 1-1000 nM (e.g., 500 nM). In embodiments, CpG-STAT3 ASO conjugate (e.g., SEQ ID NOs: 43-60, 78-86), but not STAT3 ASO alone or control CpG-scrambled ODN, induces cell death in DU145 and LNCaP-S17 cells within 24 h of culture in the presence of 500 nM of oligonucleotides.

Figure 15C:
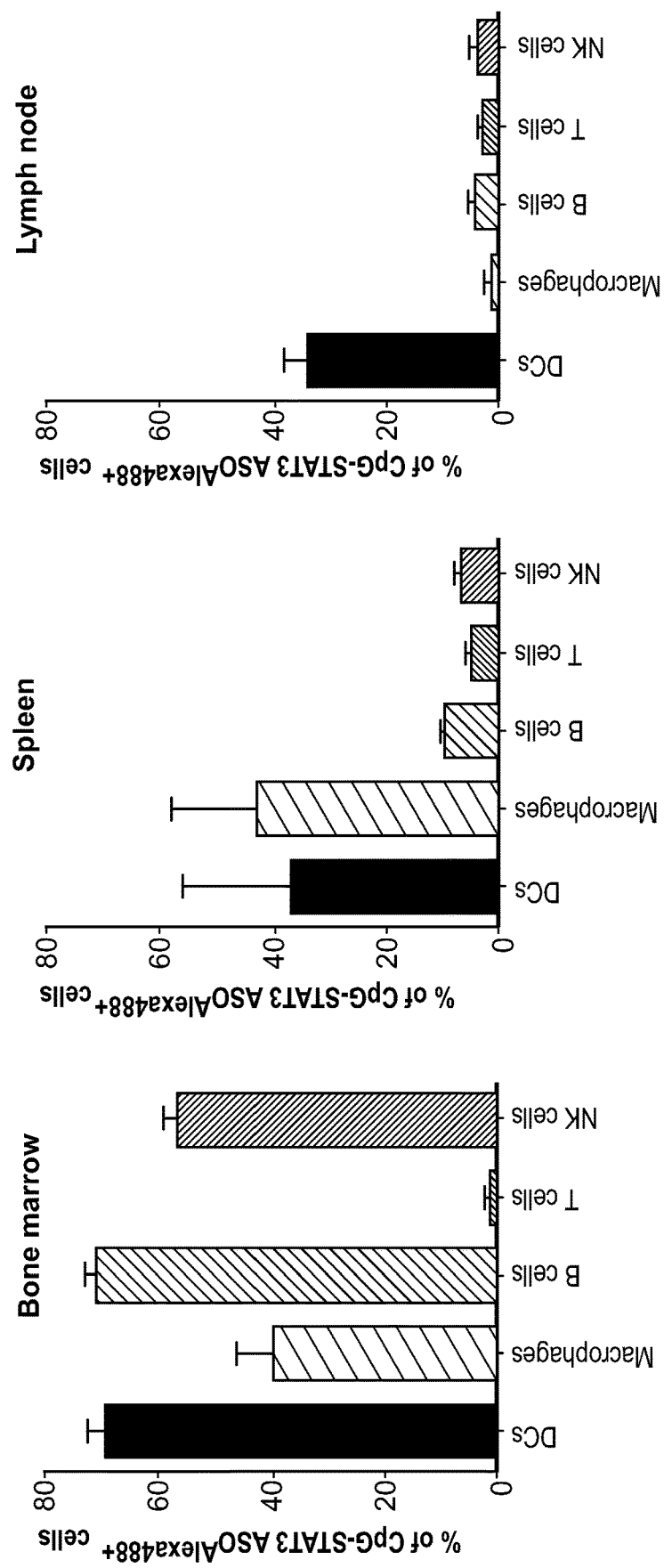
Figure 16A:
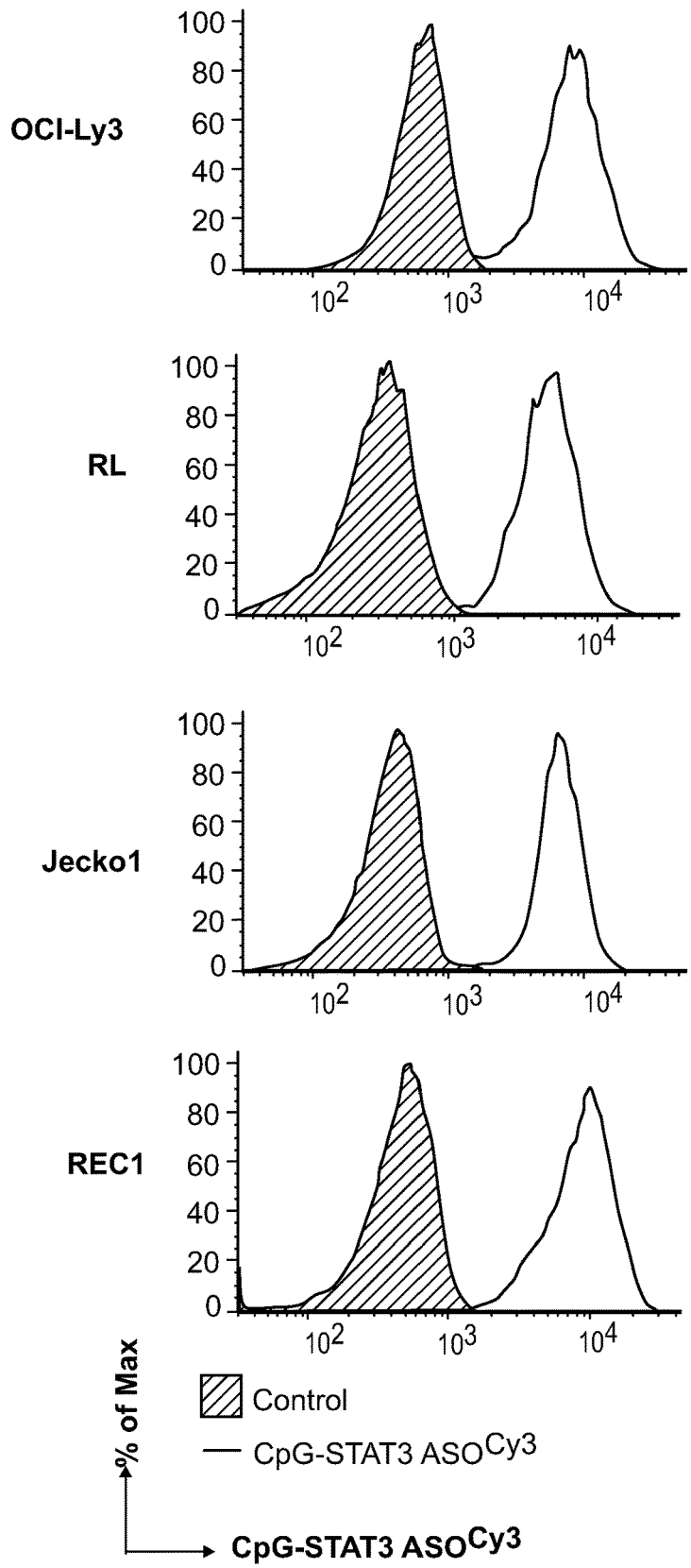
FIGS. 16A-16C are flow cytometry data and bar graphs showing that CpG-STAT3 ASO conjugates effectively targeted STAT3 and reduced viability of TLR+ B cell lymphoma.
Figure 16B:
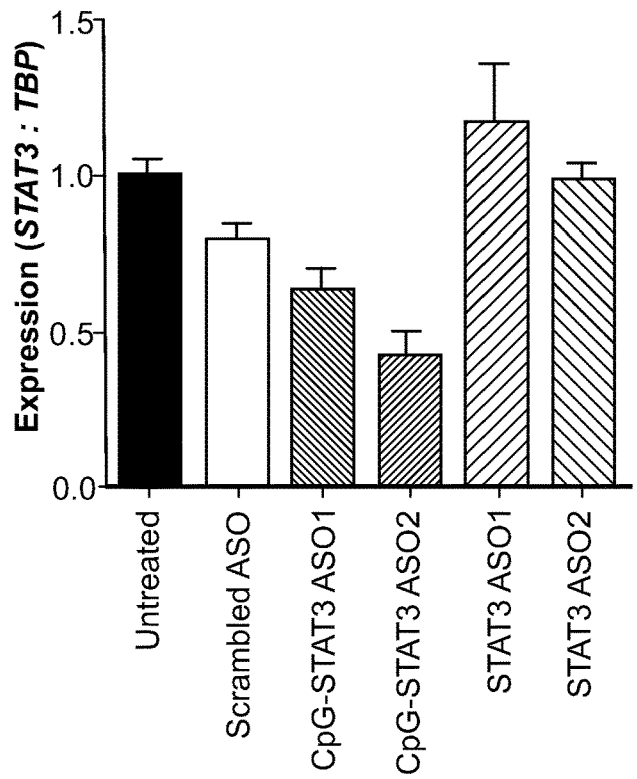
Figure 16C:
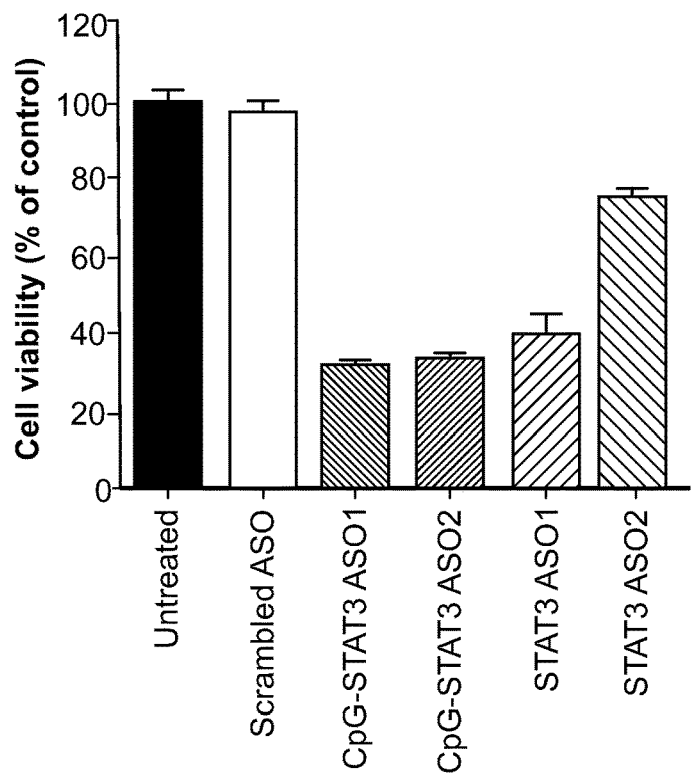
Figure 18A:
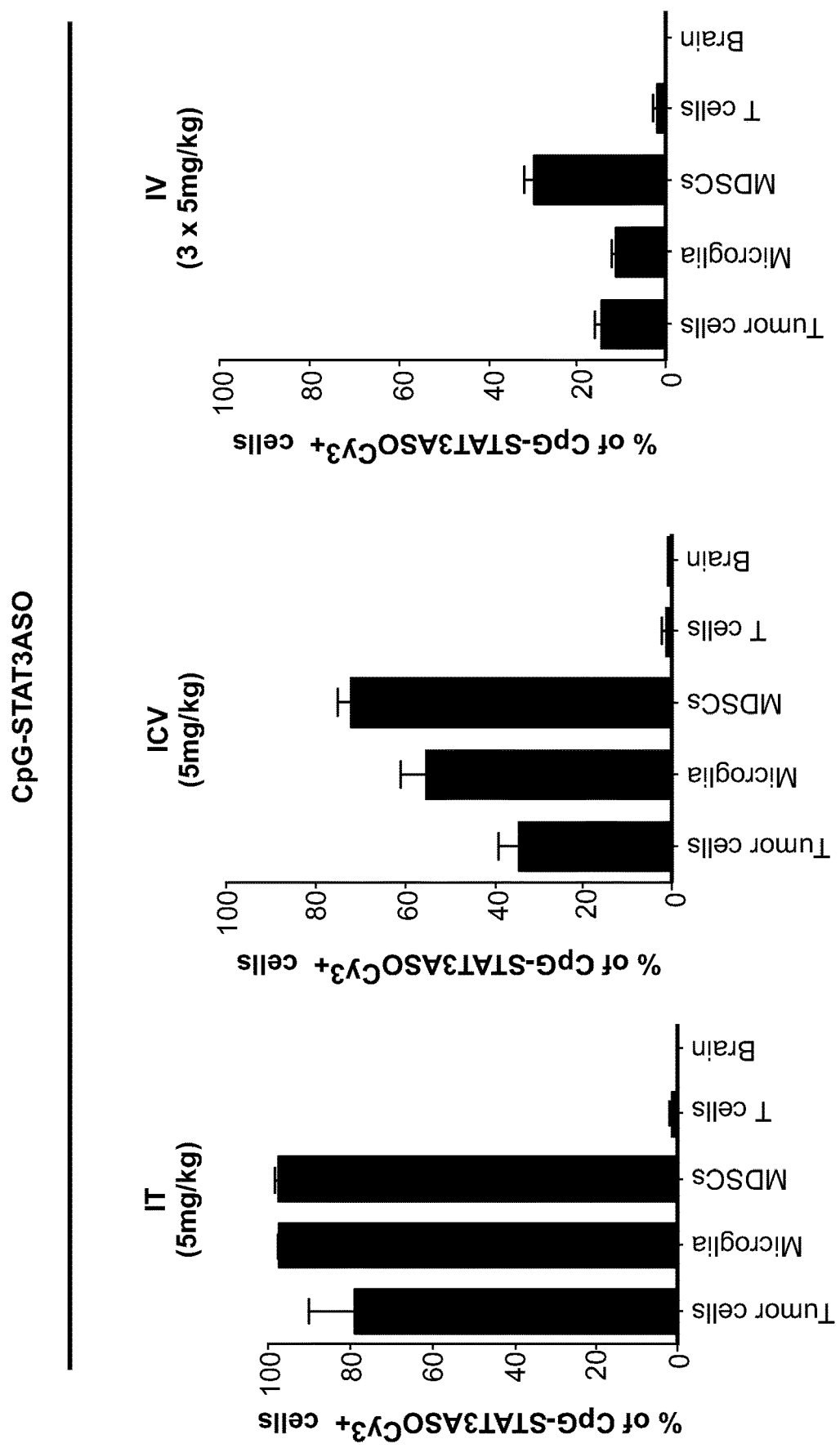
FIGS. 18A-18C are bar graphs and flow cytometry data showing biodistribution of CpG-STAT3 inhibitors in glioma-bearing mice after administration using various routes of delivery.
Figure 18B:
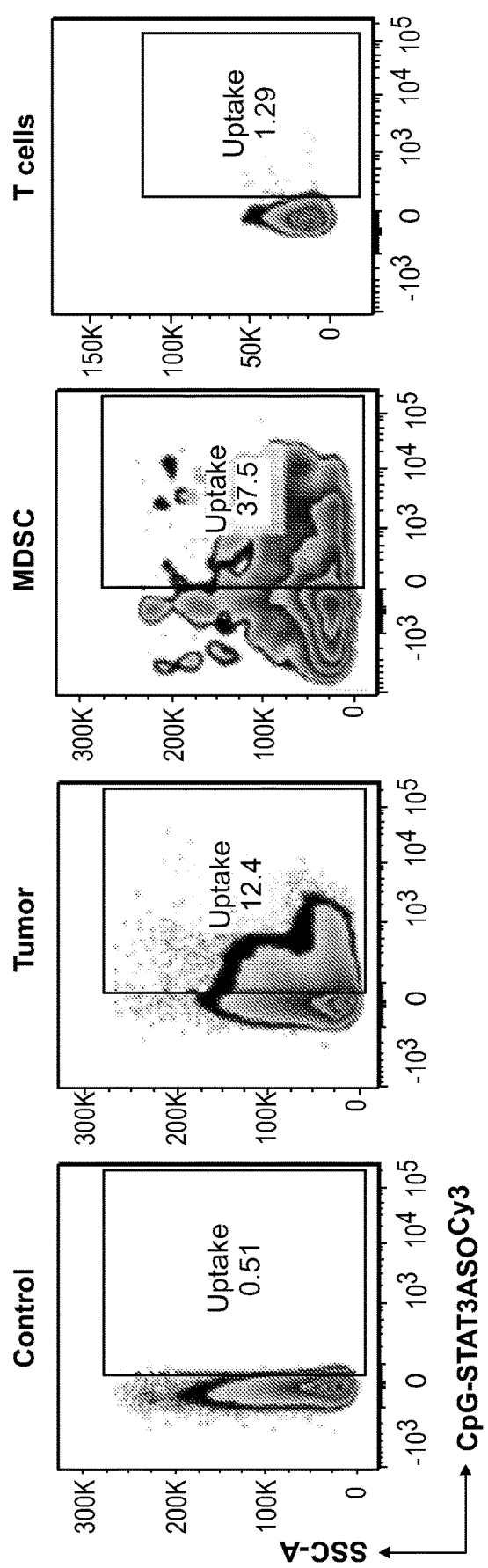
Figure 18C:
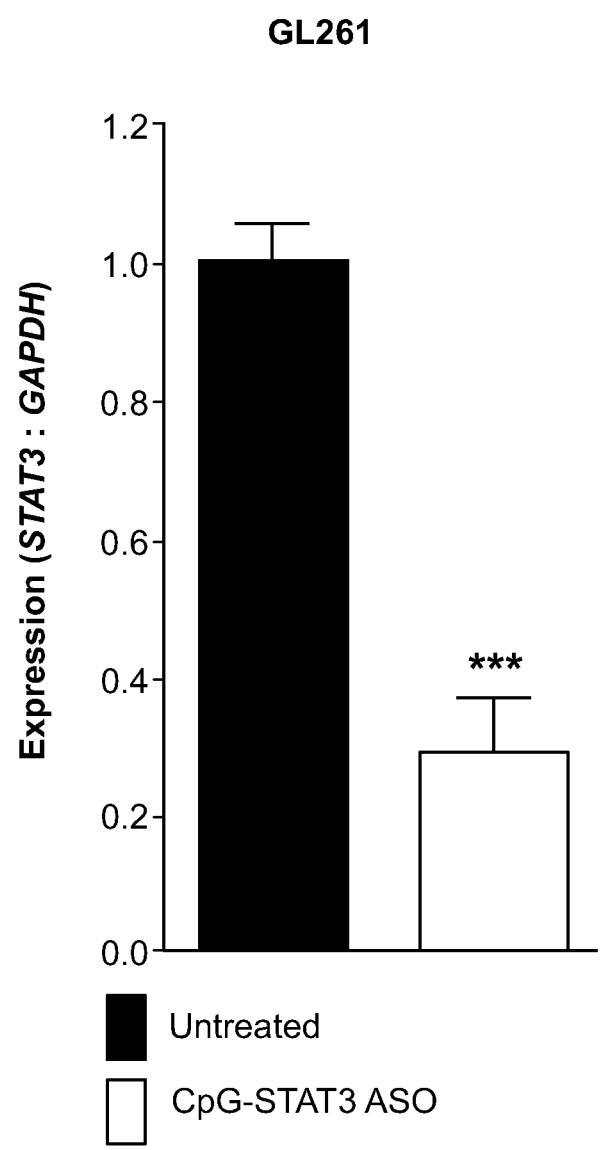
Figure 19A:
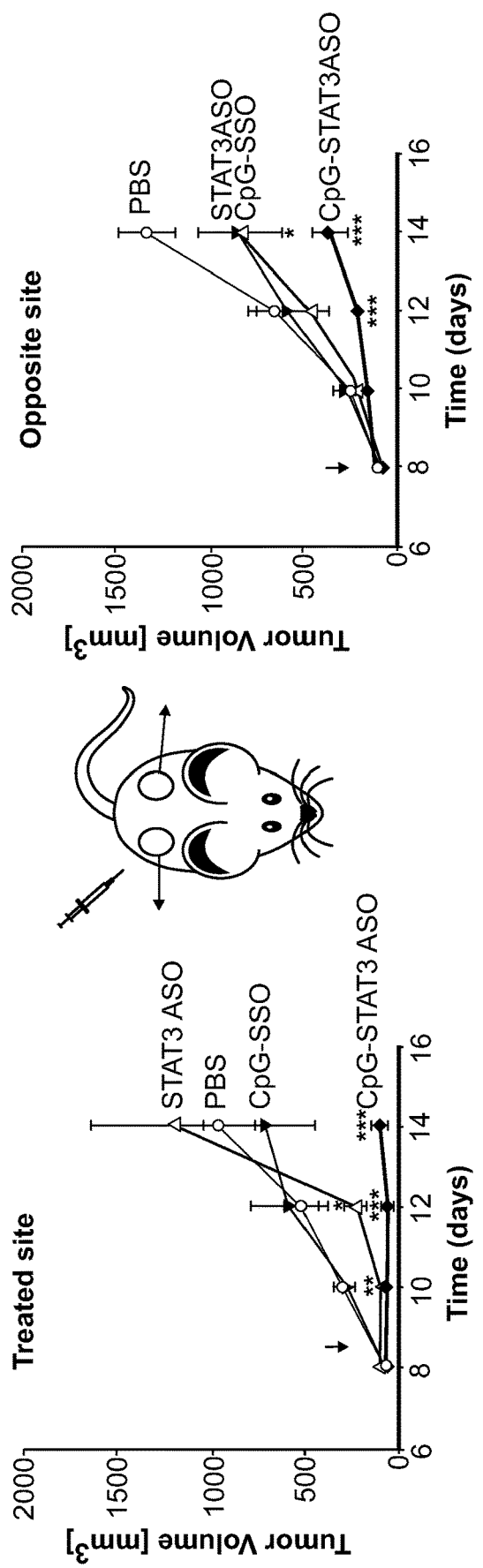
Figure 19B:
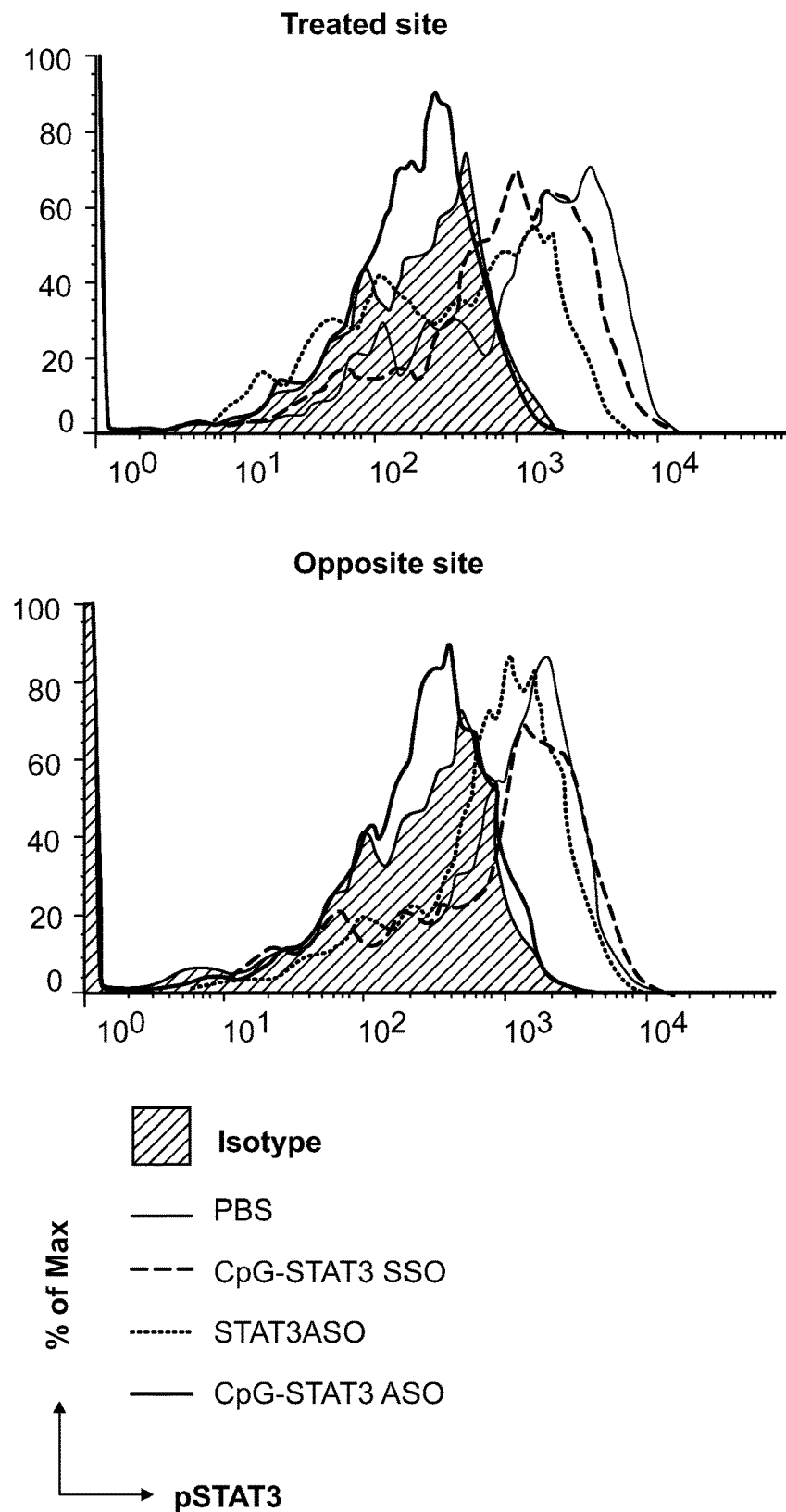
Figure 19C:
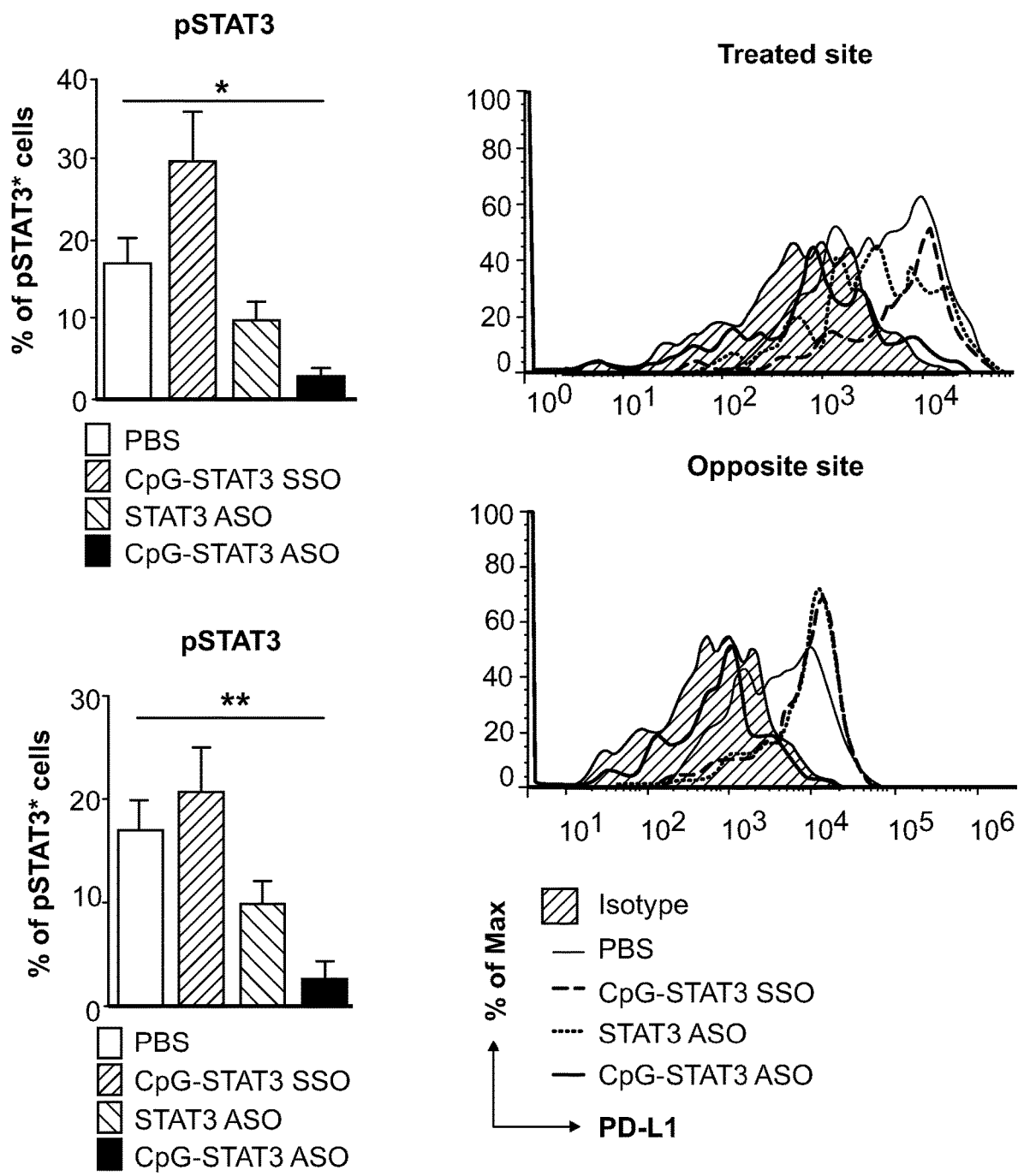
Figures 20A, 20B:
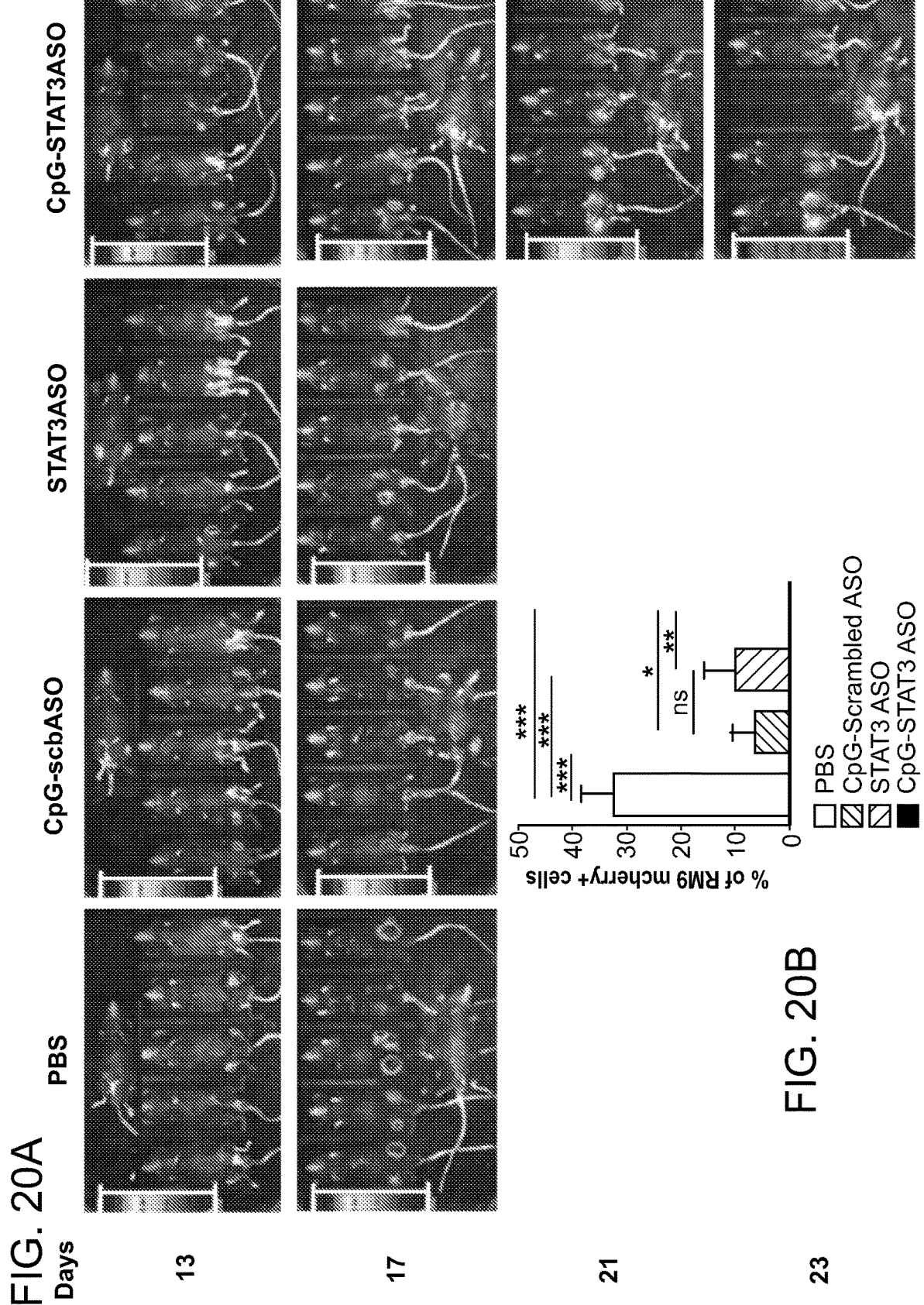
FIGS. 20A-20B are images (FIG. 20A) and flow cytometry data (FIG. 20B) showing that intravenous administration of the CpG-STAT3ASO results in complete regression of the experimental bone metastatic model of RM9 prostate cancer. RM9 prostate cancer cells were injected intratibially in C57BL/6 mice. Animals with established tumors were treated using daily i.v. injections 5 mg/kg of CpG-STAT3 ASO conjugated, STAT3 ASO alone or CpG-scrambled ASO for up to 15 days. Tumor burden and mice condition were monitored using the bioluminescent imaging (BLI) on AmiX (Spectral) imaging system or body condition scoring (BCS), respectively (FIG. 20A). Graphic shows the percentages of RM9 mcherry+ cells (FIG. 20B) in the bone marrow assessed using flow cytometry at the end of the experiment or at the time when the mice had to be euthanized (BCS<2); mean±SEM (n=6).
Figure 21:
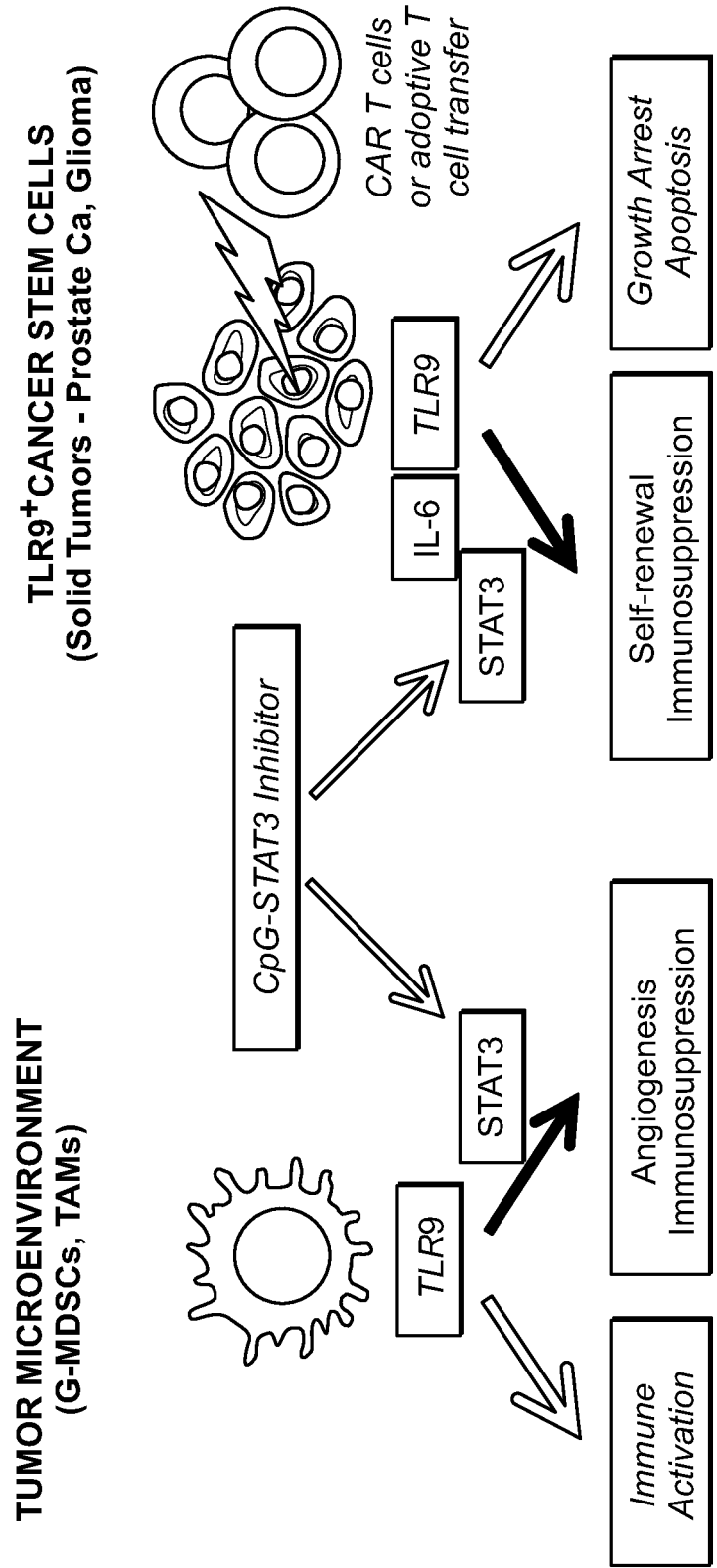
FIG. 21 shows that the two pronged action of CpG-STAT3ASO inhibitors can augment therapeutic efficacy of human cancer immunotherapies. TLR9 is expressed not only by tumor-associated myeloid cells (macrophages, microglia and G-MDSCs) but also certain cancer cells (tumor-propagating cells). Treatment-induced cancer cell death (e.g. after CAR T cell treatment or radiation therapy) leads to release of TLR9 ligands, which indirectly activating STAT3 in the tumor microenvironment. TLR9/STAT3 signaling inhibits macrophages/microglia differentiation, while stimulating angiogenesis and suppressing immune responses. In addition, STAT3 activation in tumor-propagating cells supports cancer self-renewal and resistance to therapies. CSIs allows for targeting of STAT3 in both TLR9+ cell compartments thereby enhancing overall therapeutic efficacy.

In embodiments, improved nuclease-resistance of CpG-ASOs (e.g., SEQ ID NOs: 61-95), allows for systemic administration and targeting of TLR9$^+$ cells (FIGS. 15A-15C, and FIGS. 18A-18C). In embodiments, improved nuclease-resistance of CpG-ASOs (e.g., SEQ ID NOs: 43-60, 78-86), allows for systemic administration and targeting of TLR9+ cells in distant organs (e.g., spleen or bone marrow). In embodiments, a single intravenous (IV) injection of fluorescently-labeled CpG-STAT3ASO (e.g., SEQ ID NOs: 43-60, 78-86) is sufficient to deliver conjugate to a majority of myeloid cells (FIGS. 15A-15C). In embodiments, a single intravenous (IV) injection of fluorescently-labeled CpG-STAT3ASO (e.g., SEQ ID NOs: 43-60, 78-86) is sufficient to deliver to 50% or more of myeloid cells in the bone marrow (e.g., 50%, 55%, 60%, 65%, 70%, 75%, 80%, 85%, 90%, 95%, 99% or more). In embodiments, a single intravenous (IV) injection of fluorescently-labeled CpG-STAT3ASO (e.g., SEQ ID NOs: 43-60, 78-86) is sufficient to deliver to a significant proportion of myeloid cells (e.g., 25%, 30%, 35%, 40%, 45%, 50% or more) in peripheral lymph nodes, including dendritic cells. In embodiments, administration of repeated (e.g., more than one) IV injections of CpG-STAT3ASO (e.g., SEQ ID NOs: 43-60, 78-86) allows for penetration of significant fraction of myeloid cells (e.g., 20%, 25%, or 30% of MDSCs) in brain localized glioma tumors (FIGS. 18A-18C). In embodiments, administration of a single local IV injection of CpG-STAT3ASO (e.g., SEQ ID NOs: 43-60, 78-86) allows for almost complete penetration (e.g., 75%, 80%, 85%, 90%, 95%, 99.5) of the tumor microenvironment. In embodiments, administration of CpG-STAT3ASO (e.g., SEQ ID NOs: 43-60, 78-86) is utilized against TLR9$^+$ malignancies. In embodiments, CpG-STAT3ASO (e.g., SEQ ID NOs: 43-60, 78-86) enhances target gene knock down and cytotoxicity (FIGS. 16A-16C). In embodiments, CpG-STAT3ASO (e.g., SEQ ID NOs: 43-60, 78-86) reduces tumor size in distant untreated locations (FIG. 19A). In embodiments, reduction of STAT3 expression in a distant site correlates with a systemic effect of CpG-STAT3ASO (e.g., SEQ ID NOs: 43-60, 78-86) release from an injection site (FIG. 19B and FIG. 19E). In embodiments, treatment using CpG-STAT3ASO (e.g., SEQ ID NOs: 43-60, 78-86) reduces expression of STAT3 and PD-L1 immune checkpoint molecules (FIGS. 19C-19D). In embodiments, treatment using CpG-STAT3ASO (e.g., SEQ ID NOs: 43-60, 78-86) reduces expression of STAT3 and PD-L1 immune checkpoint molecules in myeloid-derived suppressor cells (MDSCs) at the distant tumor site. In embodiments, CpG-STAT3ASO (e.g., SEQ ID NOs: 43-60, 78-86) is administered systemically (FIGS. 20A-20B). In embodiments, the administration route of CpG-STAT3ASO (e.g., SEQ ID NOs: 43-60, 78-86) may be IP (intra-peritoneal); PO (per-oral); or IV (intra-venous). In embodiments, the administration route is transdermal, subcutaneous, intra-muscular, intra-thecal, intra-ocular, intranasal, transmucosal, sublabial, insufflation, enteral, suppository, intra-arterial, intra-articular, intra-cerebral, intra-cranial, intravitreal, or intratibial. In embodiments, subjects are treated using daily intravenous injections of 0.5 mg/kg to 5 mg/kg of CpG-STAT3ASO (e.g., SEQ ID NOs: 43-60, 78-86). In embodiments, CpG-STAT3ASO (e.g., SEQ ID NOs: 43-60, 78-86) treatment induces complete regression of tumors. In embodiments, CpG-STAT3ASO (e.g., SEQ ID NOs: 61-95) treatment induces complete regression of localized tumors (e.g., bone, spleen, bladder, pancreas, testis, ovary, prostate, uterus, colon, lymph node, lung, brain, kidney, liver, stomach, large intestines, small intestines, esophagus, spine, head, neck, skin, or heart). In embodiments, nuclease-resistant CpG-STAT3 ASO inhibitors allow for simultaneous targeting of STAT3 signaling in disseminated TLR9$^+$ cells and in tolerogenic tumor-associated cells (FIG. 21). In embodiments, nuclease-resistant CpG-STAT3 ASO inhibitors allow for simultaneous targeting of STAT3 signaling in disseminated TLR9+ prostate cancer cells and in tolerogenic tumor-associated immune cells (e.g., macrophages, microglia, T cells, B cells, or MDSCs). In embodiments, disruption of signaling cross talk within the tumor microenvironment is effective in treating cancer.

Method of Treating Autoimmune Disease and/or Disorder

In one aspect, the present disclosure includes a method of treating an autoimmune disease and/or disorder with a compound and/or composition of the disclosure, without inducing an immunogenic effect. In embodiments, the method includes suppressing of a gene in myeloid cells with a compound and/or composition of the disclosure, without inducing an immunogenic effect. In embodiments, the myeloid cells are in a tumor microenvironment, involved in autoimmune disease and/or disorder, or in cancer (e.g., prostate cancer).

In embodiments, the method includes treating an autoimmune disease and/or disorder (e.g., rheumatoid arthritis, Crohn's disease, ulcerative colitis, multiple sclerosis, psoriasis, systemic lupus erythematosus (SLE)), with a compound and/or composition of the disclosure, without inducing an immunogenic effect. In embodiments, the method includes suppressing of a gene in myeloid cells with a compound and/or composition of the disclosure, without inducing an immunogenic effect.

The present disclosure provides a method of treating an autoimmune disease (e.g., rheumatoid arthritis, Crohn's disease, ulcerative colitis, multiple sclerosis, psoriasis, systemic lupus erythematosus (SLE)) without stimulating an immune response in a subject in need thereof, the method including administering to the subject an effective amount of a compound or a pharmaceutical composition including a compound of, e.g., one of SEQ ID NOs: 29-30 linked to, e.g., one of STAT ASOs of SEQ ID NOs: 31-42 and 110-113.

The present disclosure provides a method of treating an autoimmune disease (e.g., rheumatoid arthritis, Crohn's disease, ulcerative colitis, multiple sclerosis, psoriasis, systemic lupus erythematosus (SLE)), without simultaneously inducing an immune response, including contacting the cell with an effective amount of a compound or a pharmaceutical composition of, e.g., one of SEQ ID NOs: 29-30 linked to, e.g., one of SEQ ID NOs: 31-42 and 110-113. In embodiments, the present disclosure provides a method of treating an autoimmune disease (e.g., rheumatoid arthritis, Crohn's disease, ulcerative colitis, multiple sclerosis, psoriasis, systemic lupus erythematosus (SLE)), inhibiting uncontrolled cell growth and/or proliferation, and/or reducing activity of STAT transcription factor in a cell, e.g., a STAT1-STAT5, without inducing immune response, with a compound of, e.g., one of SEQ ID NOs: 29-30 linked to, e.g., one of SEQ ID NOs: 31-42 and 110-113. For example, the method of includes administering a compound of, e.g., SEQ ID NOs: 61-95, which do not induce immune response.

In embodiments, the present disclosure provides a method of treating Crohn's disease, without simultaneously inducing an immune response, including contacting the cell with an effective amount of a compound or a pharmaceutical composition of, e.g., one of SEQ ID NOs: 29-30 linked to, e.g., one of SEQ ID NOs: 31-42 and 110-113. In embodiments, the present disclosure provides a method of treating Crohn's disease, without inducing immune response, with a compound of, e.g., one of SEQ ID NOs: 29-30 linked to, e.g., one of SEQ ID NOs: 31-42 and 110-113. For example, the method of includes administering a compound of, e.g., SEQ ID NOs: 61-95, which do not induce immune response.

Method of Treating Paraplegia

In one aspect, the present disclosure includes a method of treating paraplegia in a subject in need thereof, by administering a compound and/or composition of the disclosure, with or without inducing an immunogenic effect. In embodiments, the method includes suppressing of a gene in mesenchymal stem cells (MSCs) with a compound and/or composition of the disclosure, with or without inducing an immunogenic effect.

The present disclosure provides a method of treating paraplegia without stimulating an immune response in a subject in need thereof, the method including administering to the subject an effective amount of a compound or a pharmaceutical composition including a compound of, e.g., one of SEQ ID NOs: 29-30 linked to, e.g., one of STAT ASOs of SEQ ID NOs: 31-42 and 110-113.

The present disclosure provides a method of treating paraplegia, while simultaneously inducing an immune response, with an effective amount of a compound or a pharmaceutical composition of phosphorothioated oligodeoxynucleotides (ODN) of, e.g., one of SEQ ID NOs: 7-18 and 98-101 linked to, e.g., one of SEQ ID NOs: 31-42 and 110-113.

Method of Synthesis and Modification of Linkers

In embodiments, CpG-CEBPA saRNA (SS, sense strand) and CEBPA saRNA (AS, antisense strand) may be synthesized using a cycle including four steps. After the complete synthesis, deprotection, purification and desalting of CpG-CEBPA saRNA (SS) and CEBPA saRNA (AS), the two components may be annealed to produce a compound of the present disclosure CpG-CEBPA saRNA (SS/AS).

The starting point of the synthesis may be a protected nucleoside linked via its 3'-oxygen to a polystyrene-based solid support. Nucleoside phosphoramidite chemistry may be used for this synthesis. The synthesis cycle may include the following four steps:
(1) Deprotection of the 5'-hydroxyl group (Detritylation),
(2) Coupling of nucleotide phosphoramidite to the 5'-hydroxyl group,
(3) Capping of unreacted 5'-hydroxyl groups
(4) Oxidation*

*Step (4) can be substituted with a sulfurization step for the synthesis of phosphorothioated oligonucleotides.

These four steps can be repeated in the above order until all nucleoside components are added.

The synthetic pathway may be as shown in scheme 1 below:

modification, conjugation, or attachment during synthesis and while the oligonucleotide is attached to a support.

In embodiments, the substituted heteroalkylene linker is modified, conjugated, or attached to substituents. A modification may include the conversion of the original substituent into a different substituent. For example, a bromo-alkane substituent may be converted into an azido-alkane. Conjugation may result in bonding of two large moieties together. For example, an NHS derivative may be conjugated with PEG-NH$_2$. A peptide may also be conjugated with an oligonucleotide or an antibody may be conjugated to an oligonucleotide. Attachment may result in bonding of the

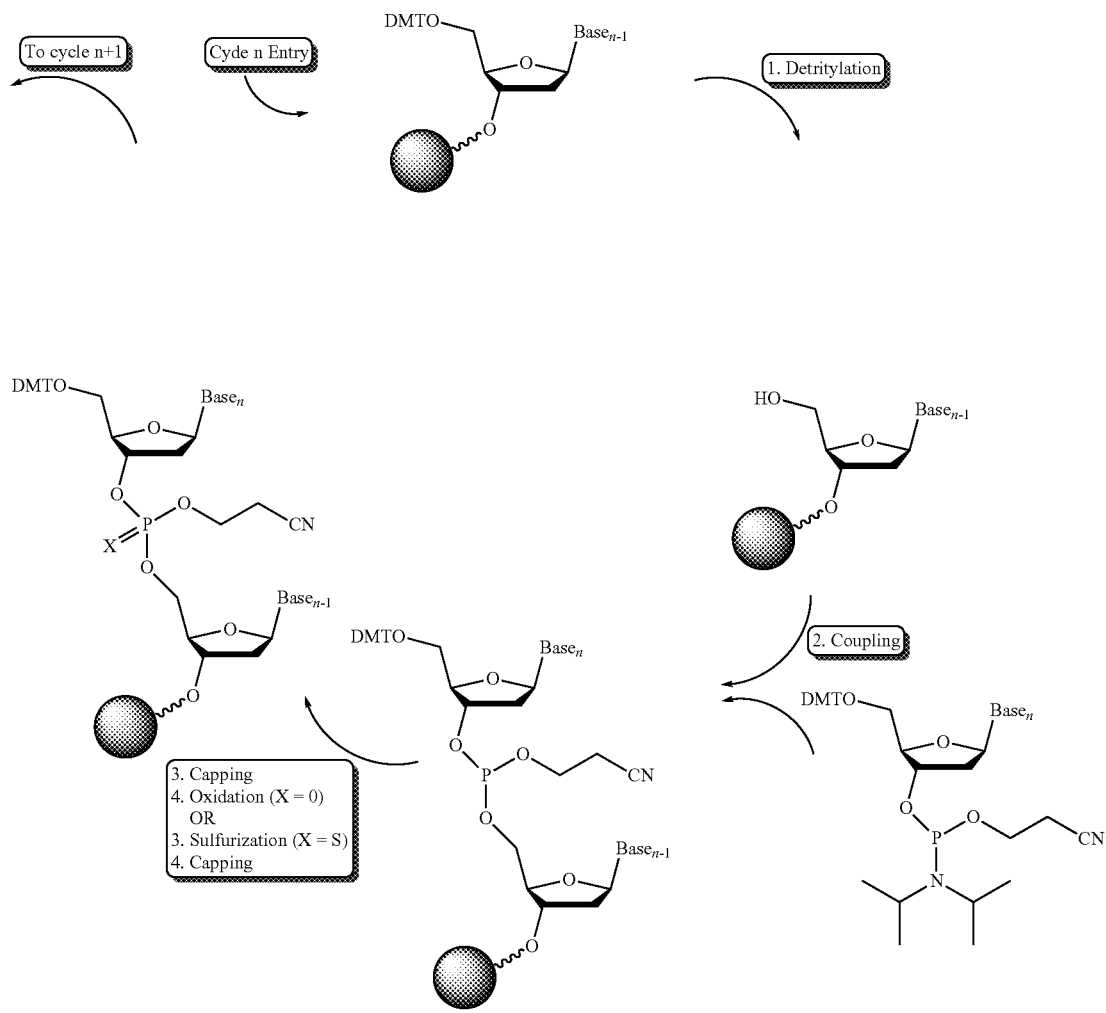

Scheme 1.

Additional details of the synthesis process is described in the Example 2 of this disclosure.

In embodiments, the heteroalkylene linker allow for further modification, conjugation, or attachment of additional moieties after completion of the synthesis and while the oligonucleotide is still attached to the support.

In embodiments, the present disclosure includes a CpG nucleic acid sequence conjugated to a saRNA with a substituted heteroalkylene linker, which may allow further small molecule to a large molecule. For example, NHS-ester of biotin might be attached to the amino derivative of an oligo.

In embodiments, the present disclosure includes a CpG nucleic acid sequence conjugated to a saRNA with linkers multiple different linkers, multiple identical linkers, or a substitution of linkers selected from the following groups: Fmoc amino-modifier C6 dT (introduction of the amino group) which can be further used for functionalization, by reacting with NHS ester and divinyl sulfone and its analogues.

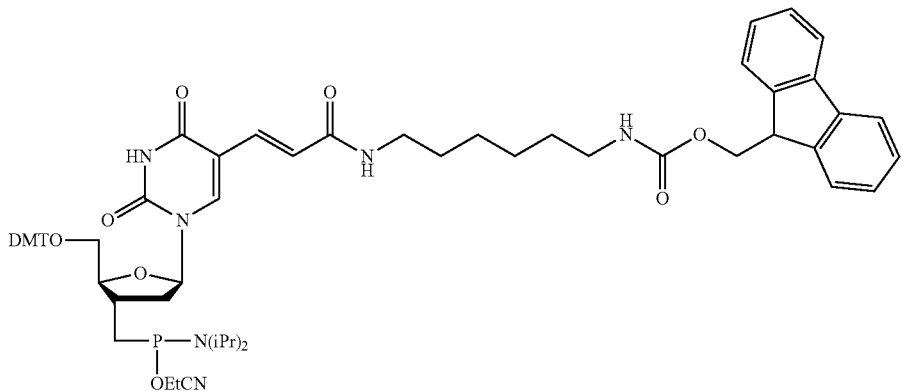
S-Bz-thiol-modifier C6-dT (introduction of sulfuhydryl group), which can be further used for functionalization by reacting with divinyl sulfone and acrylic analogues.
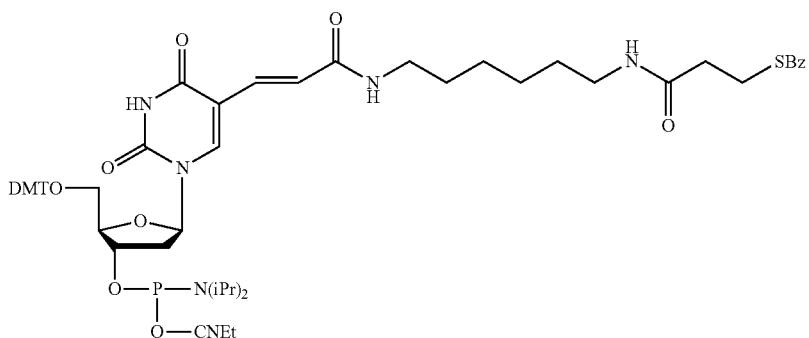
Amino-modifier Serinol Phosphoramidite (introduction of the amino group) which can be further be used for functionalization, by reacting with NHS ester and divinyl sulfone and its analogues.
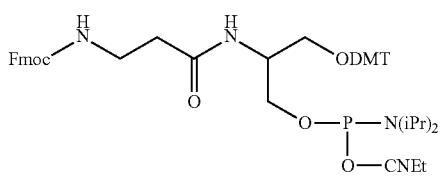

DBCO-dT (introduction of alkyne, copper free Click Chemistry) which can be further used for functionalization with azido-reactants Evaluation of CEBPα induction by quantitative real-time PCRs. $1 \times 10^5$ cells were plated in 500 µl media in a 24-well plate and transfected with indicated RNA oligos at final h unless indicated otherwise. For transfection of non-CpG conjugated oligos, 50 nM saRNA in Opti-MEM was incubated with Lipofectamine2000 (1:100 dilution) (Life Technologies, 11668-027) for 20 min at room temperature and 100 µl of lipid-saRNA complex was added. 72 h after transfection, total RNA from cells was purified with an

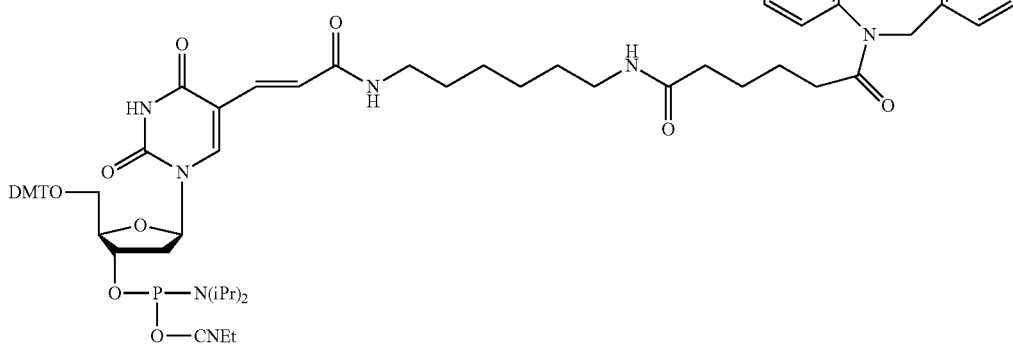

DBCO-sulfo-NHS Ester (introduction of the of alkyne, copper free Click Chemistry, by reacting with the amino groups)

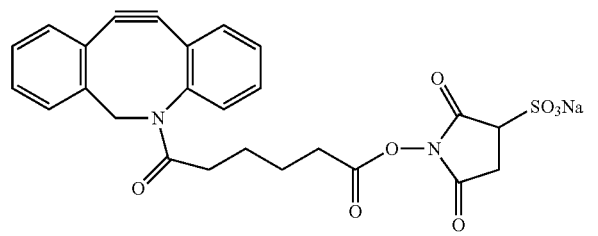

EXAMPLES

Example 1: Materials and Methods

CpG-CEBPα-saRNA Uptake.

$1 \times 10^5$ cells were incubated in 500 µl media with indicated saRNA (500 µM, final concentration). 3 h later, cells were washed with PBS twice. PBMCs were stained with anti-CD14 and anti-CD19 antibodies to assess uptake by different cell types. Cy3 uptake level was analyzed by flow cytometry.

CpG-saRNA(-Cy3) Localization in DU45.

$1 \times 10^5$ DU145 cells were plated on cover slips in a 24-well plate. When cells were ~60% confluent, Cy3-labeled CpG-saRNA conjugates were added to the culture at final concentration 500 µM. 2 h or 24 h post transfection, cells were gently washed with PBS with 1 mM $MgCl_2$ and 0.1 mM $CaCl_2$ twice and fixed with 0.25 ml 2% paraformaldehyde for 20 min at room temperature. Cells were then washed once with PBS with 1 mM $MgCl_2$ and 0.1 mM $CaCl_2$ and permeabilized within 0.1% Triton X-100 for 10 min at room temperature. Cells were then washed with PBS, stained using 500 ng/ml Hoechst33342 and mounted in 10 µl VECTASHIELD. Localization of CpG-saRNA was assessed by confocal microscopy. concentration of 500 µM every 24

RNeasy Minikit (Qiagen) according to the manufacturer's instructions. The iScript cDNA Synthesis kit (BioRad) was used for reverse transcription. A SsoAdvanced™ Universal Probes Supermix (Biorad) was used for Taqman quantitative real-time PCR and results were quantified with a CFX96 Real Time PCR Detection system (BioRad). mRNA expression level of CEBPA was normalized to TBP expression. The primer sequences used for human CEBPA were:

(forward primer) 5'-gacatcagcgcctacatcg-3'; (reverse primer) 5'-ggctgtgctggaacaggt-3'.

CEBP Reporter Assay.

CEBP reporter assay was performed according to the manufacturer's protocol (Qiagen CCS-001L). Briefly, $4 \times 10^4$ DU145 cells/well were seeded in 96-well plates at 150 µl volume of RPMI supplemented with 2.5% FCS only. 0.6 µl Lipofectamine2000, 1 µl Luciferase or control plasmid and non-CpG conjugated saRNA (final conc. 50 µM) in 50 µl OptiMem media (Life Technologies) were added. Luciferase- or control plasmid is only transfected once. CpG-conjugated saRNA were added in 50 µl RPMI media directly to wells at final concentration 500 µM every 24 h. Three days later, cells were gently washed with PBS and 50 µl of Passive Lysis Buffer (Promega E194A) was added directly into each well. The lysates were then transferred into white 96-well Optiplates (Perkin Elmer) for Renilla/Firefly Dual Luciferase assay with 50 µl of Luciferase Assay Reagent II (Promega E1910). The plate was then measured for firefly and then for Renilla luciferase. Values were normalized to the activity in the untreated sample. The experiment was performed in triplicates.

MV4;11 Maturation.

$1 \times 10^5$ MV4-11 cells were transfected with indicated saRNA (final concentration 500 µM) every 24 h except for SS/AS which was transfected using Lipofectamine2000 only once. 96 h later, cells were harvested, washed with FACS buffer (PBS with 2% FBS) twice and stained with antibodies specific to hCD86 (FITC), hCD40 (PE), HLADR (APC) and 7-AAD as a viability marker. Expression levels were measured by flow cytometry.

Development of Cbfb/MYH11/Mpl-Induced Mouse Leukemia Model.

Cbfb1/56M/Mx-Cre1 mice were backcrossed to wild-type C57BL/6 mice for >10 generations to generate the syngeneic AML model. Two weeks after polyinosinic-polycytidylic acid-induced (Invivogen) expression of core-binding factor β-smooth muscle myosin heavy chain, bone marrow cells from Cbfb1/56M/Mx-Cre1 mice were transduced with retroviral MIG-Mpl vector-encoding thrombopoietin receptor and GFP genes to generate transplantable Cbfb/MYH11/Mp11 mouse AML.

In Vivo Experiments.

C57BL/6 mice (6 to 8 weeks old) were from the National Cancer Institute (Frederick, Md.). Animal care/procedures were performed in accordance with established institutional guidance and approved protocols from the Institutional Animal Care and Use Committee (COH). $1 \times 10^6$ Cbfb/MYH11/Mp11 AML cells in phosphate-buffered saline were injected via retro-orbital injection.

For dose test, when AML cell levels in blood exceeded 1%, which corresponds to 10% to 20% of bone marrow-residing AML cells, various dose of CpG-CEBPA-saRNA or CpG-FLUC-RNA; 1, 2.5 or 5 mg/kg were administrated via retro-orbital injection and every other day and blood was drawn from the tail to monitor the circulating c-Kit$^+$/GFP$^+$ following injection (3-4 mice per group). The mice were euthanized 1 day after the 3rd treatment and % of c-Kit+/GFP$^+$ were analyzed in spleen and bone marrow by flow cytometry.

To test Anti-tumor efficiency of CpG-C/EBPa-saRNA, when % of GFP$^+$ AML reaches 1-5% in PBL, PBS (200 μl), CpG-FLUC RNA (5 mg/kg in 200 μl), or CpG-CEBPA saRNA (5 mg/kg in 200 μl) were injected 5 times every other day by retro orbital injection (6-8 mice/group). During the course of treatment, PBL was obtained by tail bleeding and analyzed by flow cytometry for AML burden every other day (GFP and 7AAD). The mice were euthanized 1 day after the 5th treatment and spleen and bone marrow were harvested for subsequent analysis.

CpG-STAT3 ASO Design and Synthesis.

The CpG-ASOs were synthesized in the DNA/RNA Synthesis Core (COH) by linking CpG(D19)-ODN to Stat3 or Scramble ASOs similarly as previously described (Kortylewski et al. *Nat. Biotech.* 2009).

Cells

Healthy PBMCs were derived from anonymous donors under IRB #13378 from the Donor Aphaeresis Center at CoH. Sample acquisition was approved by the CoH institutional review board in accordance with the Declaration of Helsinki. Human PC3 and DU-145 prostate cancer cells were purchased from American Type Culture Collection.

Flow Cytometry

For extracellular staining of cancer cell lines and immune cells, single cell suspension were incubated with FcγIII/IIR-specific antibody to block nonspecific binding and then stained with different combinations of fluorochrome-labeled antibodies to CD1c, CD3, CD19, CD303a, F4/80, GR1, B220 and CD11c (eBiosciences). Apoptotic cell death was determined by Annexin V assay. Fluorescence data were collected on a BD Accuri C6 Flow Cytometer (BD Biosciences) and analyzed using FlowJo software (Tree Star).

Biodistribution

C57BL/6 mice (6-8 weeks old) were purchased from the NCI (Frederick, Md.). C57BL/6 mice were injected intravenously with 5 mg/Kg with CpG-STAT3Cy3 and euthanized 3 h later. The lymph node and bone marrow were harvested. Single cell suspensions were prepared by mechanic tissue disruption and collagenase D/DNase I treatment as described (Kortylewski et al. *Nat. Med* 2005) and stained using CD1 b, CD3, B220, CD11c and F4/80 antibodies. The uptake by different population was accessed by flow cytometry.

Quantitative Real-Time PCR

Total RNA was extracted from cultured or in vivo grown tumor cells using Maxwell® system RNA purification kit (Promega) and then transcribed into cDNAs using iScript cDNA Synthesis kit (Bio-Rad). Gene expression was analyzed using Universal Probe Library (UPL, Roche) and specific pairs of primers designed using the ProbeFinder software (Roche) for STAT3 (Forward 5'-CTGCCTA-GATCGGCTAGAAAAC-3' and reverse 5'-CCCTTTG-TAGGAAACTTTTTGC-3') and TBP using Roche's Reference Gene Assays. Sequence-specific amplification was analyzed on the CFX96 Real-Time PCR Detection System (Bio-Rad). The data were normalized to the TBP levels and the relative gene expression levels were calculated using the $2^{-\Delta\Delta Ct}$ method.

Confocal Microscopy

DU-145 cells were treated using 500 nM CpG-STAT3 ASO Cy3 labeled for different time points. Cells were fixed with 2% paraformadehyde for 20 min, permeabilized in PBS containing 0.1% Triton X-100 and the nuclei were stained using DRAQ5® 5 min. Slides were mounted in mounting medium (Vector Labs, Burlingame, Calif.). Confocal imaging was carried out using C-Apochromat 40x/1.2 water-immersed objectives on cLSM510-Meta inverted confocal microscope (Zeiss, Thornwood, N.Y.). LSM software v.4.2 SP1 was used for image acquisition, and LSM Image Browser v.4,2,0,121 for post-acquisition analysis (Zeiss).

Statistics

Unpaired t test was used to calculate two-tailed P value to estimate statistical significance of differences between two treatment groups. One- or two-way ANOVA plus Bonfeerroni post-test were applied to assess differences between multiple groups or in tumor growth kinetics experiments, respectively. Statistically significant P values were indicated in figures as follows: \*\*\*, P<0.001; \*\*, P<0.01 and \*, P<0.05. Data were analyzed using Prism software v. 6.01 (GraphPad).

Example 2: Manufacturing Process of the CpG-saRNA Synthesis

CpG-CEBPA saRNA (SS, sense strand) and CEBPA saRNA (AS, antisense strand) were synthesized using a cycle consisting of four steps as described in the following sections. After the complete synthesis, deprotection, purification and desalting of CpG-CEBPA saRNA (SS) and CEBPA saRNA (AS), the two components were annealed to produce the drug product CpG-CEBPA saRNA (SS/AS).

The starting point of the synthesis was a protected nucleoside linked via its 3'-oxygen to a polystyrene-based solid support. Nucleoside phosphoramidite chemistry was used for this synthesis. The synthesis cycle consisted of the following four steps:

(1) Deprotection of the 5'-hydroxyl group (Detritylation),
(2) Coupling of nucleotide phosphoramidite to the 5'-hydroxyl group,
(3) Capping of unreacted 5'-hydroxyl groups
(4) Oxidation\*

\*Step (4) can be substituted with a sulfurization step for the synthesis of phosphorothioated oligonucleotides.

These four steps were repeated in the above order until all nucleoside components were added.

The synthetic pathway is shown in scheme 1 of this disclosure (see above):

The first stages of the manufacturing (up to deprotection and HPLC purification), were performed using an OligoPilot100 and AktaPurifier from GE, 800 Centennial Avenue, Piscataway, N.J. 08855-1327.

Detritylation

In the first step of the synthesis cycle, the acid labile dimethoxytrityl (DMT) group of the support-bound monomer was removed with a 5% solution of dichloroacetic acid (DCA) in toluene. The resulting DMT cation chromophore was quantitated to determine coupling efficiency of the synthetic cycle. An orange color was produced by the cleaved DMT carbocation, which absorbed in the visible region at 495 nm. The intensity of this absorbance was used to determine the coupling efficiency. Most commercially available DNA synthesizers have hardware to measure and record the detritylation yield for each cycle so that the efficiency of synthesis can be monitored in real time. As the DNA bases are acid-labile, the detritylation step must only be as long as is necessary to ensure complete detritylation.

Synthesis of CpG-CEBPA saRNA (SS) and began with the first 3'-end nucleoside, 2'-O-methyl Uridine, already attached to the solid support. The solid support used for the synthesis was LCAA-CPG Support from Prime Synthesis. The first nucleoside as attached to the support through a three carbon linker and a succinate linkage. Synthesis at the scale of 0.75 mmol required 19.00 g of support placed in a 92 mL sized column. The product from this reaction should have a mass gain of 13 g.

The solid support used for the synthesis of CEBPA saRNA (AS) was LCAA-CPG from Prime Synthesis. Synthesis of CEBPA saRNA (AS) at the scale of 0.75 mmole required 9.5 g of support placed in a 46 mL sized column. The product from this reaction should have a mass gain of 11 g.

Coupling

After detritylation the next protected phosphoramidite was delivered to the reaction column. Ethylthiotetrazole was used to activate the phosphoramidite. The two reagents were mixed just prior to delivery to the reaction column. Ethylthiotetrazole, a weak acid, protonated the tertiary nitrogen group of the phosphoramidite and the diisopropylamine moiety became a good leaving group.

The Coupling Mechanism was a nucleophilic attack by the free 5'-hydroxyl group on the 3'-O-phosphorus of the incoming activated monomer. For this reason, a totally hydroxyl-free environment in the column was important to have. To ensure this, dry acetonitrile was used as the general solvent, and all the reagents and solvents were maintained in the anhydrous state. Under these conditions the coupling efficiencies were very high, thereby permitting synthesis of long oligonucleotides.

Coupling Conditions

Phosphoramidites dissolved in anhydrous acetonitrile, ACN (0.175 M), activator ethylthiotetrazole, ETT (0.6M M in anhydrous ACN). 2.5 Equivalents (eq) of deoxy phoshoramidites, 2.5 eq of propanediol linker phosphoramidite and 3.0 eq of ribo phosphoramidites were used. Recycling time for DNA and Propanediol was 3.5 min, for RNA 12.50 min and for ribo guanosine 12.00 min. The activator:phosphoramidite v/v ratio is 3:2. Coupling was performed at room temperature (22-24° C.).

Capping

In spite of these efficiency measures, a small percentage of the support-bound nucleoside's 5' hydroxyls did not couple to the incoming activated monomer. They were rendered inactive to minimize deletion products and simplify the purification process. Usually, acetic anhydride and 1-methyl-imidazole dissolved in pyridine and tetrahydrofuran (THF) or ACN act to create an acylating agent that "caps" the unextended 5'-hydroxyls. The 5'-acetyl ester cap as unreactive in all subsequent cycles and was removed during the final ammonia deprotection step. Additional ACN washing subsequent to capping increased synthetic yield.

Capping Conditions

CAP A was a 20% solution of 1-methyl-imidazole in anhydrous ACN, CAP B was generated by mixing equal volumes of CAP B1 and CAP B2 prior to use, where CAP B1 as a 40% solution acetic anhydride in anhydrous ACN, and CAP B2 was a 60% solution of 2,6-lutidine in anhydrous ACN.

Oxidation

After coupling and capping, the internucleotide linkage was a trivalent phosphite triester that was unstable and must be oxidized to a phosphotriester. This step can be substituted with a sulfurization step for the synthesis of phosphorothioate oligonucleotides.

Oxidation Conditions

Oxidation was conducted with 0.05 M solution of iodine in pyridine:water, 9:1. Oxidative sulfurization was conducted in a 0.3 M solution of xanthane hydride in anhydrous pyridine.

Final Detritylation

Final detritylation is conducted on the synthesizer by wash with a solution of 5% DCA in toluene.

Removal from Support and Deprotection

After the specified sequence has been assembled, the oligonucleotide must be removed (cleaved) from the support and fully deprotected prior to use. Following the synthesis; the resin was treated with a solution of 20% diethylamine (DEA) in ACN to deprotect the phosphorus by β-elimination of the cyanoethyl group. A 60 minute, 55° C. treatment with 600 mL of methylamine-ammonium hydroxide mixture (AMA) was used to cleave the oligonucleotide from the support and to remove the protecting groups of the exocyclic amino groups. The resulted mixture was rapidly cooled in ice, filtered, and the polymer residue was washed two times with 200 mL of ethanol:water, 1:1. Resulted solutions were combined, placed in the volumetric flask and representative samples were taken to estimate the yield by measuring the absorbance at 258 nm. The solution is then quickly evaporated to dryness under the reduced pressure and weighed.

After this cleavage and deprotection with AMA, the resulting crude mixture contained the full length oligonucleotide, still carrying the 2'-TBDMS protection on ribose residues, the truncated failure sequences with free 5'-hydroxyl ends and biproducts of deprotection (benzamide, isobutyramide, acrylonitrile, and acetamide). The TBDMS protecting groups were removed at the final deprotection step by the basic fluoride ion. Deprotection was conducted by treatment with 700 mL of a mixture of triethylamine trihydrofluoride/triethylamine/DMSO, 10:2:1, at 60° C. for 1.5 hrs. The reaction was then cooled to ambient temperature, mixed with 3 L of acetone, left at ambient temperature overnight, and centrifuged. The supernatant was separated, representative samples of supernatant were taken (5×20 µL), evaporated to dryness under the reduced pressure, re-dissolved, and the absorption was measured at 258 nm. If a significant amount of products are still present in the supernatant, another 1,000 mL of acetone was added and the mixture was kept at room temperature for an additional 2 hours. After the final centrifugation the supernatant was discarded and pellets were kept under vacuum at room temperature until dry.

RNA Synthesis

RNA chemical synthesis was identical to that used for DNA, with the exception for the need of an additional protecting group at the 2'-hydroxyl of ribose. This position is usually protected with tert-butyldimethyl silyl groups, which are stable throughout the synthesis. They were removed at the final deprotection step by the basic fluoride ion. The remaining positions on both the sugar and the bases were protected in the same fashion as for DNA. By adjusting several parameters in the DNA synthesis protocol—including the coupling times, monomer delivery rate, frequency of washing steps—stepwise coupling efficiencies of up to 99% were be obtained.

Annealing

Many methods can be used to anneal complementary strands of nucleic acids. In each case, the goal is to denature the complementary strands to remove any secondary structure and then allow the strands to hybridize. Two factors that influence the efficiency of oligonucleotide hybridization are salt concentration and the rate of temperature decrease. Annealing occurs most efficiently when the temperature is slowly decreased after denaturation, especially when the oligonucleotides have high GC content or form hairpin structures. Annealing complementary strands of nucleic acid comprised the following four steps:

1. Mixed concentrated complementary oligonucleotides together at a 1:1 molar ratio in a pear shaped round bottomed 1,000 mL flask.
2. Diluted oligonucleotide mixture to a final concentration in water
3. Annealed oligonucleotides using a water bath.
    Incubated the 1,000 mL round bottomed flask of oligonucleotides in the 85° C. water for 3.0 minutes.
    Transferred the flask into the 37° C. water bath, incubate for 30 min.
4. Poured into the appropriate trays. Place trays inside the Lyophilizer. Froze the trays and followed with lyophilization.

Process Controls

Identity of reagents was verified prior to use and synthesis parameters were verified prior to initiation of the synthesis. Coupling efficiency was monitored by a DMT cation assay of effluent obtained after the deblocking step. The DMT group was the hydroxyl protecting group at the 5' terminus of the oligonucleotide. The DMT assay was useful for immediate feedback on the performance of an automated DNA synthesizer. The DMT cation was liberated at each detritylation step in the synthesis cycle and as quantitated by UV absorbance measurement. Other parameters of the synthesis such as pressure, conductivity, temperature, flow of the reagents, contact time of the reagents with the support were also monitored in real time. Results of monitoring were included in the Synthesis Evaluation file created and stored by Unicorn software on the OligoPilot 100.

Example 3: Targeted CpG-STAT3ASO as an Inhibitor of Tumorigenic and Immunosuppressive Signaling for Metastatic Prostate Cancer Immunotherapy Cancer Immunotherapy Targeting STAT3

The STAT3 transcription factor is a multifaceted oncogene and a master regulator of immunosupression commonly activated in human cancers. Extensive evidence suggest that tumors, such as advanced prostate cancers, critically depend on STAT3 for their survival, vascularization and metastasis, whereas normal cells do not (Mora, L. B. et al. *Cancer Res* 62, 6659-66 (2002), Dhir, R. et al. *Prostate* 51, 241-6 (2002), Lee, S. O. et al. *Prostate* 60, 303-9 (2004), and Hedvat, M. et al. *Cancer Cell* 16, 487-97 (2009)). In prostate cancers, STAT3 activation results in tumor progression towards hormone-refractory/castration-resistant prostate cancer (CRPC) phenotype and poor patients' survival. STAT3 activity is often triggered by cytokines released in response to stress and inflammation, downstream from Toll-like receptor (TLR) and NF-κB signaling.

TLR9/NF-κB/STAT3 signaling axis plays a role in the prostate cancer cell self-renewal, tumorigenic potential and therapeutic resistance. As a unique a point of convergence for inflammatory and tumorigenic signaling, STAT3 is activated in both malignant cells and tumor-associated immune cells such as myeloid-derived suppressor cells (MDSCs). The MDSCs are heterogeneous population of immature and potently immunosuppressive myeloid cells which play pivotal role in prostate cancer progression and poor patients' survival.

A population of TLR9+ granulocytic MDSCs (G-MDSCs; Lin-HLA-DR-CD14-CD15HICD33LO) have highly activated STAT3 which accumulates in blood of prostate cancer patients during progression of the disease from localized to metastatic/castration-resistant prostate cancer (mCRPC). The inhibitory effects of these G-MDSCs on T cell proliferation rely on the STAT3-mediated expression of Arginase-1 (ARG-1), thereby potently inhibiting T-cell proliferation and activity.

Rapid Internalization of CpG ODN Conjugates in Immune and Prostate Cancer Cells

Figure 9B:
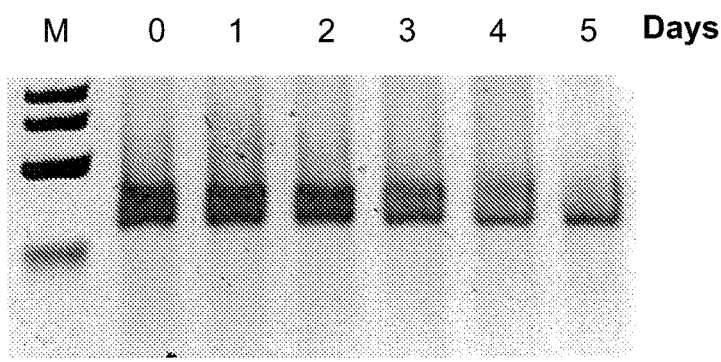
Figure 9C:
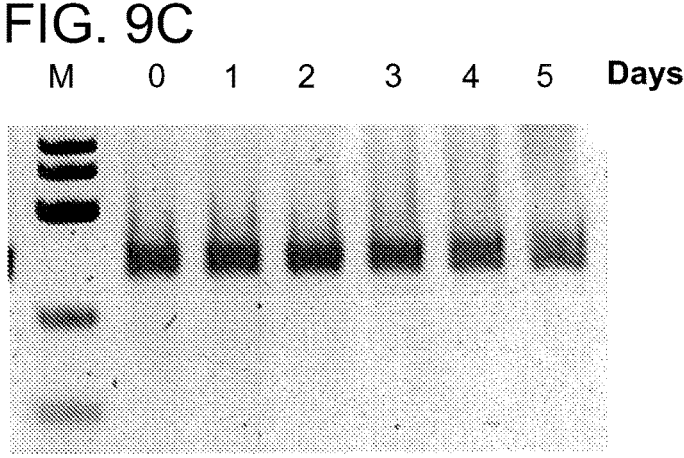
Figure 10A:
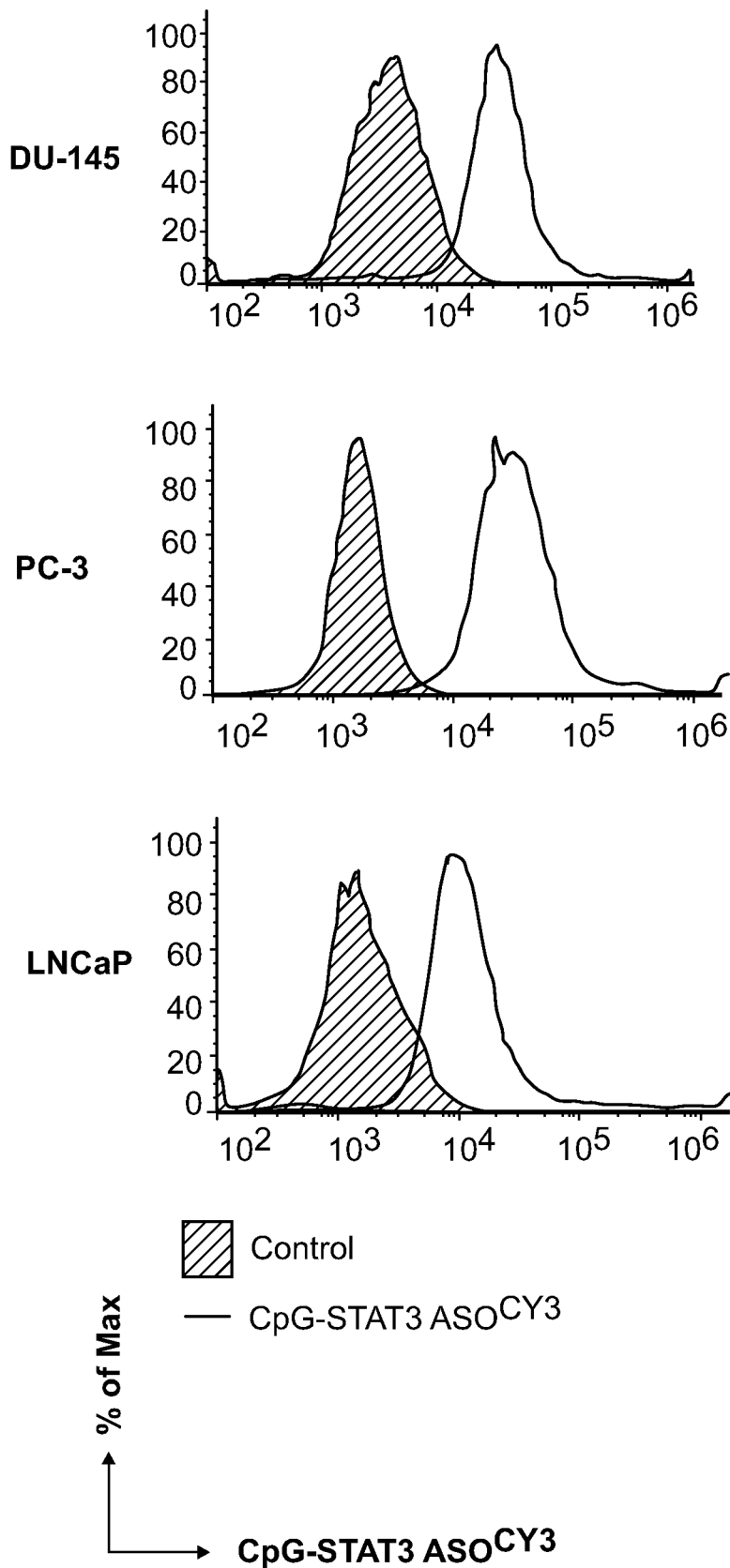
FIGS. 10A-10B show flow cytometry data of CpG-STAT3 ASO$^{Cy3}$ by human immune and prostate cancer cells in vitro. Human prostate cancer cells (FIG. 10A) and splenocytes (FIG. 10B) were incubated with the indicated concentrations of fluorescently-labeled CpG-STAT3 ASO$^{Cy3}$ for one hour without any transfection reagents. The oligonucleotide uptake by cancer cells, dendritic cells (DCs; CD11c), macrophages (MAC; F4/80+Gr1−), B cells (B220+CD11c−) and T cells (CD3+) was assessed using flow cytometry. CpG-STAT3 ASO$^{Cy3}$ was rapidly internalized by mouse immune and prostate cancer cells in vitro.
Figure 10B:
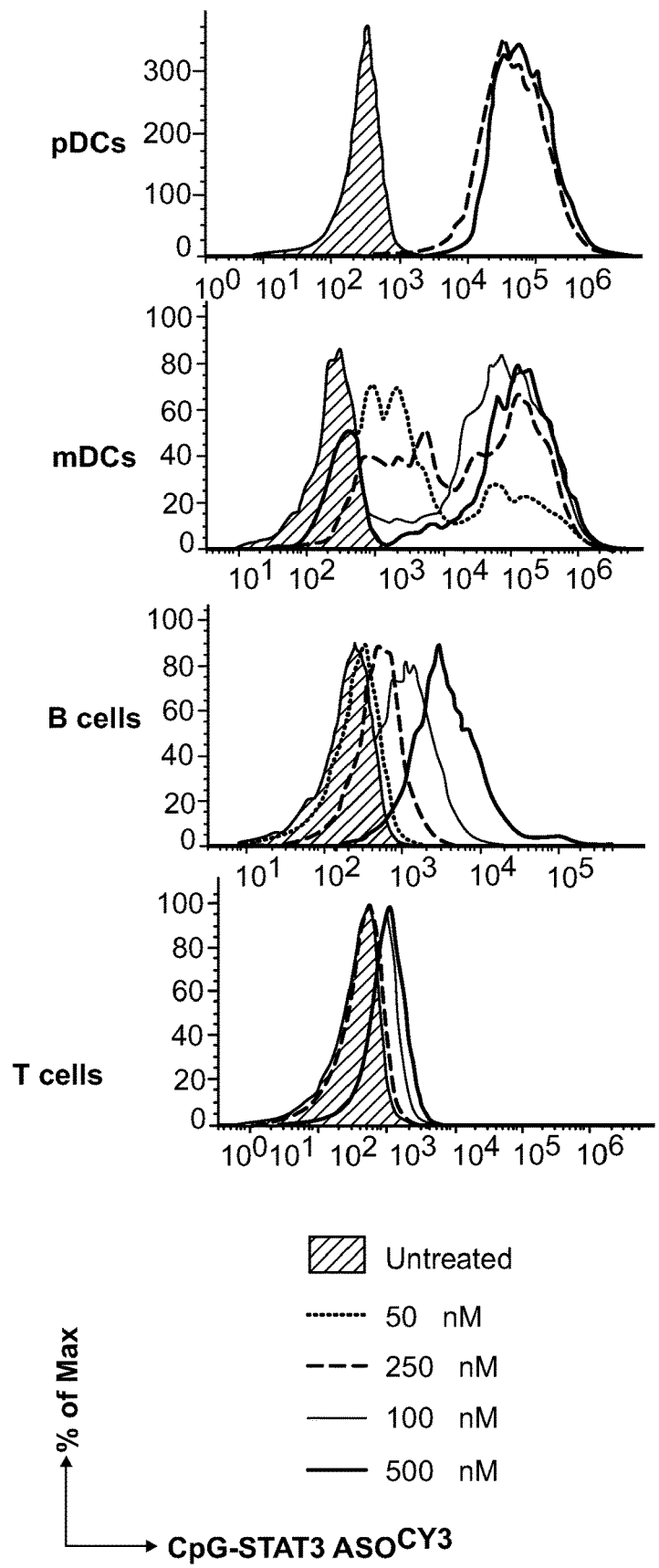
Figure 11A:
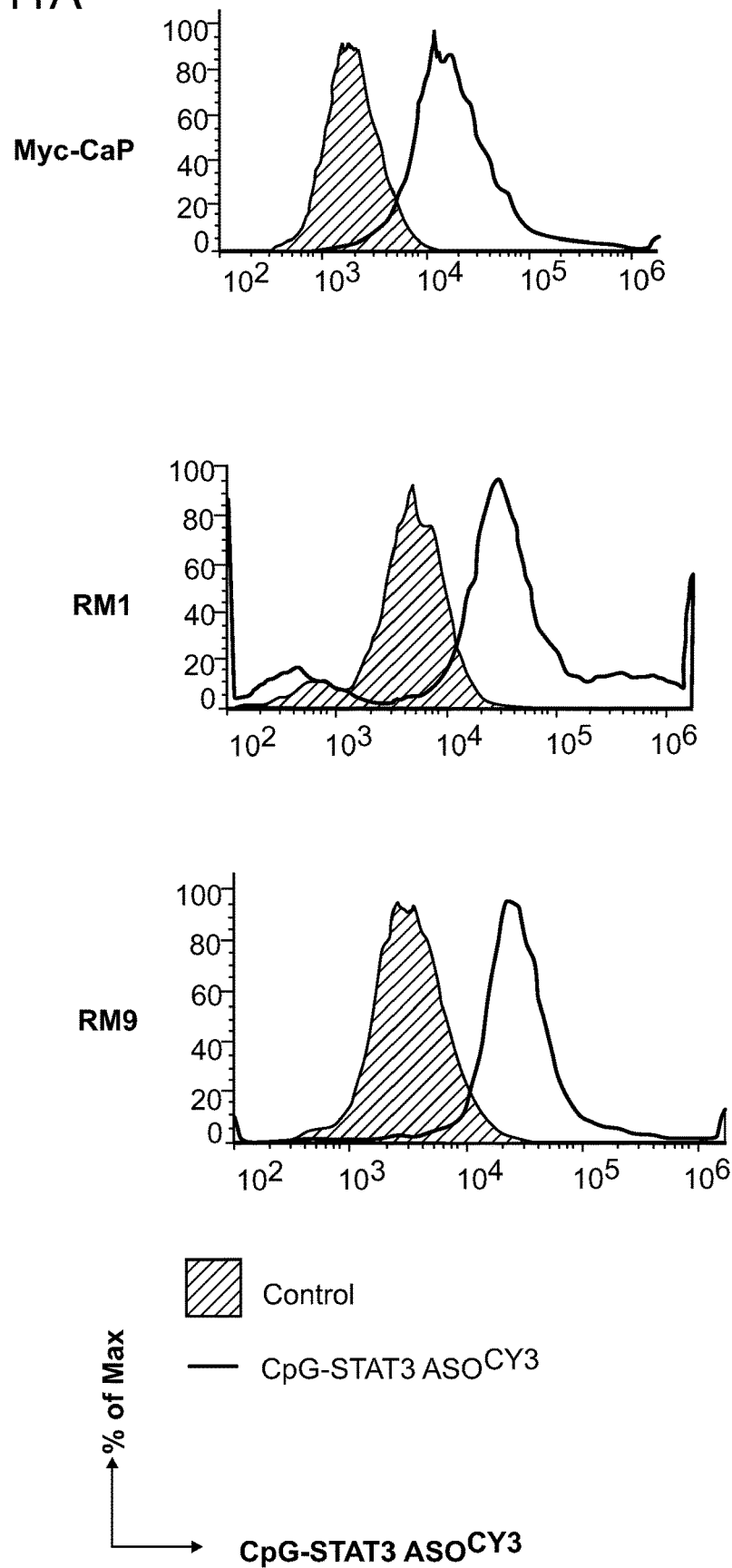
FIGS. 11A-11B show flow cytometry data of CpG-STAT3 ASO$^{Cy3}$ by mouse immune and prostate cancer cells in vitro. Mouse prostate cancer cells (FIG. 11A) and splenocytes (FIG. 11B) were incubated with the indicated concentrations of fluorescently-labeled CpG-STAT3 ASO$^{Cy3}$ for one hour without any transfection reagents. The oligonucleotide uptake by cancer cells, dendritic cells (DCs; CD11c), macrophages (MAC; F4/80+Gr1−), B cells (B220+CD11c−) and T cells (CD3+) was assessed using flow cytometry. CpG-STAT3 ASO$^{Cy3}$ was rapidly internalized by mouse immune and prostate cancer cells in vitro.
Figure 11B:
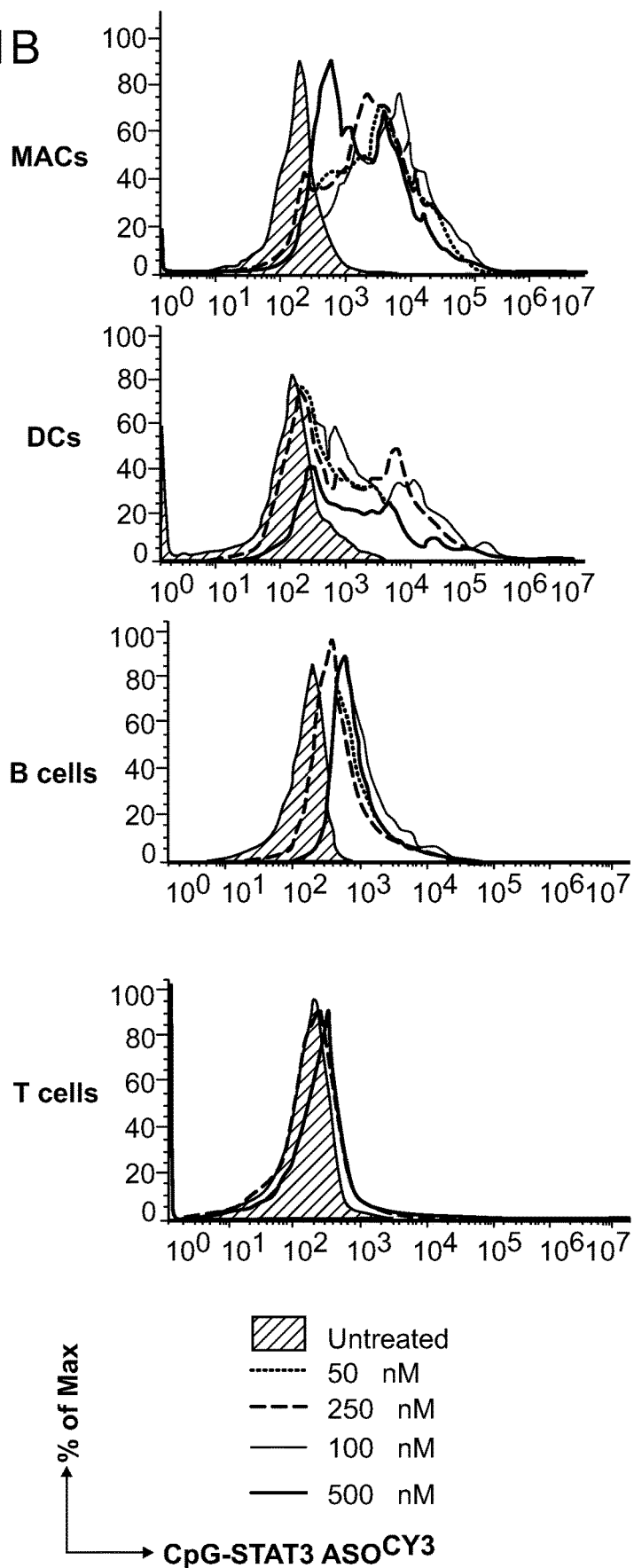

Conjugates of CpG oligodeoxynucleotide (ODN) were generated, a synthetic TLR9 ligand, with various chemically-modified and nuclease-resistant STAT3 ASO sequences (Tables 1-4, and FIGS. 9A-9C). Linking of the CpG ODN to STAT3 ASO allowed for quick internalization by target TLR9+ cells such as human and mouse immune cells as well as prostate cancer cells within one hour of incubation (FIGS. 10A-10B (human), and FIGS. 11A-11B (mouse), respectively). The uptake of CpG-STAT3 ASO by myeloid immune cells was detectable even at the lowest 50 nM concentration (FIGS. 10A-10B, and FIGS. 11A-11B).

Efficient Uptake of CpG-STAT3 ASO

The intracellular uptake of CpG-STAT3 ASO was verified using confocal microscopy. As shown in FIGS. 12A-12D, the conjugate was detectable in the cytoplasm of target cells within 15 min after adding it to culture media. The efficient uptake of these conjugates corresponded to improved efficacy of STAT3 knockdown in DU145 and LNCaP-S17 cells within 24 h of incubation often exceeding the effect of the respective ASO alone (FIGS. 13A-13D). The conjugate of ASO to GpC ODN which does not activate TLR9 (GpC-STAT3 ASO) also strongly inhibited STAT3 expression (FIGS. 13A-13D). Importantly, only CpG-STAT3 ASO conjugate but neither STAT3 ASO alone nor control CpG-scrambled ODN was able to induce cell death in DU145 and LNCaP-S17 cells within 24 h of culture in the presence of 500 nM of oligonucleotides (FIGS. 14A-14B).

Nuclease-Resistance of CpG-ASO Allowed for Systemic Administration and Targeting of TLR9+ Cells in Distant Organs Improved nuclease-resistance of CpG-ASOs, allowed for systemic administration and targeting of TLR9+ cells in distant organs, such as spleen or bone marrow (FIGS.

15A-15B). A single intravenous (IV) injection of fluorescently-labeled CpG-STAT3ASO delivered the conjugate to the majority of myeloid cells in the bone marrow and significant proportion of myeloid cells, including DCs, in peripheral lymph nodes (FIGS. 15A-15B). The experiments on human B cell lymphoma cells suggest that CpG-STAT3ASO strategy can be utilized against other TLR9+ malignancies, enhancing target gene knock down and cytotoxicity (FIGS. 16A-16C). Overall, these results indicate that new nuclease-resistant CpG-STAT3 ASO inhibitors allow for simultaneous targeting of STAT3 signaling in disseminated TLR9+ prostate cancer cells and in tolerogenic tumor-associated immune cells, such as MDSCs. Should such two-pronged strategy be effective in vivo, provides a paradigm-shifting immunotherapeutic approach to targeted cancer therapy focused on the disruption of signaling cross talk within the tumor microenvironment.

Example 4

CpG-STAT3 ASO Design and Synthesis

The CpG-ASOs were synthesized in the DNA/RNA Synthesis Core (COH) by linking CpG(D19)-ODN to Stat3 or Scramble ASOs similarly as previously described (Kortylewski et al. Nat. Biotech. 2009).

Healthy PBMCs were derived from anonymous donors under IRB #13378 from the Donor Aphaeresis Center at CoH. Sample acquisition was approved by the institutional review board in accordance with the Declaration of Helsinki. Human PC3 and DU-145 prostate cancer cells were purchased from American Type Culture Collection, while the LnCaP S17 stably expressing IL-6 were from Vaccine and Gene Institute, FL. Mouse Myc-CaP cells, RM1 and RM9 were obtained from respective original sources. Human LNCaP, DU145, PC3 prostate cancer cells were originally derived from ATCC and authenticated. Human OCI-Ly3, RL, Jecko1 and REC1 B cell non-Hodgkin lymphoma cells were obtained from City of Hope.

Flow Cytometry

For extracellular staining of cancer cell lines and immune cells, single cell suspension were incubated with FcγIII/IIR-specific antibody to block nonspecific binding and then stained with different combinations of fluorochrome-labeled antibodies to CD1c, CD3, CD19, CD303a, F4/80, GR1, B220 and CD11c (eBiosciences). Apoptotic cell death was determined by Annexin V assay. Fluorescence data were collected on a BD Accuri C6 Flow Cytometer (BD Biosciences) and analyzed using FlowJo software (Tree Star).

Total cellular lysates were prepared as previously reported[31] and analyzed using antibodies specific to tyrosine-phosphorylated STAT3 (Cell Signaling), total STAT3 (Santa Cruz) and β-actin (Sigma).

In Vivo Experiments

C57BL/6 mice (6-8 weeks old) were purchased from the NCI (Frederick, Md.). Animal care/procedures were performed in accordance with established institutional guidance and approved protocols from the IACUC (COH). Mice were injected subcutaneously in two sites with 2×10⁵ RM9 cells. The tumor growth was assessed using a caliper. Mice with established tumors were treated using intratumoral injection with various CpG-conjugates (5 mg/kg) every day and euthanized a day after the last treatment. For the experimental metastatic mouse model, C57BL/6 mice were injected intratibially with 2×10⁵ RM9 mcherry/luciferase cells in PBS. Mice with established tumors were injected intravenously with CpG-conjugates (5 mg/kg) every day and euthanized based on the body score following the institution guide line or day after the last treatment. Tumor burden was monitored using the bioluminescent imaging (BLI) was measured using AmiX (Spectral) imaging system.

Biodistribution

C57BL/6 mice (6-8 weeks old) were purchased from the NCI (Frederick, Md.). Animal care/procedures were performed in accordance with established institutional guidance and approved protocols from the IACUC (COH). C57BL/6 mice with or without established tumors were injected intravenously with 5 mg/kg with CpG-STAT3$^{Cy3}$ and euthanized 3 h later. The tumor, lymph node bone marrow, spleen and brain were harvested. Single cell suspensions were prepared by mechanic tissue disruption and collagenase D/DNase I treatment as described (Kortylewski et al. Nat. Med 2005) and stained using CD11b, CD3, B220, CD19, CD56, CD11c and F4/80 antibodies. The uptake by different population was accessed by flow cytometry.

Quantitative Real-Time PCR

Total RNA was extracted from cultured or in vivo grown tumor cells using Maxwell® system RNA purification kit (Promega) and then transcribed into cDNAs using iScript cDNA Synthesis kit (Bio-Rad). Gene expression was analyzed using Universal Probe Library (UPL, Roche) and specific pairs of primers designed using the ProbeFinder software (Roche) for STAT3 (Forward 5'-CTGCCTA-GATCGGCTAGAAAAC-3' [SEQ ID NO:96], and reverse 5'-CCCTTTGTAGGAAACTTTTTGC-3' [SEQ ID NO:97]) and TBP using Roche's Reference Gene Assays. Sequence-specific amplification was analyzed on the CFX96 Real-Time PCR Detection System (Bio-Rad). The data were normalized to the TBP levels and the relative gene expression levels were calculated using the $2^{-\Delta\Delta Ct}$ method.

Confocal Microscopy

DU-145 cells were treated using 500 nM CpG-STAT3 ASO Cy3 labeled for different time points. Cells were fixed with 2% paraformadehyde for 20 min, permeabilized in PBS containing 0.1% Triton X-100 and the nuclei were stained using DRAQ5® 5 min. Slides were mounted in mounting medium (Vector Labs, Burlingame, Calif.). Confocal imaging was carried out using C-Apochromat 40×/1.2 water-immersed objectives on cLSM510-Meta inverted confocal microscope (Zeiss, Thornwood, N.Y.). LSM software v.4.2 SP1 was used for image acquisition, and LSM Image Browser v.4,2,0,121 was used for post-acquisition analysis (Zeiss).

Unpaired t test was used to calculate two-tailed P value to estimate statistical significance of differences between two treatment groups. One- or two-way ANOVA plus Bonfeerroni post-test were applied to assess differences between multiple groups or in tumor growth kinetics experiments, respectively. Statistically significant P values were indicated in figures as follows: *, P<0.001; , P<0.01 and *, P<0.05. Data were analyzed using Prism software v. 6.01 (GraphPad).

Conjugates of CpG oligodeoxynucleotide (ODN), a synthetic TLR9 ligand, with various chemically-modified and nuclease-resistant STAT3 ASO sequences were generated (Tables 1, 2, and 4; and FIG. 9A). Linking of the CpG ODN to STAT3 ASO allowed for quick internalization by target TLR9⁺ cells such as human and mouse immune cells as well as prostate cancer cells within one hour of incubation (FIGS. 10A-10B and FIGS. 11A-11B). The uptake of CpG-STAT3 ASO by human and mouse myeloid immune cells was detectable even at the lowest 50 nM concentration (FIGS. 10A-10B and FIGS. 11A-11B). The intracellular uptake of CpG-STAT3 ASO was verified using confocal microscopy. As shown in FIGS. 12A-12D, the conjugate was detectable in the cytoplasm of target cells within 15 min after adding it to culture media. The efficient uptake of these conjugates corresponded to improved efficacy of STAT3 knockdown in DU145 and LNCaP-S17 cells within 24 h of incubation often exceeding the effect of the respective ASO alone (FIGS. 13A-13B). The conjugate of ASO to GpC ODN which does not activate TLR9 (GpC-STAT3 ASO) also strongly inhibited STAT3 expression (FIGS. 13A-13B). The CpG-STAT3ASO showed more rapid induction of STAT3 knock-down at both mRNA (FIG. 13C) and protein (FIG. 13D) levels compared to the unconjugated STAT3ASO. That CpG-STAT3ASO internalization and target knock-down is similarly effective also in glioma and microglia cells were also verified (FIGS. 17A-17C). Importantly, only CpG-STAT3 ASO conjugate, but not STAT3 ASO alone or control CpG-scrambled ODN, was able to induce cell death in DU145 and LNCaP-S17 cells within 24 h of culture in the presence of 500 nM of oligonucleotides (FIGS. 14A-14B).

Improved nuclease-resistance of CpG-ASOs, allows for systemic administration and targeting of TLR9$^+$ cells in distant organs, such as spleen or bone marrow (FIGS. 15A-15C, and FIGS. 18A-18C). A single intravenous (IV) injection of fluorescently-labeled CpG-STAT3ASO was sufficient to deliver the conjugate to the majority of myeloid cells in the bone marrow and significant proportion of myeloid cells, including DCs, in peripheral lymph nodes (FIGS. 15A-15C). Repeated IV injections allowed for CpG-STAT3ASO penetration of significant fraction of myeloid cells (e.g. 30% of MDSCs) in brain localized glioma tumors, while almost complete penetration of the tumor microenvironment was achieved after single local injection of this oligonucleotide (FIGS. 18A-18C). Experiments on human B cell lymphoma cells suggest that CpG-STAT3ASO strategy can be utilized against other TLR9$^+$ malignancies, enhancing target gene knock down and cytotoxicity (FIGS. 16A-16C). To test in vivo efficacy of CpG-STAT3ASO, we selected a model of aggressive syngeneic prostate cancer, Ras-/Myc-driven and hormone-independent RM9 tumors. In initial experiments, mice were engrafted subcutaneously with RM9 tumors in two locations and tumors in one site were treated using intratumoral injections of CpG-STAT3ASO, STAT3ASO or control oligonucleotides (FIGS. 19A-19D). Although both CpG-STAT3ASO and STAT3ASO initially inhibited growth of tumors in the treated site, only CpG-STAT3ASO also reduced tumor size in the distant untreated locations (FIG. 19A). These effects correlated with reduction of STAT3 expression in the distant site likely indicating systemic effect of CpG-STAT3ASO release from the injections site (FIG. 19B and FIG. 19E). In addition, treatment using CpG-STAT3ASO and not STAT3ASO reduced expression of STAT3 and PD-L1 immune checkpoint molecules in myeloid-derived suppressor cells (MDSCs) at the distant tumor site (FIGS. 19C-19D). To verify antitumor effect of CpG-STAT3ASO administered systemically, experimental model of bone metastatic prostate tumors was implanted intratibially (FIGS. 20A-20B). After tumors were established mice were treated using daily intravenous injections of 5 mg/kg of CpG-STAT3ASO, STAT3ASO, control CpG-scrODN or only PBS. As shown in FIGS. 20A-20B, only CpG-STAT3ASO treatment induced complete regression of bone-localized RM9 tumors compare to limited effect of STAT3ASO and control CpG-scrODN. Thus, new nuclease-resistant CpG-STAT3 ASO inhibitors allow for simultaneous targeting of STAT3 signaling in disseminated TLR9$^+$ prostate cancer cells and in tolerogenic tumor-associated immune cells, such as macrophages/microglia/MDSCs (FIG. 21). The results demonstrate that immunotherapeutic approach to targeted cancer therapy focused on the disruption of signaling cross talk within the tumor microenvironment can be effective in treating cancer.

Numbered embodiments of the present disclosure are:

An isolated compound comprising a phosphorothioated oligodeoxynucleotide (ODN) sequence conjugated to a short-activating RNA (saRNA) or an antisense oligonucleotide (ASO) sequence.

The compound, wherein said short-activating RNA (saRNA) is a saRNA of CCAAT/enhancer-binding protein-α (C/EBPα).

The compound, wherein said ASO is an ASO of Signal Transducer and Activator of Transcription (STAT).

The compound, wherein said antisense sequence is an anti-STAT1, anti-STAT2, anti-STAT3, anti-STAT4, anti-STAT5A, anti-STAT5B, or anti-STAT6 oligonucleotide sequence.

The compound, further comprising a linker between the ODN sequence and the short-activating RNA (saRNA) or the ASO.

The compound, wherein the linker comprises a substituted or unsubstituted alkylene or substituted or unsubstituted heteroalkylene.

The compound, wherein the substituted alkylene or substituted heteroalkylene is substituted with an azide group, a protected amino group, N-hydroxysuccinimide (NHS) group, and a protected sulfhydryl group.

The compound, wherein the substituted alkylene or heteroalkylene having a protected sulfhydryl group is conjugated to a moiety selected from the group consisting of: divinyl sulfone, acryloyl, and maleimido.

The compound, wherein the acryloyl derivative is acryloyl chloride.

The compound, wherein the linker comprises a repeating unit of a substituted alkylene or heteroalkylene group conjugated to polyethylene glycol (PEG) or bisphosphonate moiety.

The compound, wherein the linker comprises an unsubstituted heteroalkylene having three carbons.

The compound, wherein the linker comprises an unsubstituted heteroalkylene having six to twelve carbons.

The compound, wherein the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

The compound, wherein the linker is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

The compound, wherein the linker is an unsubstituted $C_1$-$C_{40}$ alkylene, unsubstituted 2 to 40 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene.

The compound, wherein the linker is a substituted 2 to 40 membered heteroalkylene.

The compound, wherein the saRNA or the ASO is chemically modified.

The compound, wherein the saRNA or the ASO comprises a chemical modification selected for the group consisting of a 2' O-Methyl, 2'-deoxy-2'fluoro, 2'-deoxy, a universal base, 5-C-methyl, an inverted deoxy abasic residue incorporation, and a locked nucleic acid.

The compound, wherein said modification is positioned at the terminal nucleobase of the saRNA or the ASO, respectively.

The compound, wherein the modification is not positioned at the terminal nucleobase of the saRNA or the ASO, respectively.

The compound, wherein the modification protects against serum-derived nucleases.

The compound, wherein the ODN sequence comprises phosphodiester derivative linkage.

The compound, wherein the phosphodiester derivative linkage in the ODN nucleic acid sequence is selected from the group consisting of: a phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, and O-methylphosphoroamidite linkage.

The compound, wherein the phosphodiester derivative linkage is a phosphorothioate linkage.

A pharmaceutical composition comprising a pharmaceutically acceptable excipient and the compound of one of claims.

The pharmaceutical composition, further comprising a second therapeutic agent.

The pharmaceutical composition, wherein the second therapeutic agent is selected from the group consisting of: anti-tumor or anti-cancer agent, cytotoxic agent, cytostatic agent, anti-inflammatory agent, analgesic, anti-infective agent, growth inhibitory agent, immunogenic agent, immunomodulatory agent, and chemokine.

The pharmaceutical composition, wherein said anti-cancer agent is a cell death promoting agent.

The pharmaceutical composition, wherein said second therapeutic agent is selected from the group consisting of: Actinomycin D/Dactinomycin, Bleomycin, Daunorubicin, Doxorubicin, Doxorubicin (pegylated liposomal), Epirubicin, Idarubicin, Mitomycin, Mitoxantrone, Etoposide, Docetaxel, Irinotecan, Paclitaxel, Topotecan, Vinblastine, Vincristine, Vinorelbine, Carboplatin, Cisplantin, Oxaliplatin, Alemtuzamab, BCG, Bevacizumab, Cetuximab, Denosumab, Erlotinib, Gefitinib, Imatinib, Interferon, Ipilimumab, Lapatinib, Monomethyl auristatin E (MMEA), Mertansine (DM1), Rituximab, Sunitinib, Sorafenib, Temsirolimus, and Trastuzumab, or any combination(s) thereof.

A method of treating cancer in a subject in need thereof, the method comprising administering to said subject an effective amount of the compound of one of claims 1-24, or the pharmaceutical composition of one of claims.

The method of treating cancer, wherein the cancer is prostate cancer, breast cancer, glioblastoma, ovarian cancer, lung cancer, head and neck cancer, esophageal cancer, skin cancer, melanoma, brain cancer, colorectal cancer, leukemia, lymphoma, or myeloma.

The method of treating cancer, wherein the cancer in the subject in treated, while simultaneously stimulating an immune response.

The method of treating cancer, wherein the compound comprises: (i) a saRNA of CEBPA, p21, or p53 conjugated to one of phosphorothioated oligodeoxynucleotides (ODN) of SEQ ID NOs: 7-18 and 98-101, or (ii) a STAT ASO of SEQ ID NOs: 31-42 and 110-113 conjugated to a phosphorothioated oligodeoxynucleotides (ODN) of sequence of SEQ ID NO: 7-18 and 98-101.

The method of treating cancer, wherein the cancer in the subject in treated without simultaneously stimulating an immune response.

The method of treating cancer, wherein the compound comprises saRNA of CEBPA, p21, or p53, or one of STAT ASO of SEQ ID NOs: 31-42 and 110-113, conjugated to one of SEQ ID NO: 29-30.

A method of treating an autoimmune disease in a subject in need thereof, the method comprising administering to said subject an effective amount of the compound of one of claims 1-24, or the pharmaceutical composition of one of claims.

The method of treating an autoimmune disease, wherein the autoimmune disease and/or disorder is rheumatoid arthritis, Crohn's disease, ulcerative colitis, multiple sclerosis, psoriasis, or systemic lupus erythematosus (SLE).

The method of treating an autoimmune disease, wherein the autoimmune disease in the subject in treated without simultaneously stimulating an immune response.

The method of treating an autoimmune disease, wherein the compound comprises one of STAT ASOs of SEQ ID NOs: 31-42 and 110-113, conjugated to one of SEQ ID NO: 29-30.

The method of treating an autoimmune disease, wherein the compound or the composition is administered to the subject by intravenous, parenteral, subcutaneous, intramuscular, transdermal, intraperitoneal, intranasal, aerosol, oral, or topical administration.

The method of treating cancer or an autoimmune disease, wherein said treatment is dose-dependent of said compound or composition.

The method of treating cancer or an autoimmune disease, wherein about 0.001 mg/kg to about 100 mg/kg of said compound is administered to said subject.

A method of stimulating an immune response in a subject in need thereof, the method comprising administering to said subject an effective amount of the compound comprising one of phosphorothioated oligodeoxynucleotides (ODN) sequence of SEQ ID NO: 7-18 and 98-101 conjugated to (i) a saRNA of CEBP, p21, or p53 or (ii) a ASOs of SEQ ID NO: 31-42 and 110-113; or the pharmaceutical composition comprising the compounds comprising one of a phosphorothioated oligodeoxynucleotides (ODN) sequence of SEQ ID NO: 7-18 and 98-101 conjugated to (i) a saRNA of CEBP, p21, or p53 or (ii) a ASOs of SEQ ID NO: 31-42 and 110-113.

The method of stimulating an immune response, wherein said stimulating comprises maturation, differentiation, or proliferation of natural killer cells, T cells, B cells or myeloid cells.

The method of stimulating an immune response, wherein said stimulating comprises an increase in $T_H1$-type immune response.

The method of stimulating an immune response, wherein said stimulating immune response recruits dendritic cells and CD8+ T cells into an organ of said subject.

The method of stimulating an immune response, wherein said stimulating immune response expands population of antigen-presenting cells in said subject.

The method of stimulating an immune response, wherein said stimulating immune response suppresses proliferation of cancer cells in said subject.

The method of stimulating an immune response, wherein the compound or the composition is administered to the subject by intravenous, parenteral, subcutaneous, intramuscular, transdermal, intraperitoneal, intranasal, aerosol, oral, or topical administration.

A method of enhancing C/EBPα expression in a cell, the method comprising contacting the cell with an effective amount of the compound comprising one of a phosphorothioated oligodeoxynucleotide (ODN) sequences of SEQ ID NO: 7-18, 29-30, and 98-101 conjugated to a saRNA of CEBP, or a pharmaceutical composition comprising the compound comprising one of a phosphorothioated oligodeoxynucleotide (ODN) sequences of SEQ ID NO: 7-18, 29-30, and 98-101 conjugated to a saRNA of CEBP.

A method of inhibiting cell growth comprising contacting said cell with an effective amount of the compound of one of claims, or the pharmaceutical composition of one of claims.

A method of reducing the activity of a STAT transcription factor in a cell comprising contacting the cell with an effective amount of the compound one of a phosphorothioated oligodeoxynucleotide (ODN) sequences of SEQ ID NO: 7-18, 29-30, and 98-101 conjugated to a ASOs of SEQ ID NO: 31-42 and 110-113, or the pharmaceutical composition comprising the compounds comprising one of a phosphorothioated oligodeoxynucleotide (ODN) sequences of SEQ ID NO: 7-18, 29-30, and 98-101 conjugated to a ASOs of SEQ ID NO: 31-42 and 110-113.

The method of one of claims, wherein said cell is a cancer cell.

The method, wherein said cell is an acute myeloid lymphoid (AML) cell or a prostate cancer cell.

The method, wherein said AML cell is from the bone marrow.

The method, wherein said cell is a cultured cell in vitro.

The method, wherein said cell is in situ in a host.

The method, wherein said cell is in a cultured tissue ex vivo.

The method, wherein said contacting step is free of viral transduction.

The method, wherein said contacting step is free of viral transduction and said cell is contacted with the compound or the pharmaceutical composition.

The method, wherein cell is contacted with about 1-100 nanomolar concentration of said compound.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

SEQUENCE LISTING

```
<160> NUMBER OF SEQ ID NOS: 113

<210> SEQ ID NO 1
<211> LENGTH: 21
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(21)
<223> OTHER INFORMATION: Residue modified with 2'-O-methyl

<400> SEQUENCE: 1
gaccagugac aaugaccgcu u                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (3)..(3)
<223> OTHER INFORMATION: Residue modified with 2'-O-methyl
<220> FEATURE:
<221> NAME/KEY: misc_feature
<222> LOCATION: (5)..(5)
<223> OTHER INFORMATION: Residue modified with 2'-O-methyl
<220> FEATURE:
<221> NAME/KEY: misc_feature
<222> LOCATION: (7)..(7)
<223> OTHER INFORMATION: Residue modified with 2'-O-methyl
<220> FEATURE:
<221> NAME/KEY: misc_feature
<222> LOCATION: (9)..(9)
<223> OTHER INFORMATION: Residue modified with 2'-O-methyl
<220> FEATURE:
<221> NAME/KEY: misc_feature
<222> LOCATION: (11)..(11)
<223> OTHER INFORMATION: Residue modified with 2'-O-methyl
```

```
<220> FEATURE:
<221> NAME/KEY: misc_feature
<222> LOCATION: (13)..(13)
<223> OTHER INFORMATION: Residue modified with 2'-O-methyl
<220> FEATURE:
<221> NAME/KEY: misc_feature
<222> LOCATION: (15)..(15)
<223> OTHER INFORMATION: Residue modified with 2'-O-methyl
<220> FEATURE:
<221> NAME/KEY: misc_feature
<222> LOCATION: (17)..(17)
<223> OTHER INFORMATION: Residue modified with 2'-O-methyl
<220> FEATURE:
<221> NAME/KEY: misc_feature
<222> LOCATION: (20)..(21)
<223> OTHER INFORMATION: Residue modified with 2'-O-methyl

<400> SEQUENCE: 2
gcggucauug ucacuggucu u                                            21

<210> SEQ ID NO 3
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 3
uacuuggaga augaguugg                                               19

<210> SEQ ID NO 4
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 4
ccaacucauu cuccaagua                                               19

<210> SEQ ID NO 5
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 5
uuaggaaggc uuuccguaa                                               19

<210> SEQ ID NO 6
<211> LENGTH: 19
<212> TYPE: RNA
<213> ORGANISM: Artificial Sequence
<220> FEATURE:
<223> OTHER INFORMATION: Synthetic polynucleotide

<400> SEQUENCE: 6
uuacggaaag ccuuccuaa                                               19

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
```

```
<223> OTHER INFORMATION: Residue modified with phosphorothioate
<220> FEATURE:
<221> NAME/KEY: misc_feature
<222> LOCATION: (16)..(20)
<223> OTHER INFORMATION: Residue modified with phosphorothioate

<400> SEQUENCE: 7
ggtgcatcga tgcagggggg                                               20

<210> SEQ ID NO 8
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified phosphorothioate

<400> SEQUENCE: 8
tcgtcgtttt gtgcttttgt cgtt                                          24

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (15)..(19)
<223> OTHER INFORMATION: Residue modified with phosphorothioate

<400> SEQUENCE: 9
ggggtcaacg ttgagggggg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (15)..(19)
<223> OTHER INFORMATION: Residue modified with phosphorothioate

<400> SEQUENCE: 10
gggggacgat cgtcgggggg                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
```

```
<222> LOCATION: (16)..(19)
<223> OTHER INFORMATION: Residue modified with phosphorothioate

<400> SEQUENCE: 11
ggtgcatcga tgcagggggg                                              20

<210> SEQ ID NO 12
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue modified with phosphorothioate
<220> FEATURE:
<221> NAME/KEY: misc_feature
<222> LOCATION: (5)..(14)
<223> OTHER INFORMATION: Residue modified with 2'-O-methyl
<220> FEATURE:
<221> NAME/KEY: misc_feature
<222> LOCATION: (16)..(20)
<223> OTHER INFORMATION: Residue modified with phosphorothioate

<400> SEQUENCE: 12
ggggacgacg tcgtgggggg g                                            21

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate

<400> SEQUENCE: 13
tccatgacgt tcctgatgct                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate

<400> SEQUENCE: 14
tccatgacgt tcctgacgtt                                              20

<210> SEQ ID NO 15
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate

<400> SEQUENCE: 15
tcgtcgtttt gtcgttttgt cgtt                                         24
```

```
<210> SEQ ID NO 16
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: Residue modified with phosphorothioate

<400> SEQUENCE: 16
tcgtcgttgt cgttttgtcg tt                                         22

<210> SEQ ID NO 17
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: Residue modified with phosphorothioate

<400> SEQUENCE: 17
tcgtcgtttt cggcgcgcgc cg                                         22

<210> SEQ ID NO 18
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(24)
<223> OTHER INFORMATION: Residue modified with phosphorothioate

<400> SEQUENCE: 18
tcgtcgtcgt tcgaacgacg ttgat                                      25

<210> SEQ ID NO 19
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
     -(CH2)n-PO4-[(CH2)n-PO4]z-(CH2)n wherein n is independently 1 to
     5 and z is independently 0 to 50
<220> FEATURE:
<221> NAME/KEY: misc_feature
<222> LOCATION: (21)..(23)
<223> OTHER INFORMATION: Residue modified with 2'-O-methyl
<220> FEATURE:
<221> NAME/KEY: misc_feature
<222> LOCATION: (24)..(33)
<223> OTHER INFORMATION: Residue modified with phosphorothioate
<220> FEATURE:
<221> NAME/KEY: misc_feature
```

```
<222> LOCATION: (34)..(36)
<223> OTHER INFORMATION: Residue modified with 2'-O-methyl

<400> SEQUENCE: 19
ggtgcatcga tgcaggggggg ctatttggat gtcagc                              36

<210> SEQ ID NO 20
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (26)..(35)
<223> OTHER INFORMATION: Residue modified with phosphorothioate
<220> FEATURE:
<221> NAME/KEY: misc_feature
<222> LOCATION: (36)..(40)
<223> OTHER INFORMATION: Residue modified with 2'-O-methyl

<400> SEQUENCE: 20
ggtgcatcga tgcaggggggg cagcagatca agtccaggga                         40

<210> SEQ ID NO 21
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (26)..(35)
<223> OTHER INFORMATION: Residue modified with phosphorothioate
<220> FEATURE:
<221> NAME/KEY: misc_feature
<222> LOCATION: (36)..(40)
<223> OTHER INFORMATION: Residue modified with 2'-O-methyl
```

<400> SEQUENCE: 21
ggtgcatcga tgcagggggg ttttgcatga tgtaaccact            40

<210> SEQ ID NO 22
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (21)..(23)
<223> OTHER INFORMATION: Residue modified with phosphorothioate
<220> FEATURE:
<221> NAME/KEY: misc_feature
<222> LOCATION: (35)..(35)
<223> OTHER INFORMATION: Residue modified with up to 4 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (47)..(49)
<223> OTHER INFORMATION: Residue modified with phosphorothioate
<220> FEATURE:
<221> NAME/KEY: misc_feature
<222> LOCATION: (50)..(50)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50

<400> SEQUENCE: 22
ggtgcatcga tgcagggggg catttcccgt aaatcgattt acgggaaatg            50

<210> SEQ ID NO 23
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (21)..(23)
<223> OTHER INFORMATION: Residue modified with phosphorothioate
<220> FEATURE:
<221> NAME/KEY: misc_feature
<222> LOCATION: (35)..(35)
<223> OTHER INFORMATION: Residue modified with up to 4 repetitions of -(CH2)n-PO4-[(CH2)n-PO4]z-(CH2)n wherein n is independently 1 to
5 and z is independently 0 to 50
<220> FEATURE:
<221> NAME/KEY: misc_feature
<222> LOCATION: (47)..(49)
<223> OTHER INFORMATION: Residue modified with phosphorothioate
<220> FEATURE:
<221> NAME/KEY: misc_feature
<222> LOCATION: (50)..(50)
<223> OTHER INFORMATION: Residue modified with up to 5 repetitions of
-(CH2)n-PO4-[(CH2)n-PO4]z-(CH2)n wherein n is independently 1 to
5 and z is independently 0 to 50

<400> SEQUENCE: 23
ggtgcatgca tgcagggggg catttcccgt aaatcgattt acgggaaatg            50

<210> SEQ ID NO 24
<211> LENGTH: 50
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
-(CH2)n-PO4-[(CH2)n-PO4]z-(CH2)n wherein n is independently 1 to
5 and z is independently 0 to 50
<220> FEATURE:
<221> NAME/KEY: misc_feature
<222> LOCATION: (21)..(23)
<223> OTHER INFORMATION: Residue modified with phosphorothioate
<220> FEATURE:
<221> NAME/KEY: misc_feature
<222> LOCATION: (35)..(35)
<223> OTHER INFORMATION: Residue modified with up to 4 repetitions of
-(CH2)n-PO4-[(CH2)n-PO4]z-(CH2)n wherein n is independently 1 to
5 and z is independently 0 to 50
<220> FEATURE:
<221> NAME/KEY: misc_feature
<222> LOCATION: (47)..(49)
<223> OTHER INFORMATION: Residue modified with phosphorothioate
<220> FEATURE:
<221> NAME/KEY: misc_feature
<222> LOCATION: (50)..(50)
<223> OTHER INFORMATION: Residue modified with up to 5 repetitions of
-(CH2)n-PO4-[(CH2)n-PO4]z-(CH2)n wherein n is independently 1 to
5 and z is independently 0 to 50

<400> SEQUENCE: 24
ggtgcatcga tgcagggggg actcttgcca attacgtaat tggcaagagt            50

<210> SEQ ID NO 25
<211> LENGTH: 54
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
-(CH2)n-PO4-[(CH2)n-PO4]z-(CH2)n wherein n is independently 1 to 5 and z is independently 0 to 50
<220> FEATURE:
<221> NAME/KEY: misc_feature
<222> LOCATION: (25)..(27)
<223> OTHER INFORMATION: Residue modified with phosphorothioate
<220> FEATURE:
<221> NAME/KEY: misc_feature
<222> LOCATION: (39)..(39)
<223> OTHER INFORMATION: Residue modified with up to 4 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (51)..(53)
<223> OTHER INFORMATION: Residue modified with phosphorothioate
<220> FEATURE:
<221> NAME/KEY: misc_feature
<222> LOCATION: (54)..(54)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50

<400> SEQUENCE: 25
tcgtcgtttt gtcgttttgt cgttcatttc ccgtaaatcg atttacggga aatg        54

<210> SEQ ID NO 26
<211> LENGTH: 54
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (25)..(27)
<223> OTHER INFORMATION: Residue modified with phosphorothioate
<220> FEATURE:
<221> NAME/KEY: misc_feature
<222> LOCATION: (39)..(39)
<223> OTHER INFORMATION: Residue modified with up to 4 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (51)..(53)
<223> OTHER INFORMATION: Residue modified with phosphorothioate
<220> FEATURE:
<221> NAME/KEY: misc_feature
<222> LOCATION: (54)..(54)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50

<400> SEQUENCE: 26
tcgtcgtttt gtcgttttgt cgttcatttc ccttaaatcg atttaaggga aatg        54

<210> SEQ ID NO 27
<211> LENGTH: 54
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate

```
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (26)..(27)
<223> OTHER INFORMATION: Residue modified with phosphorothioate
<220> FEATURE:
<221> NAME/KEY: misc_feature
<222> LOCATION: (39)..(39)
<223> OTHER INFORMATION: Residue modified with up to 4 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (51)..(53)
<223> OTHER INFORMATION: Residue modified with phosphorothioate
<220> FEATURE:
<221> NAME/KEY: misc_feature
<222> LOCATION: (54)..(54)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50

<400> SEQUENCE: 27
tcgtcgtttt gtcgttttgt cgttactctt gccaattacg taattggcaa gagt           54

<210> SEQ ID NO 28
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue modified with phosphorothioate
<220> FEATURE:
<221> NAME/KEY: misc_feature
<222> LOCATION: (1)..(1)
<223> OTHER INFORMATION: Residue modified at 5'-terminal with up to 5
      repetitions of -(CH2)n-PO4-[(CH2)n-PO4]z-(CH2)n wherein n is
      independently 1 to 5 and z is independently 0 to 50
<220> FEATURE:
<221> NAME/KEY: misc_feature
<222> LOCATION: (15)..(15)
<223> OTHER INFORMATION: Residue modified with up to 4 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (27)..(29)
<223> OTHER INFORMATION: Residue modified with phosphorothioate
<220> FEATURE:
<221> NAME/KEY: misc_feature
<222> LOCATION: (30)..(30)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50

<400> SEQUENCE: 28
catttcccgt aaatcgattt acgggaaatg                                      30

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
```

```
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate

<400> SEQUENCE: 29
ggtgcatgca tgcaggggggg                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (8)..(9)
<223> OTHER INFORMATION: Sequence is cg or gc

<400> SEQUENCE: 30
ggtgcatssa tgcaggggggg                                              20

<210> SEQ ID NO 31
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue modified with 2'-O-methyl
<220> FEATURE:
<221> NAME/KEY: misc_feature
<222> LOCATION: (4)..(13)
<223> OTHER INFORMATION: Residue modified with phosphorothioate
<220> FEATURE:
<221> NAME/KEY: misc_feature
<222> LOCATION: (14)..(16)
<223> OTHER INFORMATION: Residue modified with 2'-O-methyl

<400> SEQUENCE: 31
ctatttggat gtcagc                                                   16

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: Residue modified with 2'-O-methyl
<220> FEATURE:
<221> NAME/KEY: misc_feature
<222> LOCATION: (6)..(15)
<223> OTHER INFORMATION: Residue modified with phosphorothioate
<220> FEATURE:
<221> NAME/KEY: misc_feature
<222> LOCATION: (16)..(20)
<223> OTHER INFORMATION: Residue modified with 2'-O-methyl

<400> SEQUENCE: 32
cagcagatca agtccaggga                                               20
```

```
<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: Residue modified with 2'-O-methyl
<220> FEATURE:
<221> NAME/KEY: misc_feature
<222> LOCATION: (6)..(15)
<223> OTHER INFORMATION: Residue modified with phosphorothioate
<220> FEATURE:
<221> NAME/KEY: misc_feature
<222> LOCATION: (16)..(20)
<223> OTHER INFORMATION: Residue modified with 2'-O-methyl

<400> SEQUENCE: 33
ttttgcatga tgtaaccact                                                 20

<210> SEQ ID NO 34
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue modified with 2'-O-methyl
<220> FEATURE:
<221> NAME/KEY: misc_feature
<222> LOCATION: (1)..(15)
<223> OTHER INFORMATION: Residue modified with phosphorothioate
<220> FEATURE:
<221> NAME/KEY: misc_feature
<222> LOCATION: (14)..(16)
<223> OTHER INFORMATION: Residue modified with 2'-O-methyl

<400> SEQUENCE: 34
ctatttggat gtcagc                                                     16

<210> SEQ ID NO 35
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: Residue modified with 2'-O-methyl
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (16)..(20)
<223> OTHER INFORMATION: Residue modified with 2'-O-methyl

<400> SEQUENCE: 35
cagcagatca agtccaggga                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (1)..(5)
<223> OTHER INFORMATION: Residue modified with 2'-O-methyl
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (16)..(20)
<223> OTHER INFORMATION: Residue modified with 2'-O-methyl

<400> SEQUENCE: 36
ttttgcatga tgtaaccact                                               20

<210> SEQ ID NO 37
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(18)
<223> OTHER INFORMATION: Residue modified with 2'-O-methyl
<220> FEATURE:
<221> NAME/KEY: misc_feature
<222> LOCATION: (1)..(17)
<223> OTHER INFORMATION: Residue modified with phosphorothioate

<400> SEQUENCE: 37
atcaaagtca tcctggag                                                 18

<210> SEQ ID NO 38
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue is LNA
<220> FEATURE:
<221> NAME/KEY: misc_feature
<222> LOCATION: (1)..(15)
<223> OTHER INFORMATION: Residue modified with phosphorothioate
<220> FEATURE:
<221> NAME/KEY: misc_feature
<222> LOCATION: (14)..(16)
<223> OTHER INFORMATION: Residue is LNA

<400> SEQUENCE: 38
gcaacctgac tttagt                                                   16

<210> SEQ ID NO 39
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue is LNA
<220> FEATURE:
<221> NAME/KEY: misc_feature
<222> LOCATION: (1)..(15)
<223> OTHER INFORMATION: Residue modified with phosphorothioate
<220> FEATURE:
<221> NAME/KEY: misc_feature
<222> LOCATION: (14)..(16)
<223> OTHER INFORMATION: Residue is LNA
```

<400> SEQUENCE: 39
gattctgcta atgacg                                                              16

<210> SEQ ID NO 40
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue is LNA
<220> FEATURE:
<221> NAME/KEY: misc_feature
<222> LOCATION: (1)..(15)
<223> OTHER INFORMATION: Residue modified with phosphorothioate
<220> FEATURE:
<221> NAME/KEY: misc_feature
<222> LOCATION: (14)..(16)
<223> OTHER INFORMATION: Residue is LNA

<400> SEQUENCE: 40
tgacgggtct gaagtt                                                              16

<210> SEQ ID NO 41
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue is LNA
<220> FEATURE:
<221> NAME/KEY: misc_feature
<222> LOCATION: (1)..(15)
<223> OTHER INFORMATION: Residue modified with phosphorothioate
<220> FEATURE:
<221> NAME/KEY: misc_feature
<222> LOCATION: (14)..(16)
<223> OTHER INFORMATION: Residue is LNA

<400> SEQUENCE: 41
agatagcaga agtagg                                                              16

<210> SEQ ID NO 42
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue is LNA
<220> FEATURE:
<221> NAME/KEY: misc_feature
<222> LOCATION: (1)..(15)
<223> OTHER INFORMATION: Residue modified with phosphorothioate
<220> FEATURE:
<221> NAME/KEY: misc_feature
<222> LOCATION: (14)..(16)
<223> OTHER INFORMATION: Residue is LNA

<400> SEQUENCE: 42
gtcaatgcac acttta                                                              16

<210> SEQ ID NO 43

```
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(23)
<223> OTHER INFORMATION: Residue modified with 2'-O-methyl
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (34)..(36)
<223> OTHER INFORMATION: Residue modified with 2'-O-methyl

<400> SEQUENCE: 43
ggtgcatcga tgcagggggg ctatttggat gtcagc                              36

<210> SEQ ID NO 44
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothionate
<220> FEATURE:
<221> NAME/KEY: misc_feature
<222> LOCATION: (16)..(19)
<223> OTHER INFORMATION: Residue modified with phosphorothionate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(39)
<223> OTHER INFORMATION: Residue modified with phosphorothionate
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (36)..(40)
<223> OTHER INFORMATION: Residue modified with 2'-O-methyl

<400> SEQUENCE: 44
ggtgcatcga tgcagggggg cagcagatca agtccaggga                          40

<210> SEQ ID NO 45
<211> LENGTH: 40
<212> TYPE: DNA
<213> ORGANISM: Artificial Sequence
```

```
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(39)
<223> OTHER INFORMATION: Residue modified with phosphorothioate
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (36)..(40)
<223> OTHER INFORMATION: Residue modified with 2'-O-methyl

<400> SEQUENCE: 45
ggtgcatcga tgcagggggg ttttgcatga tgtaaccact                        40

<210> SEQ ID NO 46
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(37)
<223> OTHER INFORMATION: Residue modified with phosphorothioate
<220> FEATURE:
<221> NAME/KEY: misc_feature
<222> LOCATION: (21)..(38)
<223> OTHER INFORMATION: Residue modified with 2'-O-methyl

<400> SEQUENCE: 46
ggtgcatcga tgcagggggg atcaaagtca tcctggag                         38

<210> SEQ ID NO 47
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
```

```
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 47
ggtgcatcga tgcagggggg gcaacctgac tttagt                         36

<210> SEQ ID NO 48
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 48
ggtgcatcga tgcagggggg gattctgcta atgacg                         36

<210> SEQ ID NO 49
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
```

```
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 49
ggtgcatcga tgcagggggg tgacgggtct gaagtt                               36

<210> SEQ ID NO 50
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 50
ggtgcatcga tgcagggggg agatagcaga agtagg                               36

<210> SEQ ID NO 51
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
```

```
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 51
ggtgcatcga tgcagggggg gtcaatgcac acttta                                 36

<210> SEQ ID NO 52
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue modified with 2'-O-methyl
<220> FEATURE:
<221> NAME/KEY: misc_feature
<222> LOCATION: (38)..(40)
<223> OTHER INFORMATION: Residue modified with 2'-O-methyl

<400> SEQUENCE: 52
tcgtcgtttt gtcgttttgt cgttctattt ggatgtcagc                             40

<210> SEQ ID NO 53
<211> LENGTH: 44
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(43)
<223> OTHER INFORMATION: Residue modified with phosphorothioate
<220> FEATURE:
<221> NAME/KEY: misc_feature
<222> LOCATION: (25)..(29)
<223> OTHER INFORMATION: Residue modified with 2'-O-methyl
```

```
<220> FEATURE:
<221> NAME/KEY: misc_feature
<222> LOCATION: (40)..(44)
<223> OTHER INFORMATION: Residue modified with 2'-O-methyl

<400> SEQUENCE: 53
tcgtcgtttt gtcgttttgt cgttcagcag atcaagtcca ggga                44

<210> SEQ ID NO 54
<211> LENGTH: 44
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(43)
<223> OTHER INFORMATION: Residue modified with phosphorothioate
<220> FEATURE:
<221> NAME/KEY: misc_feature
<222> LOCATION: (25)..(29)
<223> OTHER INFORMATION: Residue modified with 2'-O-methyl
<220> FEATURE:
<221> NAME/KEY: misc_feature
<222> LOCATION: (40)..(44)
<223> OTHER INFORMATION: Residue modified with 2'-O-methyl

<400> SEQUENCE: 54
tcgtcgtttt gtcgttttgt cgttttttgc atgatgtaac cact                44

<210> SEQ ID NO 55
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(41)
<223> OTHER INFORMATION: Residue modified with phosphorothioate
<220> FEATURE:
<221> NAME/KEY: misc_feature
<222> LOCATION: (25)..(42)
<223> OTHER INFORMATION: Residue modified with 2'-O-methyl

<400> SEQUENCE: 55
tcgtcgtttt gtcgttttgt cgttatcaaa gtcatcctgg ag                  42

<210> SEQ ID NO 56
<211> LENGTH: 40
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
<223> OTHER INFORMATION: Residue is LNA

<400> SEQUENCE: 56
tcgtcgtttt gtcgttttgt cgttgcaacc tgactttagt                              40

<210> SEQ ID NO 57
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
<223> OTHER INFORMATION: Residue is LNA

<400> SEQUENCE: 57
tcgtcgtttt gtcgttttgt cgttgattct gctaatgacg                              40

<210> SEQ ID NO 58
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
```

```
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
<223> OTHER INFORMATION: Residue is LNA

<400> SEQUENCE: 58
tcgtcgtttt gtcgttttgt cgtttgacgg gtctgaagtt                            40

<210> SEQ ID NO 59
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
<223> OTHER INFORMATION: Residue is LNA

<400> SEQUENCE: 59
tcgtcgtttt gtcgttttgt cgttagatag cagaagtagg                            40

<210> SEQ ID NO 60
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
```

<223> OTHER INFORMATION: Residue is LNA

<400> SEQUENCE: 60
tcgtcgtttt gtcgttttgt cgttgtcaat gcacacttta                    40

<210> SEQ ID NO 61
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue modified with 2'-O-methyl
<220> FEATURE:
<221> NAME/KEY: misc_feature
<222> LOCATION: (34)..(36)
<223> OTHER INFORMATION: Residue modified with 2'-O-methyl

<400> SEQUENCE: 61
ggtgcatgca tgcagggggg ctatttggat gtcagc                       36

<210> SEQ ID NO 62
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(39)
<223> OTHER INFORMATION: Residue modified with phosphorothioate
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (36)..(40)
<223> OTHER INFORMATION: Residue modified with 2'-O-methyl

<400> SEQUENCE: 62

```
ggtgcatgca tgcaggggggg cagcagatca agtccaggga                    40
```

<210> SEQ ID NO 63
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
     -(CH2)n-PO4-[(CH2)n-PO4]z-(CH2)n wherein n is independently 1 to
     5 and z is independently 0 to 50
<220> FEATURE:
<221> NAME/KEY: misc_feature
<222> LOCATION: (21)..(39)
<223> OTHER INFORMATION: Residue modified with phosphorothioate
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (36)..(40)
<223> OTHER INFORMATION: Residue modified with 2'-O-methyl

<400> SEQUENCE: 63

```
ggtgcatgca tgcaggggggg ttttgcatga tgtaaccact                    40
```

<210> SEQ ID NO 64
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
     -(CH2)n-PO4-[(CH2)n-PO4]z-(CH2)n wherein n is independently 1 to
     5 and z is independently 0 to 50
<220> FEATURE:
<221> NAME/KEY: misc_feature
<222> LOCATION: (21)..(37)
<223> OTHER INFORMATION: Residue modified with phosphorothioate
<220> FEATURE:
<221> NAME/KEY: misc_feature
<222> LOCATION: (21)..(38)
<223> OTHER INFORMATION: Residue modified with 2'-O-methyl

<400> SEQUENCE: 64

```
ggtgcatgca tgcaggggggg atcaaagtca tcctggag                      38
```

<210> SEQ ID NO 65
<211> LENGTH: 36
<212> TYPE: DNA

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 65
ggtgcatgca tgcaggggggg gcaacctgac tttagt                              36

<210> SEQ ID NO 66
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 66
ggtgcatgca tgcaggggggg gattctgcta atgacg                              36

<210> SEQ ID NO 67
<211> LENGTH: 36
<212> TYPE: DNA
<213> ORGANISM: Artificial Sequence
<220> FEATURE:
<223> OTHER INFORMATION: Synthetic polynucleotide
```

```
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
     -(CH2)n-PO4-[(CH2)n-PO4]z-(CH2)n wherein n is independently 1 to
     5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 67
ggtgcatgca tgcagggggg tgacgggtct gaagtt                              36

<210> SEQ ID NO 68
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
     -(CH2)n-PO4-[(CH2)n-PO4]z-(CH2)n wherein n is independently 1 to
     5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 68
ggtgcatgca tgcagggggg agatagcaga agtagg                              36

<210> SEQ ID NO 69
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
```

<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 69
ggtgcatgca tgcagggggg gtcaatgcac acttta                               36

<210> SEQ ID NO 70
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue modified with 2'-O-methyl
<220> FEATURE:
<221> NAME/KEY: misc_feature
<222> LOCATION: (38)..(40)
<223> OTHER INFORMATION: Residue modified with 2'-O-methyl

<400> SEQUENCE: 70
tgctgctttt gtgcttttgt gcttctattt ggatgtcagc                           40

<210> SEQ ID NO 71
<211> LENGTH: 44
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50

```
<220> FEATURE:
<221> NAME/KEY: misc_feature
<222> LOCATION: (25)..(43)
<223> OTHER INFORMATION: Residue modified with phosphorothioate
<220> FEATURE:
<221> NAME/KEY: misc_feature
<222> LOCATION: (25)..(29)
<223> OTHER INFORMATION: Residue modified with 2'-O-methyl
<220> FEATURE:
<221> NAME/KEY: misc_feature
<222> LOCATION: (40)..(44)
<223> OTHER INFORMATION: Residue modified with 2'-O-methyl

<400> SEQUENCE: 71
tgctgctttt gtgcttttgt gcttcagcag atcaagtcca ggga            44

<210> SEQ ID NO 72
<211> LENGTH: 44
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(43)
<223> OTHER INFORMATION: Residue modified with phosphorothioate
<220> FEATURE:
<221> NAME/KEY: misc_feature
<222> LOCATION: (25)..(29)
<223> OTHER INFORMATION: Residue modified with 2'-O-methyl
<220> FEATURE:
<221> NAME/KEY: misc_feature
<222> LOCATION: (40)..(44)
<223> OTHER INFORMATION: Residue modified with 2'-O-methyl

<400> SEQUENCE: 72
tgctgctttt gtgcttttgt gctttttgc atgatgtaac cact            44

<210> SEQ ID NO 73
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(41)
<223> OTHER INFORMATION: Residue modified with phosphorothioate
<220> FEATURE:
<221> NAME/KEY: misc_feature
<222> LOCATION: (25)..(42)
<223> OTHER INFORMATION: Residue modified with 2'-O-methyl

<400> SEQUENCE: 73
```
tgctgctttt gtgcttttgt gcttatcaaa gtcatcctgg ag                    42

<210> SEQ ID NO 74
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
<223> OTHER INFORMATION: Residue is LNA

<400> SEQUENCE: 74
tgctgctttt gtgcttttgt gcttgcaacc tgactttagt                       40

<210> SEQ ID NO 75
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
<223> OTHER INFORMATION: Residue is LNA

<400> SEQUENCE: 75
tgctgctttt gtgcttttgt gcttgattct gctaatgacg                       40

<210> SEQ ID NO 76
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature

```
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
<223> OTHER INFORMATION: Residue is LNA

<400> SEQUENCE: 76
tgctgctttt gtgcttttgt gctttgacgg gtctgaagtt                              40

<210> SEQ ID NO 77
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate
<220> FEATURE:
<221> NAME/KEY: misc_feature
<222> LOCATION: (24)..(24)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (25)..(39)
<223> OTHER INFORMATION: Residue modified with phosphorothioate
<220> FEATURE:
<221> NAME/KEY: misc_feature
<222> LOCATION: (25)..(27)
<223> OTHER INFORMATION: Residue is LNA
<220> FEATURE:
<221> NAME/KEY: misc_feature
<222> LOCATION: (38)..(40)
<223> OTHER INFORMATION: Residue is LNA

<400> SEQUENCE: 77
tgctgctttt gtgcttttgt gcttagatag cagaagtagg                              40

<210> SEQ ID NO 78
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
```

<223> OTHER INFORMATION: Residue modified with phosphorothioate
<220> FEATURE:
<221> NAME/KEY: misc_feature
<222> LOCATION: (21)..(23)
<223> OTHER INFORMATION: Residue modified with 2'-O-methyl
<220> FEATURE:
<221> NAME/KEY: misc_feature
<222> LOCATION: (34)..(36)
<223> OTHER INFORMATION: Residue modified with 2'-O-methyl

<400> SEQUENCE: 78
ggtgcatcga tgcagggggg ctatttggat gtcagc                               36

<210> SEQ ID NO 79
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(39)
<223> OTHER INFORMATION: Residue modified with phosphorothioate
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (36)..(40)
<223> OTHER INFORMATION: Residue modified with 2'-O-methyl

<400> SEQUENCE: 79
ggtgcatcga tgcagggggg cagcagatca agtccaggga                           40

<210> SEQ ID NO 80
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(39)
<223> OTHER INFORMATION: Residue modified with phosphorothioate
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (36)..(40)
<223> OTHER INFORMATION: Residue modified with 2'-O-methyl

<400> SEQUENCE: 80
ggtgcatcga tgcaggggggg ttttgcatga tgtaaccact         40

<210> SEQ ID NO 81
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(37)
<223> OTHER INFORMATION: Residue modified with phosphorothioate
<220> FEATURE:
<221> NAME/KEY: misc_feature
<222> LOCATION: (21)..(38)
<223> OTHER INFORMATION: Residue modified with 2'-O-methyl

<400> SEQUENCE: 81
ggtgcatcga tgcaggggggg atcaaagtca tcctggag         38

<210> SEQ ID NO 82
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 82
ggtgcatcga tgcaggggggg gcaacctgac tttagt         36

<210> SEQ ID NO 83
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:

-continued

```
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 83
ggtgcatcga tgcagggggg gattctgcta atgacg                                 36

<210> SEQ ID NO 84
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 84
ggtgcatcga tgcagggggg tgacgggtct gaagtt                                 36

<210> SEQ ID NO 85
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
```

<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 85
ggtgcatcga tgcaggggg agatagcaga agtagg                          36

<210> SEQ ID NO 86
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 86
ggtgcatcga tgcaggggg gtcaatgcac acttta                          36

<210> SEQ ID NO 87
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue modified with 2'-O-methyl
<220> FEATURE:
<221> NAME/KEY: misc_feature
<222> LOCATION: (34)..(36)
<223> OTHER INFORMATION: Residue modified with 2'-O-methyl

<400> SEQUENCE: 87
ggtgcatgca tgcaggggg ctatttggat gtcagc                          36

```
<210> SEQ ID NO 88
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(39)
<223> OTHER INFORMATION: Residue modified with phosphorothioate
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (36)..(40)
<223> OTHER INFORMATION: Residue modified with 2'-O-methyl

<400> SEQUENCE: 88
ggtgcatgca tgcagggggg cagcagatca agtccaggga                40

<210> SEQ ID NO 89
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(39)
<223> OTHER INFORMATION: Residue modified with phosphorothioate
<220> FEATURE:
<221> NAME/KEY: misc_feature
<222> LOCATION: (21)..(25)
<223> OTHER INFORMATION: Residue modified with 2'-O-methyl
<220> FEATURE:
<221> NAME/KEY: misc_feature
<222> LOCATION: (36)..(40)
<223> OTHER INFORMATION: Residue modified with 2'-O-methyl

<400> SEQUENCE: 89
ggtgcatgca tgcagggggg ttttgcatga tgtaaccact                40

<210> SEQ ID NO 90
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
```

```
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(37)
<223> OTHER INFORMATION: Residue modified with phosphorothioate
<220> FEATURE:
<221> NAME/KEY: misc_feature
<222> LOCATION: (21)..(38)
<223> OTHER INFORMATION: Residue modified with 2'-O-methyl

<400> SEQUENCE: 90
ggtgcatgca tgcagggggg atcaaagtca tcctggag                           38

<210> SEQ ID NO 91
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 91
ggtgcatgca tgcagggggg gcaacctgac tttagt                             36

<210> SEQ ID NO 92
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
```

```
<221> NAME/KEY: misc_feature
<222> LOCATION: (34)..(36)
<223> OTHER INFORMATION: Residue is LNA

<400> SEQUENCE: 92
ggtgcatgca tgcaggggggg gattctgcta atgacg                              36

<210> SEQ ID NO 93
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 93
ggtgcatgca tgcaggggggg tgacgggtct gaagtt                              36

<210> SEQ ID NO 94
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
      -(CH2)n-PO4-[(CH2)n-PO4]z-(CH2)n wherein n is independently 1 to
      5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 94
ggtgcatgca tgcaggggggg agatagcaga agtagg                              36

<210> SEQ ID NO 95
<211> LENGTH: 36
```

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with up to 5 repetitions of
    -(CH2)n-PO4-[(CH2)n-PO4]z-(CH2)n wherein n is independently 1 to
    5 and z is independently 0 to 50
<220> FEATURE:
<221> NAME/KEY: misc_feature
<222> LOCATION: (21)..(35)
<223> OTHER INFORMATION: Residue modified with phosphorothioate
<220> FEATURE:
<221> NAME/KEY: misc_feature
<222> LOCATION: (21)..(23)
<223> OTHER INFORMATION: Residue is LNA
<220> FEATURE:
<221> NAME/KEY: misc_feature
<222> LOCATION: (34)..(36)
<223> OTHER INFORMATION: Residue is LNA

<400> SEQUENCE: 95
ggtgcatgca tgcagggggg gtcaatgcac acttta                              36

<210> SEQ ID NO 96
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 96
ctgcctagat cggctagaaa ac                                             22

<210> SEQ ID NO 97
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 97
ccctttgtag gaaactttt gc                                              22

<210> SEQ ID NO 98
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Residue modified with phosphorothioate

<400> SEQUENCE: 98
tcgtcgtttt gtcgttttgt cctt                                           24

<210> SEQ ID NO 99
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (1)..(23)
<223> OTHER INFORMATION: Residue modified with phosphorothioate

<400> SEQUENCE: 99
tcctcgtttt gtcgttttgt cctt                                           24

<210> SEQ ID NO 100
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue modified with phosphorothioate
<220> FEATURE:
<221> NAME/KEY: misc_feature
<222> LOCATION: (15)..(19)
<223> OTHER INFORMATION: Residue modified with phosphorothioate

<400> SEQUENCE: 100
ggggtcaacg ttgagggggg                                                20

<210> SEQ ID NO 101
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(20)
<223> OTHER INFORMATION: Residue modified with phosphorothioate

<400> SEQUENCE: 101
ggggacgacg tcgtggggggg g                                             21

<210> SEQ ID NO 102
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(20)
<223> OTHER INFORMATION: Residue modified with phosphorothioate

<400> SEQUENCE: 102
ggtgcatcga tgcagggggg                                                20

<210> SEQ ID NO 103
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
```

-continued

```
<220> FEATURE:
<221> NAME/KEY: misc_feature
<222> LOCATION: (20)..(20)
<223> OTHER INFORMATION: Residue modified with 5 repetitions of C3
      linker [-(CH2)3-]
<220> FEATURE:
<221> NAME/KEY: misc_feature
<222> LOCATION: (40)..(41)
<223> OTHER INFORMATION: Residue modified with 2'-O-methyl

<400> SEQUENCE: 103
ggtgcatcga tgcagggggg gaccagugac aaugaccgcu u                    41

<210> SEQ ID NO 104
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with 5 repetitions of C3
      linker [-(CH2)3-]
<220> FEATURE:
<221> NAME/KEY: misc_feature
<222> LOCATION: (23)..(23)
<223> OTHER INFORMATION: Residue modified with 2'-O-methyl
<220> FEATURE:
<221> NAME/KEY: misc_feature
<222> LOCATION: (25)..(25)
<223> OTHER INFORMATION: Residue modified with 2'-O-methyl
<220> FEATURE:
<221> NAME/KEY: misc_feature
<222> LOCATION: (27)..(27)
<223> OTHER INFORMATION: Residue modified with 2'-O-methyl
<220> FEATURE:
<221> NAME/KEY: misc_feature
<222> LOCATION: (29)..(29)
<223> OTHER INFORMATION: Residue modified with 2'-O-methyl
<220> FEATURE:
<221> NAME/KEY: misc_feature
<222> LOCATION: (31)..(31)
<223> OTHER INFORMATION: Residue modified with 2'-O-methyl
<220> FEATURE:
<221> NAME/KEY: misc_feature
<222> LOCATION: (33)..(33)
<223> OTHER INFORMATION: Residue modified with 2'-O-methyl
<220> FEATURE:
<221> NAME/KEY: misc_feature
<222> LOCATION: (35)..(35)
<223> OTHER INFORMATION: Residue modified with 2'-O-methyl
<220> FEATURE:
<221> NAME/KEY: misc_feature
<222> LOCATION: (37)..(37)
<223> OTHER INFORMATION: Residue modified with 2'-O-methyl
<220> FEATURE:
<221> NAME/KEY: misc_feature
<222> LOCATION: (40)..(41)
<223> OTHER INFORMATION: Residue modified with 2'-O-methyl

<400> SEQUENCE: 104
ggtgcatcga tgcagggggg gcggucauug ucacuggucu u                    41

<210> SEQ ID NO 105
<211> LENGTH: 21
<212> TYPE: RNA
```

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(21)
<223> OTHER INFORMATION: Residue modified with 2'-O-methyl

<400> SEQUENCE: 105
gaccagugac aaugaccgcu u                                              21

<210> SEQ ID NO 106
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with 5 repetitions of C3
      linker [-(CH2)3-]
<220> FEATURE:
<221> NAME/KEY: misc_feature
<222> LOCATION: (41)..(41)
<223> OTHER INFORMATION: Residue modified with 2'-O-methyl

<400> SEQUENCE: 106
ggtgcatcga tgcagggggg ugaccaguga caaugaccgu u                        41

<210> SEQ ID NO 107
<211> LENGTH: 21
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(21)
<223> OTHER INFORMATION: Residue modified with 2'-O-methyl

<400> SEQUENCE: 107
cggucauugu cacuggucau u                                              21

<210> SEQ ID NO 108
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: Residue modified with phosphorothioate
<220> FEATURE:
<221> NAME/KEY: misc_feature
<222> LOCATION: (16)..(19)
<223> OTHER INFORMATION: Residue modified with phosphorothioate
<220> FEATURE:
<221> NAME/KEY: misc_feature
<222> LOCATION: (20)..(20)
<223> OTHER INFORMATION: Residue modified with 5 repetitions of C3
      linker [-(CH2)3-]
<220> FEATURE:
<221> NAME/KEY: misc_feature
```

```
<222> LOCATION: (41)..(41)
<223> OTHER INFORMATION: Residue modified with 2'-O-methyl

<400> SEQUENCE: 108
ggtgcatcga tgcaggggggg cggucauugu cacuggucau u                 41

<210> SEQ ID NO 109
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(21)
<223> OTHER INFORMATION: Residue modified with 2'-O-methyl

<400> SEQUENCE: 109
ugaccaguga caaugaccgu u                                        21

<210> SEQ ID NO 110
<211> LENGTH: 16
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue modified with 2'-O-methyl
<220> FEATURE:
<221> NAME/KEY: misc_feature
<222> LOCATION: (1)..(16)
<223> OTHER INFORMATION: Residue modified with phosphorothioate
<220> FEATURE:
<221> NAME/KEY: misc_feature
<222> LOCATION: (14)..(16)
<223> OTHER INFORMATION: Residue modified with 2'-O-methyl

<400> SEQUENCE: 110
ctatttggat gtcagc                                              16

<210> SEQ ID NO 111
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: Residue modified with 2'-O-methyl
<220> FEATURE:
<221> NAME/KEY: misc_feature
<222> LOCATION: (1)..(20)
<223> OTHER INFORMATION: Residue modified with phosphorothioate
<220> FEATURE:
<221> NAME/KEY: misc_feature
<222> LOCATION: (16)..(20)
<223> OTHER INFORMATION: Residue modified with 2'-O-methyl

<400> SEQUENCE: 111
cagcagatca agtccaggga                                          20

<210> SEQ ID NO 112
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (1)..(3)
<223> OTHER INFORMATION: Residue modified with 2'-O-methyl
<220> FEATURE:
<221> NAME/KEY: misc_feature
<222> LOCATION: (1)..(20)
<223> OTHER INFORMATION: Residue modified with phosphorothioate
<220> FEATURE:
<221> NAME/KEY: misc_feature
<222> LOCATION: (18)..(20)
<223> OTHER INFORMATION: Residue modified with 2'-O-methyl

<400> SEQUENCE: 112
aaaaagtgcc cagattgccc                                              20

<210> SEQ ID NO 113
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue modified with 2'-O-methyl
<220> FEATURE:
<221> NAME/KEY: misc_feature
<222> LOCATION: (1)..(20)
<223> OTHER INFORMATION: Residue modified with phosphorothioate
<220> FEATURE:
<221> NAME/KEY: misc_feature
<222> LOCATION: (18)..(20)
<223> OTHER INFORMATION: Residue modified with 2'-O-methyl

<400> SEQUENCE: 113
actcaaactg ccctcctgct                                              20
```

What is claimed is:

1. An isolated compound comprising a phosphorothioated oligodeoxynucleotide (ODN) sequence conjugated to: (i) a short-activating RNA (saRNA) of CCAAT/enhancer-binding protein-α (C/EBPα), p21, or p53 or (ii) an antisense oligonucleotide (ASO) sequence of Signal Transducer and Activator of Transcription (STAT), wherein the ASO comprises a single-stranded DNA substituent.

2. The compound of claim 1, wherein said antisense oligonucleotide sequence is an anti-STAT1 oligonucleotide sequence, anti-STAT2 oligonucleotide sequence oligonucleotide sequence, anti-STAT3 oligonucleotide sequence, anti-STAT4 oligonucleotide sequence, anti-STAT5A oligonucleotide sequence, anti-STAT5B oligonucleotide sequence, or anti-STAT6 oligonucleotide sequence.

3. The compound of claim 1, further comprising a linker between the phosphorothioated ODN sequence and the short-activating RNA (saRNA) or the ASO.

4. The compound of claim 3, wherein the linker is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

5. The compound of claim 3, wherein the linker is a substituted 2 to 40 membered heteroalkylene.

6. The compound of claim 1, wherein the saRNA or the ASO comprises a chemical modification selected for the group consisting of a 2' O-Methyl, 2'-deoxy-2'fluoro, 2'-deoxy, a universal base, 5-C-methyl, an inverted deoxy abasic residue incorporation, and a locked nucleic acid.

7. A pharmaceutical composition comprising a pharmaceutically acceptable excipient and the compound of claim 1.

8. The pharmaceutical composition of claim 7, further comprising a second therapeutic agent.

9. The pharmaceutical composition of claim 8, wherein the second therapeutic agent is selected from the group consisting of: anti-tumor or anti-cancer agent, cytotoxic agent, cytostatic agent, anti-inflammatory agent, analgesic, anti-infective agent, growth inhibitory agent, immunogenic agent, immunomodulatory agent, and chemokine.

10. A method of treating cancer in a subject in need thereof, the method comprising administering to said subject an effective amount of the compound of claim 1.

11. The method of claim 10, wherein the cancer is prostate cancer, breast cancer, glioblastoma, ovarian cancer, lung cancer, head and neck cancer, esophageal cancer, skin cancer, melanoma, brain cancer, colorectal cancer, leukemia, lymphoma, or myeloma.

12. The method of claim 10, wherein the compound comprises: (i) a saRNA of CEBPA, p21, or p53 conjugated to one of phosphorothioated oligodeoxynucleotides (ODN) of SEQ ID NOs: 7-18 and 98-101, or (ii) a STAT ASO of one of SEQ ID NOs: 31-42 and 110-113 conjugated to one of phosphorothioated oligodeoxynucleotides (ODN) of SEQ ID NO: 7-18 and 98-101, and wherein the cancer in the subject is treated while simultaneously stimulating an immune response.

13. The method of claim 10, wherein the compound comprises saRNA of CEBPA, p21, or p53, or one of STAT ASO of SEQ ID NOs: 31-42 and 110-113, conjugated to one of phosphorothioated oligodeoxynucleotides (ODN) of SEQ ID NO: 29-30, and wherein the cancer in the subject is treated without simultaneously stimulating an immune response.

14. A method of treating an autoimmune disease in a subject in need thereof, the method comprising administering to said subject an effective amount of the compound of claim 1.

15. The method of claim 14, wherein the autoimmune disease is rheumatoid arthritis, Crohn's disease, ulcerative colitis, multiple sclerosis, psoriasis, or systemic lupus erythematosus (SLE).

16. The method of claim 14, wherein the compound comprises one of STAT ASOs of SEQ ID NOs: 31-42 and 110-113 conjugated to one of phosphorothioated oligodeoxynucleotides (ODN) of SEQ ID NO: 29-30, and wherein the autoimmune disease in the subject is treated without simultaneously stimulating an immune response.

17. A method of stimulating an immune response in a subject in need thereof, the method comprising administering to said subject an effective amount of a compound of claim 1, wherein the compound comprises one of a phosphorothioated oligodeoxynucleotide (ODN) sequences of SEQ ID NO: 7-18 and 98-101 conjugated to (i) a saRNA of CEBPA, p21, or p53 or (ii) an ASO according to any of SEQ ID NO: 31-42 and 110-113; or the pharmaceutical composition comprising the compounds comprising one of a phosphorothioated oligodeoxynucleotide (ODN) sequences of SEQ ID NO: 7-18 and 98-101 conjugated to (i) a saRNA of CEBPA, p21, or p53 or (ii) an ASO according to any of SEQ ID NO: 31-42 and 110-113.

18. A method of enhancing C/EBPα expression in a cell, the method comprising contacting the cell with an effective amount of (i) a compound comprising one of a phosphorothioated oligodeoxynucleotide (ODN) sequences of SEQ ID NO: 7-18, 29-30, and 98-101 conjugated to a saRNA of CEBPA, or (ii) a pharmaceutical composition comprising a compound comprising one of a phosphorothioated oligodeoxynucleotide (ODN) sequences of SEQ ID NO: 7-18, 29-30, and 98-101, conjugated to a saRNA of CEBPA.

19. A method of reducing the activity of a STAT transcription factor in a cell comprising contacting the cell with an effective amount of (i) a compound comprising one of a phosphorothioated oligodeoxynucleotide (ODN) sequences of SEQ ID NO: 7-18, 29-30, and 98-101 conjugated to an ASO according to any of SEQ ID NO: 31-42 and 110-113, wherein the ASO comprises a single-stranded DNA substituent, or (ii) a pharmaceutical composition comprising the compound comprising one of a phosphorothioated oligodeoxynucleotide (ODN) sequences of SEQ ID NO: 7-18, 29-30, and 98-101 conjugated to an ASO according to any of SEQ ID NO: 31-42 and 110-113, wherein the ASO comprises a single-stranded DNA substituent.

20. The method of claim 18, wherein said cell is a cancer cell.

* * * * *